(12) United States Patent
Sekino et al.

(10) Patent No.: US 6,383,183 B1
(45) Date of Patent: May 7, 2002

(54) HIGH FREQUENCY TREATMENT APPARATUS

(75) Inventors: Naomi Sekino, Hachioji; Yasuhiko Kikuchi, Machida; Kazuya Hijii, Hachioji; Masahide Ohyama, Hino; Kouji Yamauchi; Hiroyuki Takahashi, both of Hachioji; Takahiro Kogasaka, Hino; Akio Nakada, Hachioji; Takeaki Nakamura, Hino; Masatoshi Tonomura, Tokyo; Hideto Yoshimine; Hiroaki Matsumoto, both of Hachioji, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/288,579

(22) Filed: Apr. 7, 1999

(30) Foreign Application Priority Data

| Apr. 9, 1998 | (JP) | 10-097431 |
|---|---|---|
| May 8, 1998 | (JP) | 10-125914 |
| May 11, 1998 | (JP) | 10-127718 |
| May 22, 1998 | (JP) | 10-141112 |
| May 15, 1998 | (JP) | 10-133212 |
| Jun. 5, 1998 | (JP) | 10-157573 |
| Jun. 25, 1998 | (JP) | 10-178835 |

(51) Int. Cl.[7] .......................... A61B 18/04; A61B 18/18
(52) U.S. Cl. ..................... 606/34; 606/37; 606/45; 606/49; 606/50
(58) Field of Search ............... 606/32, 38–42, 606/45–50, 34, 37; 607/98, 101, 102, 115, 116

(56) References Cited

U.S. PATENT DOCUMENTS

| 5,554,110 A | 9/1996 | Edwards et al. | |
|---|---|---|---|
| 5,993,447 A | * 11/1999 | Blewett et al. | 606/50 |
| 6,093,186 A | * 7/2000 | Goble | 606/34 |
| 6,142,992 A | * 11/2000 | Cheng et al. | 606/34 |

FOREIGN PATENT DOCUMENTS

| JP | 2647557 | 8/1996 |
|---|---|---|
| JP | 8-229050 | 9/1996 |

* cited by examiner

Primary Examiner—Roy Gibson
(74) Attorney, Agent, or Firm—Frishauf, Holtz, Goodman, Langer & Chick, P.C.

(57) ABSTRACT

A high frequency treatment apparatus of the present invention comprises a high frequency generation section for supplying high frequency power, a control section, which is connected to the high frequency generation section, and which controls output of the high frequency generation section, having a first control mode in which the maximal output value of high frequency power supplied from the high frequency generation section is confined to be equal to or less than a first predetermined value and a second control mode in which the maximal output value of high frequency power supplied from the high frequency generation section is confined to be equal to or less than a second predetermined value which is less than the first predetermined value, a treatment tool, which is connected to the high frequency generation section, and which performs a treatment of a diseased part by supplying high frequency power from the high frequency generation section controlled by the control section to the diseased part, and a control mode setting section, which is connected to the control section, for selecting one of the first and second control modes.

15 Claims, 37 Drawing Sheets

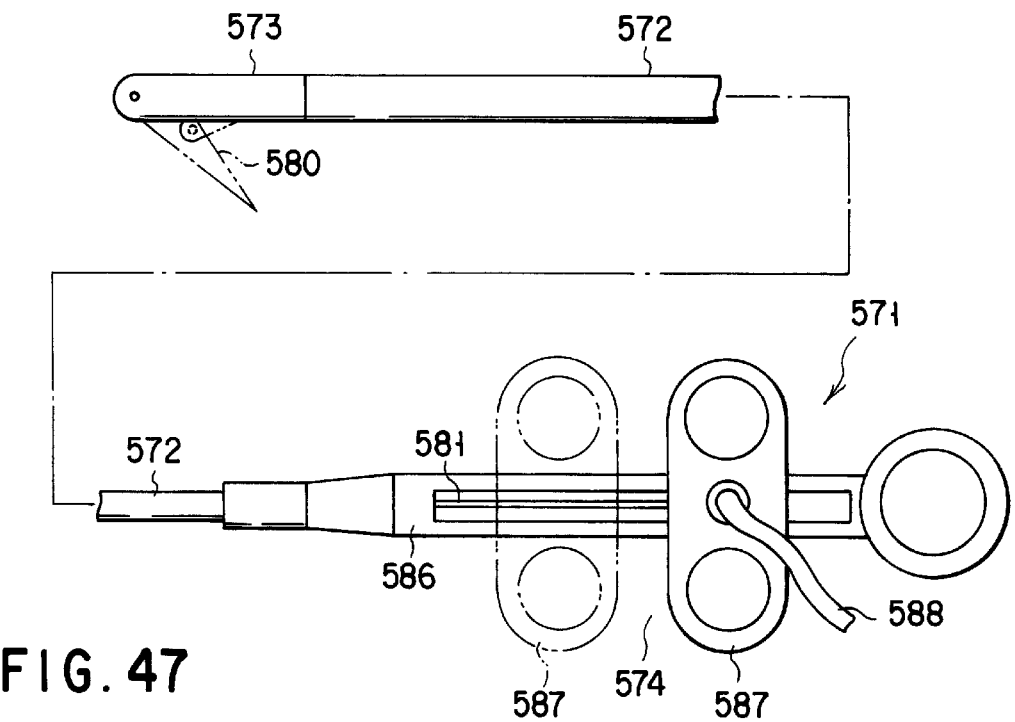
FIG. 47
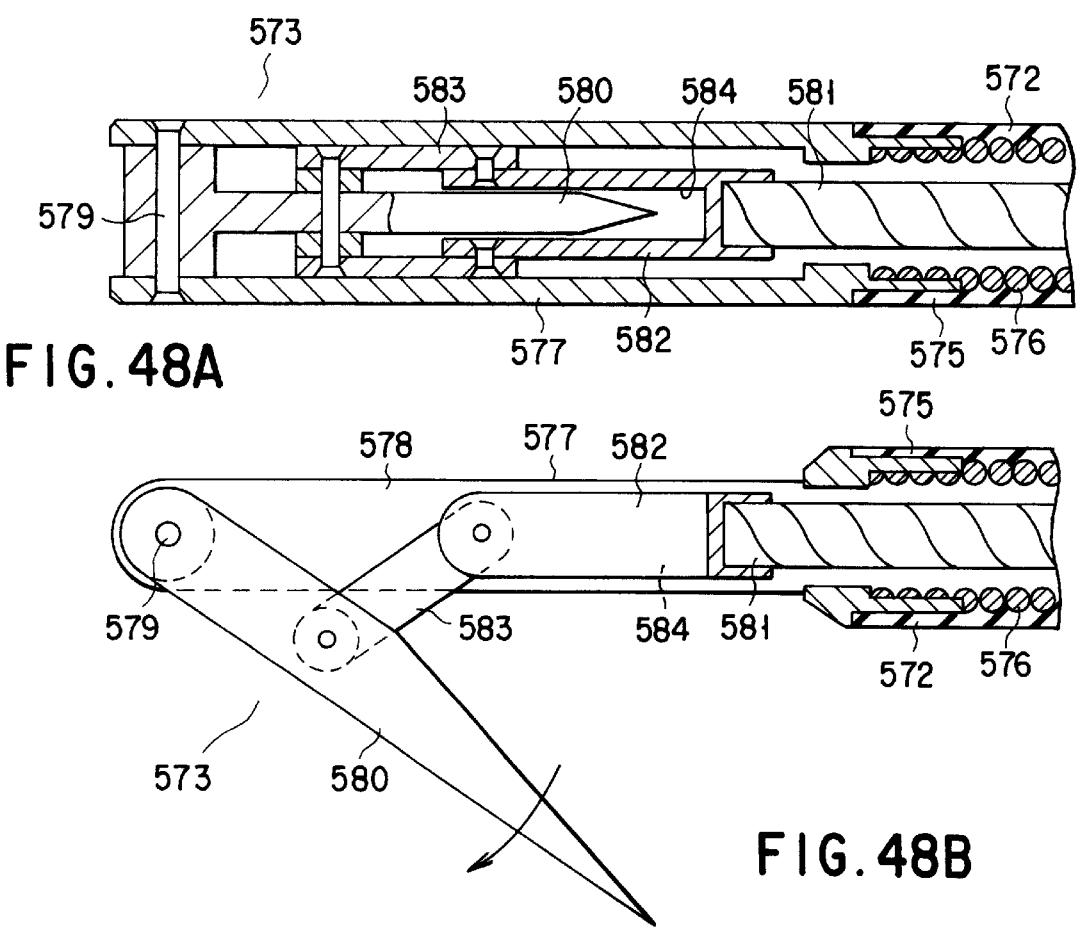
FIG. 48A
FIG. 48B

HIGH FREQUENCY TREATMENT APPARATUS

BACKGROUND OF THE INVENTION

The present invention relates to a high frequency treatment apparatus and particularly, to a high frequency treatment apparatus having a dissection (cutting) mode, a coagulation mode and a heating (ablation) mode.

A high frequency cautery apparatus which has heretofore been known is an apparatus by which a high frequency current is made to flow in biogenic tissues and thereby operations such as dissection (cutting), coagulation and the like are effected and has been used in a general surgical operation, an endoscopic surgical operation and the like. Development of a high frequency electrocautery apparatus (high frequency cautery apparatus) of a general type which can be adapted for various kinds of operative techniques has been progressed in company with advancement of operative techniques in recent years.

A high frequency electrocautery apparatus of a general type having a plurality of output modes in which output of a high frequency current can be changed according to a kind of operative technique has prevailed. The high frequency electrocautery apparatus effects an operation in a manner such that a high frequency cautery power source apparatus and an operative tool is connected to each other and high frequency power is supplied to an operative portion from the operative tool, wherein high frequency power supplied from the high frequency cautery power source apparatus has been required to be optimally controlled. Hence, as shown in the Jpn. Pat. Appln. KOKAI Publication No. 8-229050, a method has been adopted in a monopolar mode in which an output current which is supplied from a high frequency cautery power source apparatus for electrosurgery and a return current which returns are detected and compared with each other. In this way, a leakage current is indirectly detected and an impedance between an output terminal and return terminal of the high frequency cautery power source apparatus is detected. In a bipolar mode, a method has been adopted in which a temperature sensor is provided at the fore-end of an electrode and a temperature of the tissue surface is detected by the sensor. High frequency power which is supplied from the high frequency cautery power source apparatus has been optimally controlled based on such information described above.

On the other hand, as shown in Jpn. Pat. No. 2647557 and U.S. Pat. No. 5,554,110, an apparatus has been proposed in which not only is treatment energy directly applied to a target tissue, but an ablation treatment (hereinafter referred to as heating treatment) which correctly destroys the target tissue while minimizing an influence on peripheral tissues can be performed. This heat treatment apparatus can realize a treatment with a low adverse influence on the peripheral portion. In the device, for example, not only is high frequency power with small energy of the order of 10 W at a frequency of 482 KHz applied to an operative portion, but biogenic information of the peripheral portion such as temperature is detected, and thereby excessive heating of the peripheral tissues is prevented from occurring and the target tissues are correctly destroyed.

However, with a conventional high frequency electrocautery apparatus in use, since for example, high frequency power of a magnitude up to 300 W at a high frequency of 30 KHz to 1 MHz is applied to an operative portion to perform operations such as dissection, coagulation and the like, an influence on the peripheral tissues cannot be avoided. Besides, even when a small magnitude of high frequency power is set, since it is difficult that high frequency power is controlled so as to be necessary, proper energy for heat treatment with certainty and accuracy, there arises a problem that a heat treatment cannot be performed with safety and certainty.

BRIEF SUMMARY OF THE INVENTION

It is an object of the present invention to provide a high frequency treatment apparatus by which a heat treatment (ablation) of a biogenic tissue can be performed with safety and certainty together with operations such as dissection (cutting), coagulation and the like.

The object of the present invention is achieved by a high frequency treatment apparatus which will be described below.

That is, a high frequency treatment apparatus of the invention comprises:

a high frequency generation section for supplying high frequency power;

a control section, which is connected to the high frequency generation section, and which controls output of the high frequency generation section, having a first control mode in which the maximal output value of high frequency power supplied from the high frequency generation section is confined to be equal to or less than a first predetermined value, and a second control mode in which the maximal output value of high frequency power supplied from the high frequency generation section is confined to be equal to or less than a second predetermined value which is less than the first predetermined value;

a treatment tool, which is connected to the high frequency generation section, and which performs a treatment of a diseased part by supplying high frequency power from the high frequency generation section controlled by the control section to the diseased part; and a control mode setting section, which is connected to the control section, for selecting one of the first and second control modes.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 47 is a side view of a treatment tool of a high frequency treatment apparatus according to a nineteenth embodiment of the present invention;

FIGS. 48A and 48B are longitudinal sectional views of a operative section of the treatment tool of FIG. 47;

DETAILED DESCRIPTION OF THE INVENTION

Below, embodiments of the present invention will be described with reference to the accompanying drawings. As used herein, the term heating means ablation, and the term dissection means cutting.

Figure 1:
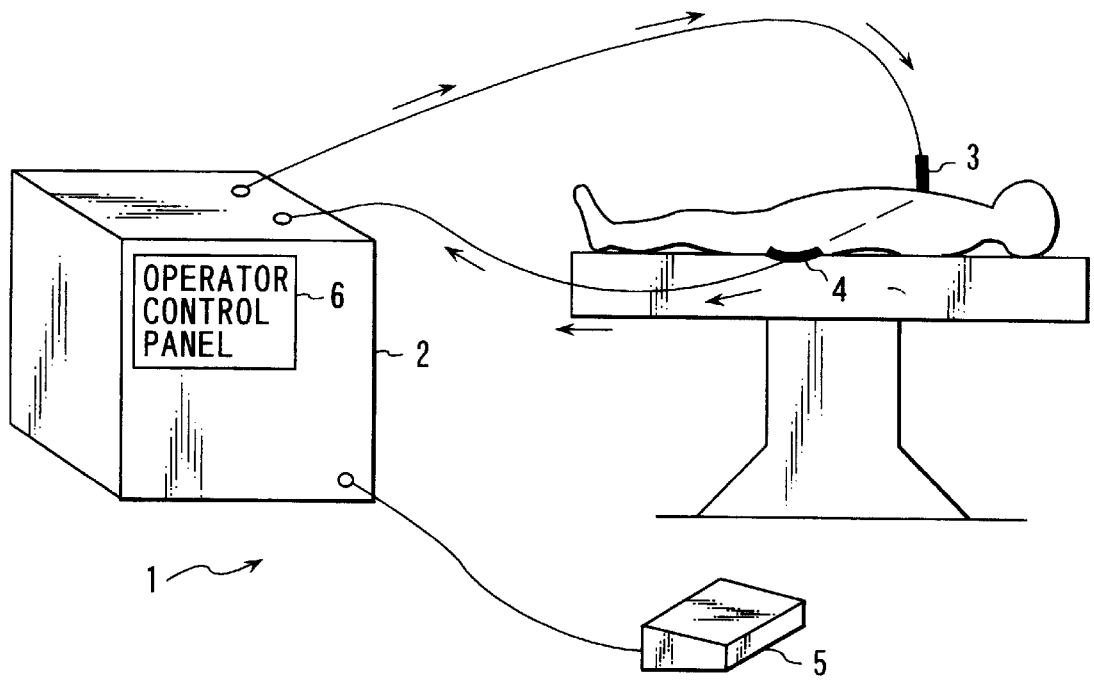
FIG. 1 is a diagram of a construction of a high frequency treatment apparatus according to a first embodiment of the present invention.
Figure 2:
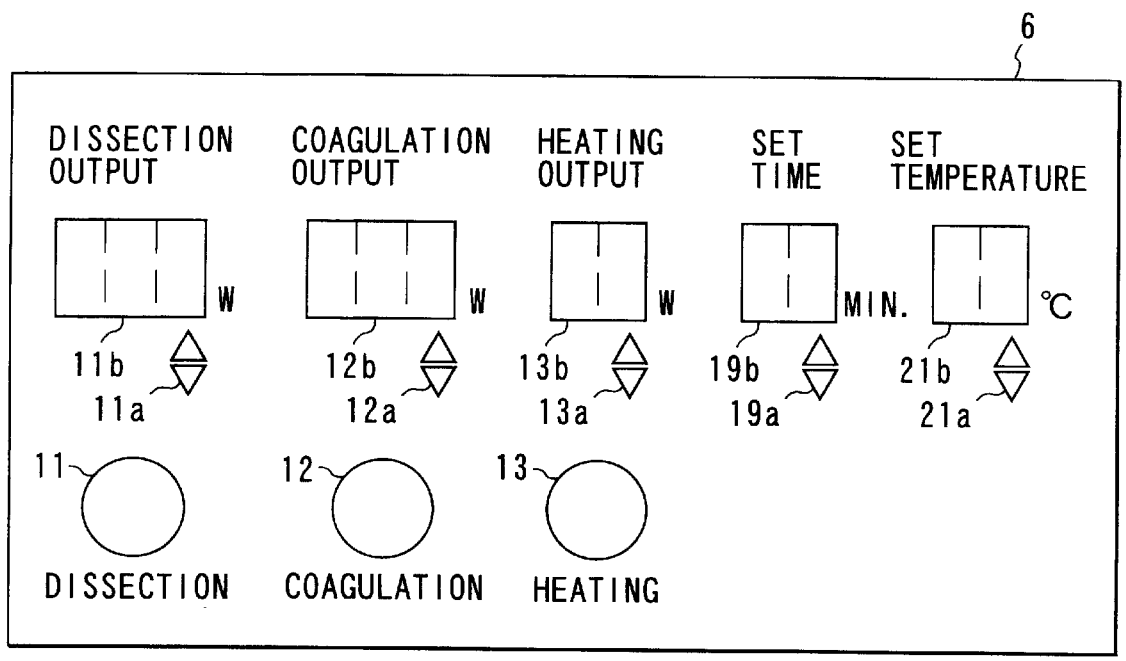
FIG. 2 is a diagram of construction of an operator control panel provided on the high frequency power generator of FIG. 1.

FIGS. 1 to 12 show the first embodiment of the present invention. A high frequency treatment apparatus 1 of the embodiment has a high frequency power generator 2 as the body of the apparatus, and a high frequency operative tool 3 as a treatment tool, an opposite electrode plate 4 which constitutes a return electrode for return of a high frequency current and power switches such as a foot switch 5 for power control and the like are connected to the high frequency power generator 2, wherein a hand switch, not shown, having a similar function to the foot switch 5 is provided to a hand piece of the high frequency operative tool 3. An operator control panel 6 is provided on an outside of the high frequency power generator 2 and the operator control panel 6 is an interface between an operator and a high frequency cautery apparatus. The operator control panel 6, as shown in FIG. 2, comprises: a dissection SW11, a coagulation SW12 and a heating SW13 which are mode switches (SW) for setting various kinds of output modes including a dissection (cutting) mode, a coagulation mode and a heating (ablation) mode; output setting SWs 11a, 12a, 13a for setting output power in selected output modes, and indication sections 11b, 12b, 13b for indicating the output power set values; a time setting SW 19a for setting an output time of output power, and an indication section 19b for indicating the output time set value; and a temperature setting SW21a for setting temperature of the peripheral region of an operative portion which is biologic information which is used for controlling output power, and an indication section 21b for indicating the temperature set value.

Figure 3:
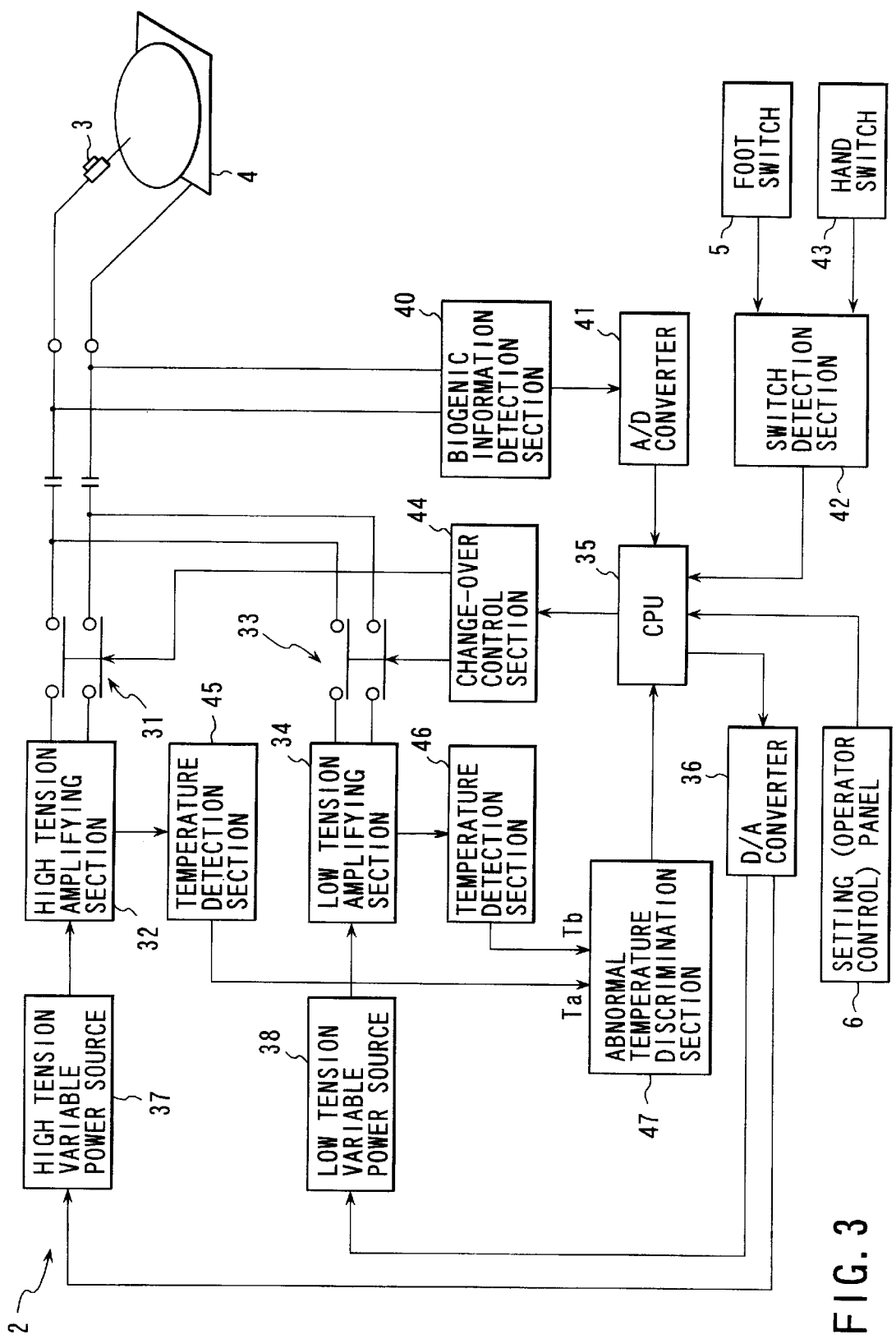
FIG. 3 is a block diagram showing construction of the high frequency power generator of FIG. 1.

The high frequency power generator 2, as shown in FIG. 3, comprises: a high tension amplifying section 32 for supplying high tension high frequency power to the high frequency operative tool 3 through a high tension SW31; and a low tension amplifying section 34 for supplying low tension high frequency power to the high frequency operative tool 3 through a SW33. The high tension amplifying section 32 can supply an output of high tension high frequency power, for example, up to 300 W at a high frequency from 300 KHz to 1 MHz, while the low tension amplifying section 34 can supply an output of low tension high frequency power, for example, of low energy up to as small as 10 W at a frequency of 482 KHz. The high frequency power generator 2 has a CPU 35 which is a main control section for controlling the sections and an analogue output instruction signal is supplied to a high tension variable power source 37 and a low tension variable power source 38 as high frequency generating sections from the CPU 35 through a D/A converter 36. The high tension variable power source 37 generates direct current power corresponding to an output instruction signal from the CPU 35 and supplies the power to the high tension amplifying section 32, and high tension high frequency power is generated in the high tension amplifying section 32 by controlling charge/discharge of a parallel resonance circuit composed of a primary winding of an output transformer and a capacitor in parallel connected to the primary winding through a combination of switching means, not shown. Likewise, the low tension variable power source 38 generates direct current power corresponding to an output instruction signal from the CPU 35 and supplies the power to the low tension amplifying section 34, and low frequency power is generated in the low tension amplifying section 34 by controlling charge/discharge of a parallel resonance circuit composed of a primary winding of an output transformer and a capacitor in parallel connected to the primary winding through a combination of switching means, not shown. The high frequency power generator 2 is connected to the high frequency operative tool 3 side and the opposite electrode plate 4 side, provided with a biogenic information detection section 40 for detecting biogenic information, which is correlated with temperature of the peripheral region of an operative portion, such as an output voltage, an output current, a return current, a biogenic electrostatic capacitance, a biogenic impedance and the like, and supplies the biogenic information detected by the biogenic information detection section 40 to the CPU 35 through an A/D converter 41.

The CPU 35 has connection with the operator control panel 6 and a switch detection section 42. An operating condition of an output switch such as the foot switch 4 or the hand switch 43 which is provided to the hand piece of the high frequency operative tool 3 is detected by the switch detection section 42 and a switch detection signal corresponding to an operating condition of an output switch is produced in the section and supplied to the CPU 35. A switch detection signal from the switch detection section 42, an output mode selection signal and a setting signal such as an output power set value and the like from the operator control panel 6 are all taken into the CPU 35 and the CPU 35 transmits output instruction signals to the high tension variable power source 37 and the low tension variable power source 38 so as to generate high frequency output power corresponding to an output mode, a setting signal such as an output power set value or an operating condition of an output switch. The CPU 35 performs ON/OFF control of the high tension switch 31 and the low tension switch 33 through a change-over control section 44 based on an output mode selection signal by the operator control panel 6, a switch detection signal from the switch detection section 42 and biogenic information detected by the biogenic information detection section 40 and thereby, controls supply of high tension high frequency power and low tension high frequency power to the high frequency operative tool 3.

In addition, temperature detection sections 45, 46 are respectively provided in the high tension amplifying section 32 and the low tension amplifying section 34. An abnormal temperature discrimination section 47 detects whether or not a temperature which has been detected by the temperature detection sections 45, 46, for example a temperature Ta of the high tension amplifying section 32 or a temperature Tb of the low tension amplifying section 34 exceeds a predetermined temperature and if it is detected that a temperature exceeds the predetermined temperature, the abnormal temperature discrimination section 47 judges that the temperature is abnormal and supplies an abnormal temperature signal to the CPU 35 in order to stop supply of high tension high frequency power and low tension high frequency power to the high frequency operative tool 3. When the CPU 35 is supplied with an abnormal temperature signal from the abnormal temperature discrimination section 47, the CPU 35 not only stops output instruction signals to the high tension variable power source 37 and the low tension variable power source 38, but performs control to set the high tension SW31 and the low tension SW33 to the OFF state through the change-over control section 44.

Then, operations of the high frequency treatment apparatus 1 of the embodiment constructed as described above will be described.

Figure 4:
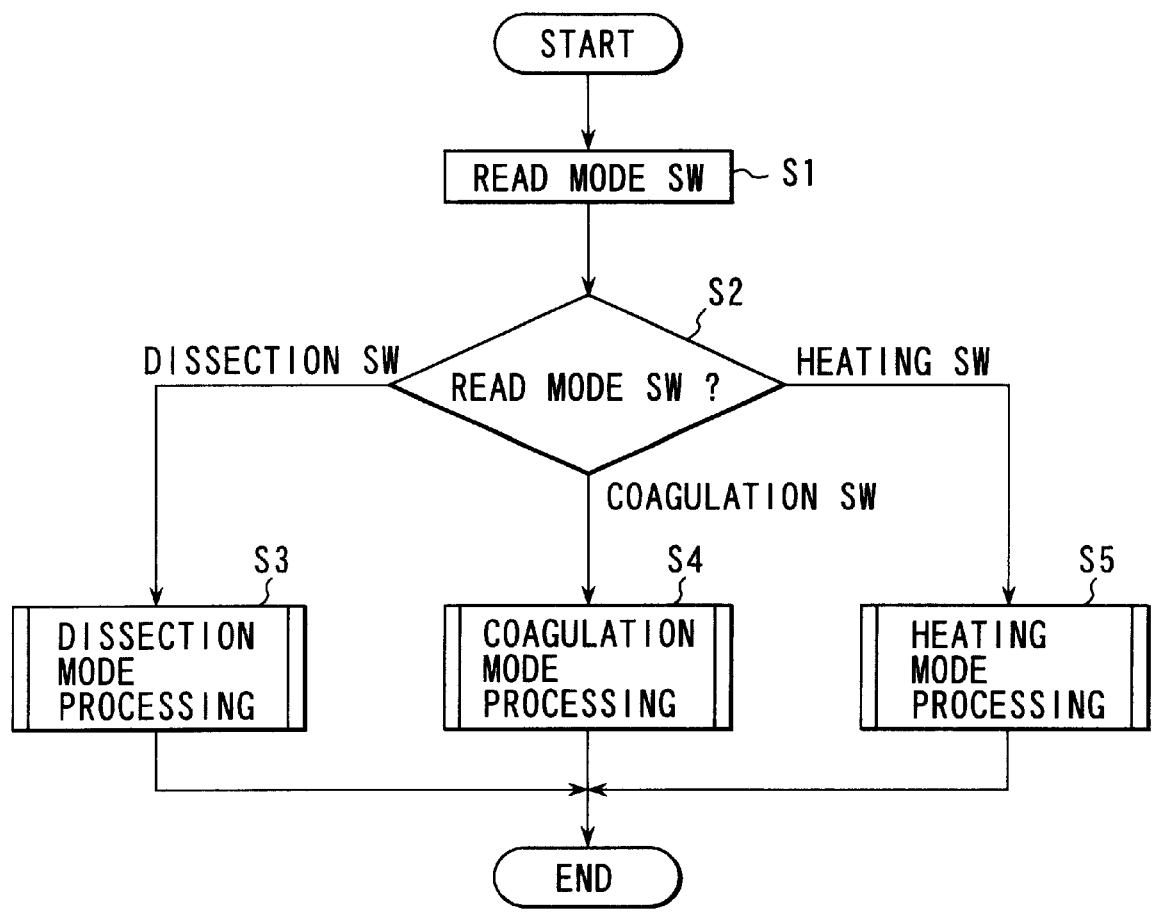
FIG. 4 is a flow chart showing a flow of processing by CPU of FIG. 3.

In the high frequency treatment apparatus 1 of the embodiment, as shown in FIG. 4, in step S1 the CPU 35 of the high frequency power generator 2 reads a mode SW (a dissection SW11, a coagulation SW12 and a heating SW13) from the operator control panel 6 and in step S2 discriminates the mode switch(a dissection SW11, a coagulation SW12 and a heating SW13) which has been read. If the mode SW is the dissection mode SW11, a subroutine for a dissection mode processing of step S3 is performed and thereafter the processing is terminated. If the mode SW is the coagulation SW12, a subroutine for a coagulation mode processing of step S4 is performed and thereafter the processing is terminated. If the mode SW is the heating SW12, a subroutine for heating mode processing of step S4 is performed and thereafter the processing is terminated.

Figure 5:
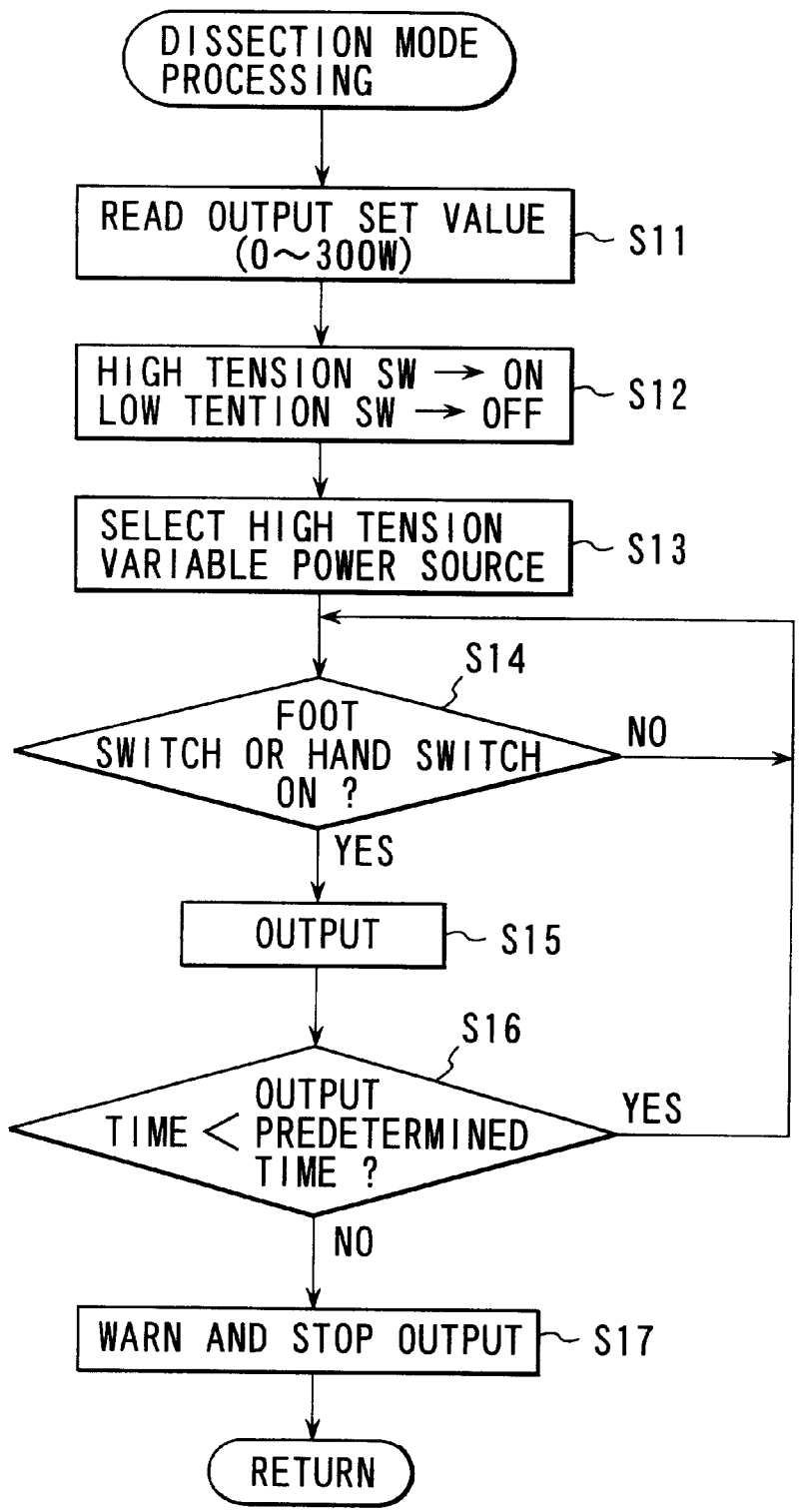
FIG. 5 is a flow chart showing a flow of a dissection mode processing of FIG. 4.

In the dissection mode processing of step S3, as shown in FIG. 5, in step S11 the CPU 35 reads an output set value of output power (0 to 300 W) in the dissection mode set by the output setting SW11a of the operator control panel 6 and in step S12 sets the high tension SW31 to the ON state and the low tension SW33 to the OFF state. Then, in step S13 the high tension variable power source 37 is selected as a output receiver of the D/A converter 36 and in step S14 the CPU 35 judges whether or not the foot switch 4 or the hand switch 43 is set to the ON state.

In step S14 the CPU 35 awaits till the foot switch 4 or the hand switch 43 is set to the ON state when neither of the switches has been set to the ON state. In step S14 when the CPU 35 judges that the foot switch 4 or the hand switch 43 has been set to the ON state, in step S15, the CPU 35 sends an output instruction signal to the D/A converter 36 and the D/A converter 36 transforms the output instruction signal into an analogue signal and sends the signal to the high tension variable power source 37.

Then, in step S16 the CPU 35 counts an output time of high tension high frequency power from the high tension amplifying section 32 which is sent out intermittently in an ON/OFF manner with an internal timer and judges whether or not the output time is within a predetermined time. If within the predetermined time, program flow returns to step S14, processing from steps 14 to 16 are repeated and when an output time is equal to or more than the predetermined time, in step S17 not only is a warning effected by warning means such as a speaker and the like, not shown, under judgment that the treatment has been completed but output of high tension high frequency power is stopped and the processing is terminated. Accordingly, the step S16 is processing to forbid continuous output equal to or longer than a predetermined time in output of high frequency power.

In the mean time, during repetition of processing from step S14 to S16, when biogenic information such as an output voltage, an output current or a return current, a biogenic electrostatic capacitance, a biogenic impedance or the like taken in through the A/D converter 41 exceeds a predetermined value, and when a temperature of the high tension amplifying section 32 is abnormal and an abnormal temperature signal is supplied from the abnormal temperature discrimination section 47, program flow goes to step S17. Then, not only a warning is effected by warning means such as a speaker and the like, not shown, but output of the high tension high frequency power is stopped and the processing is terminated.

Figure 6:
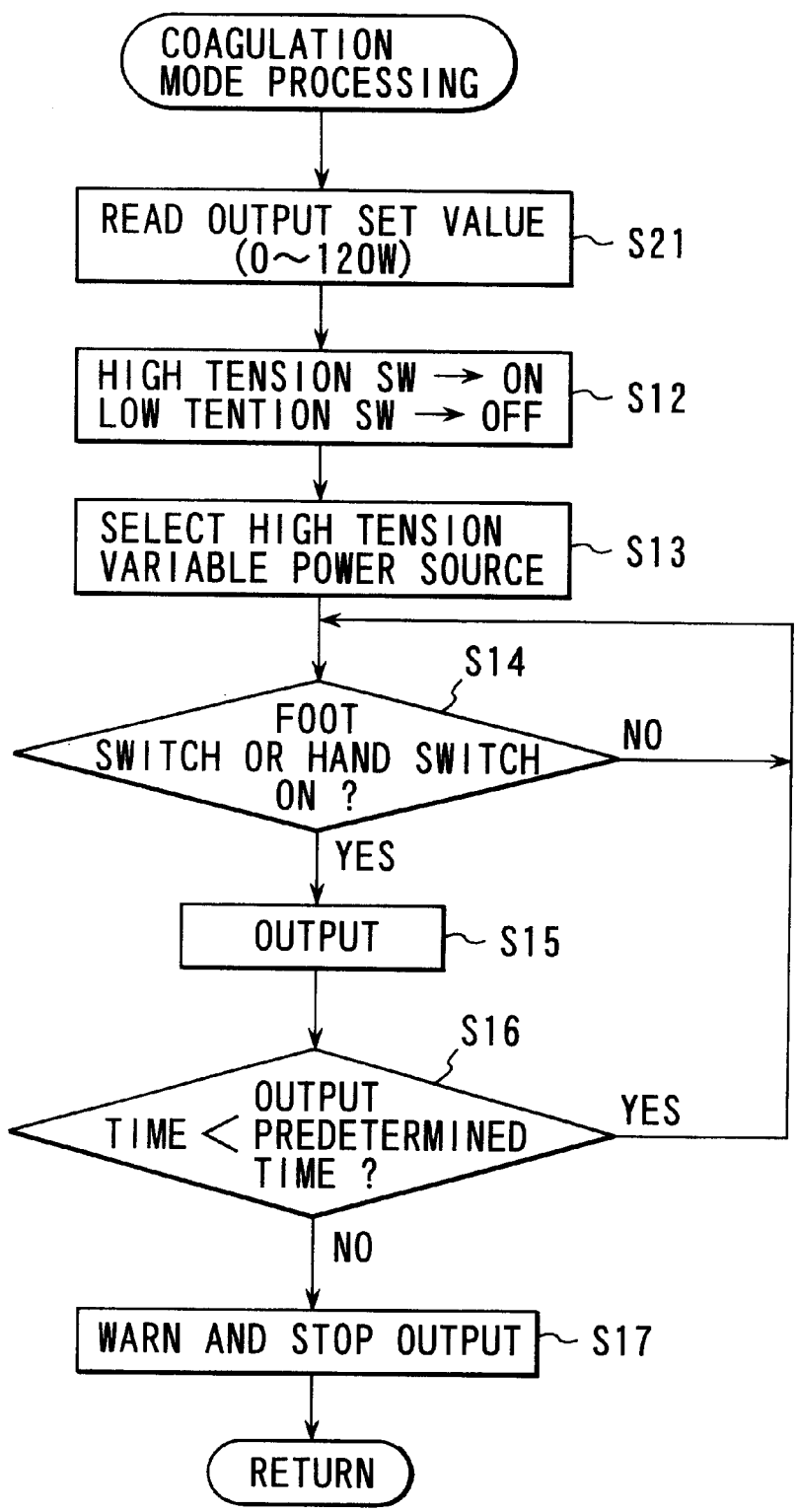
FIG. 6 is a flow chart showing a flow of a coagulation mode processing of FIG. 4.

In the coagulation mode processing of step S4, as shown in FIG. 6, the CPU 35 reads an output set value (0 to 120 W) of output power in the coagulation mode set by the output setting SW12a of the operator control panel 6 in step S21. Thereafter, the steps 12 to 17 described in the dissection mode processing. (see FIG. 5) are performed. Detailed description of the processing from steps 12 to 17 is omitted because of overlapping.

Figure 7:
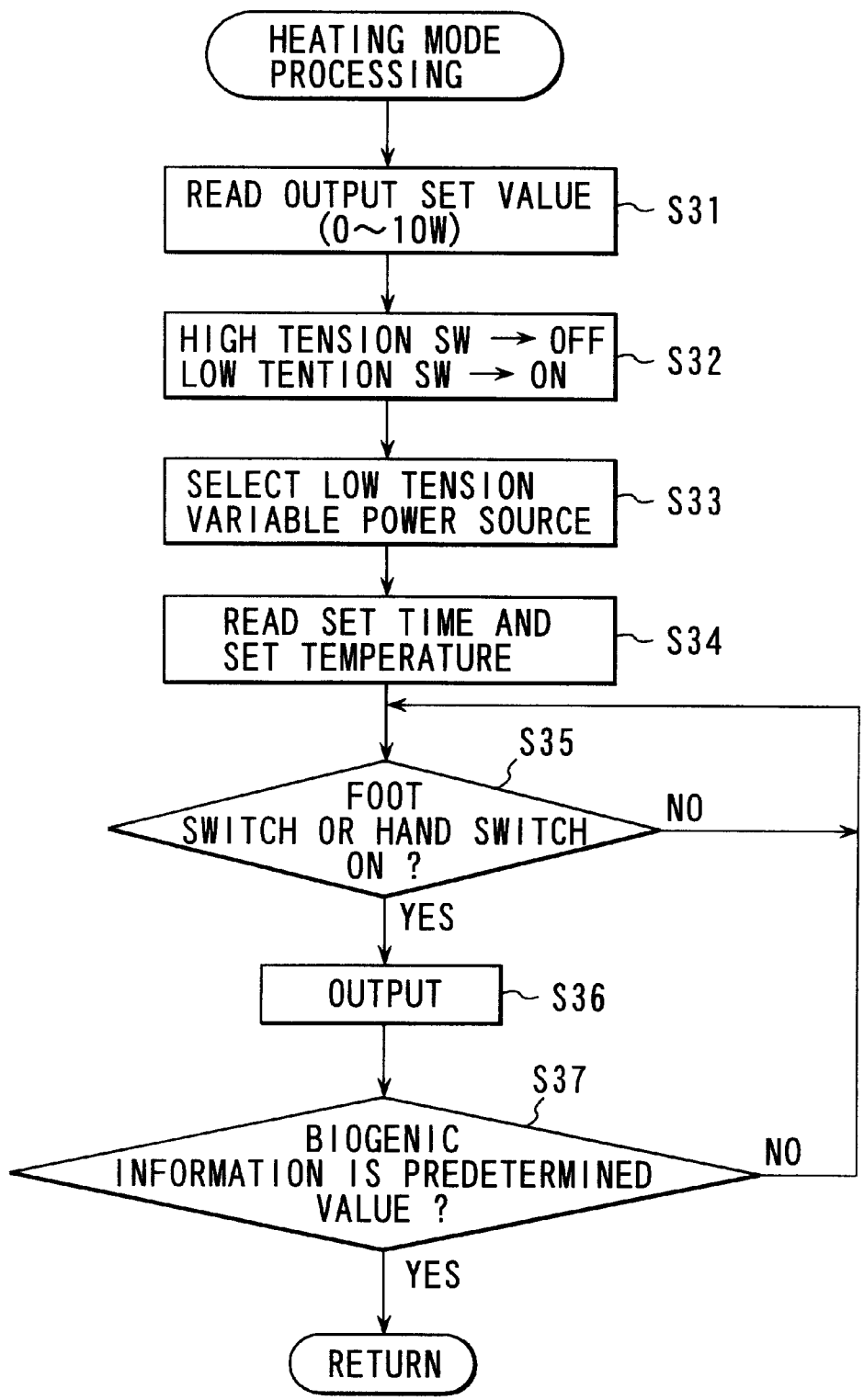
FIG. 7 is a flow chart showing a flow of a heating mode processing of FIG. 4.

In the heating mode processing of step S5, as shown in FIG. 7, the CPU 35 reads an output set value of output power (0 to 10 W) in the heating mode set by the output setting SW13a of the operator control panel 6 in step S31 and in step S32 sets not only the high tension SW31 to the OFF state, but the low tension SW33 to the ON state. Then, in step S33 the CPU 35 selects the low tension variable power source 38 as an output receiver of the D/A converter 36 and in step S34 reads a set time set by the time setting SW19a and a set temperature of the peripheral region of a operative portion set by the temperature setting SW21a from the operator control panel 6.

Then, in step S35 the CPU 35 judges whether or not the foot switch 4 or the hand switch 43 is set to the ON state. When neither the foot switch 4 nor the hand switch 43 has been set to the ON state, the CPU 35 awaits till either of both is set to the ON state. In step S35 if the CPU 35 judges that either the foot switch 4 or the hand switch 43 has been set to the ON state, in step S36 the CPU 35 sends out an output instruction signal to the D/A converter 36 during a set time set by the time setting SW19a and the D/A converter 36 converts the signal into an analogue signal to supply the signal to the low tension variable power source 38.

The CPU 35 compares biogenic information such as an output voltage, an output current or an return current, a biogenic electrostatic capacitance and a biogenic impedance or the like taken in through the A/D converter 41 with a predetermined value which has a correlation with a set temperature of the peripheral region of a operative portion set by the temperature setting SW21. If the biogenic information is within a predetermined value, then program returns to step S35 and processing from steps S35 to S37 is repeated, and if the biogenic information has reached to a predetermined value, the processing is terminated under judgment that the treatment has been completed.

In the mean time, during the repetition from steps S35 to S37, when a temperature of the low tension amplifying section 34 becomes abnormal and the CPU 35 is supplied with an abnormal temperature signal from the abnormal temperature discrimination section 47, not only is a warning immediately effected by warning means such as a speaker and the like, not shown, for processing for abnormality, but output of high tension high frequency power is stopped and the processing is terminated under judgment that the treatment has been completed.

In the heating mode, there is no processing which forbids continuous output equal to or longer than a predetermined time of output of high frequency power as in the cases of the dissection mode or the coagulation mode (step S16 of FIG. 5).

Figure 8:
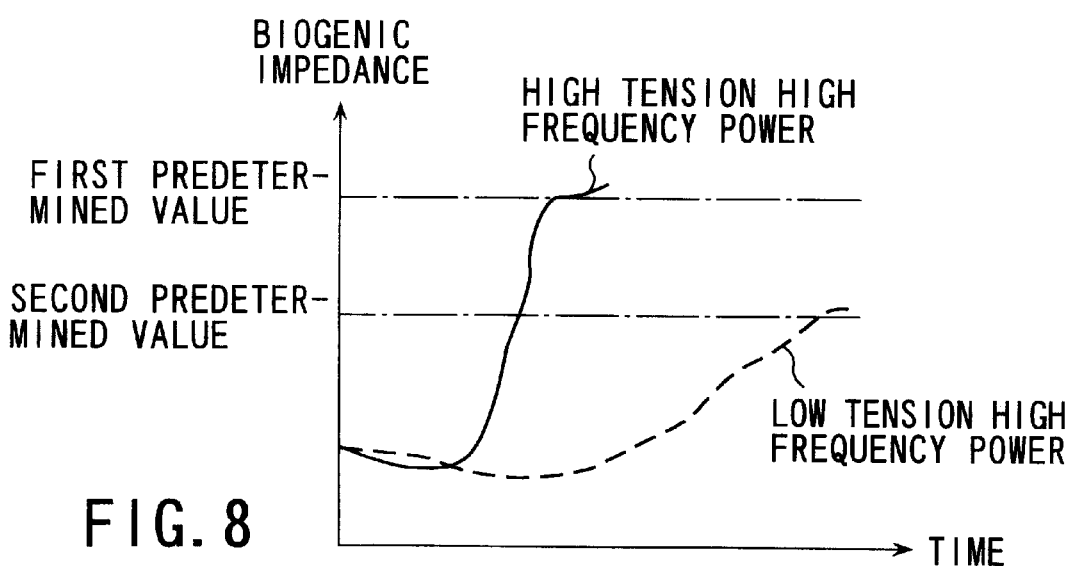
FIG. 8 is a characteristic graph showing changes in biogenic impedance in company with high frequency power generated from the high frequency power generator of FIG. 3.

A biogenic impedance which is biogenic information, as shown in FIG. 8, is decreased immediately after the output in both cases of high tension high frequency power and low tension high frequency power, since liquid in tissues is ionized, but thereafter, water is deprived of the tissues, temperature goes up and the tissues are degenerated.

In FIG. 8, a solid line indicates a change in biogenic impedance which is biogenic information caused by application of high tension high frequency power and a broken line indicates a change in biogenic impedance which is biogenic information caused by application of low tension high frequency power. In the case of the coagulation mode in which high tension high frequency power is employed, tissue degeneration instantly occurs because of high output and thereby a biogenic impedance is also increased, whereas in the case of the heating mode in which low tension high frequency power is employed, tissue degeneration is slow to progress because of low output and thereby a biogenic impedance is smaller than in the case of the coagulation mode or the like.

Figure 9:
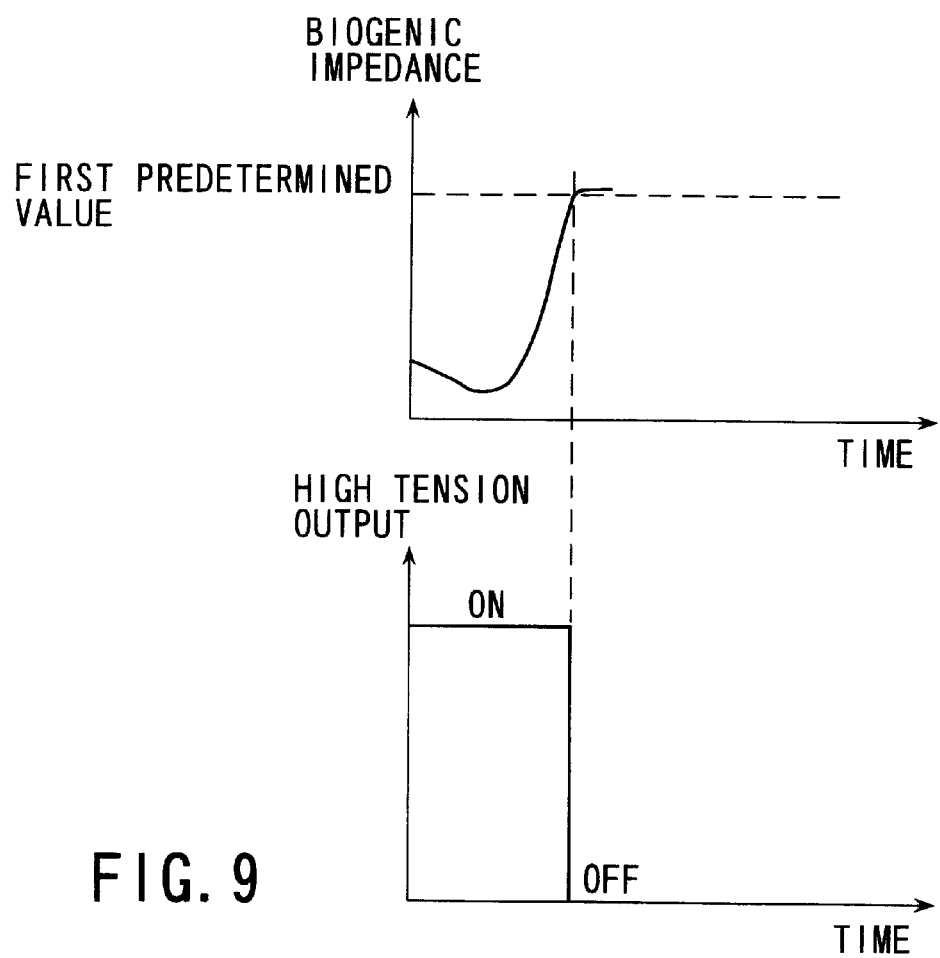
FIG. 9 is a graph showing output control of high frequency power in the dissection mode of FIG. 5 or in the coagulation mode of FIG. 6.

Hence, in the case of the dissection mode or the coagulation mode in which high tension high frequency power is employed, a predetermined value of a biogenic impedance is set as a first predetermined value and when a biogenic impedance exceeds the first predetermined value, program immediately goes to step S17 (see FIG. 5) for abnormality processing and not only is a warning effected by warning means such as a speaker and the like, but as shown in FIG. 9, output of high tension high frequency power is stopped and the processing is terminated.

Figure 10:
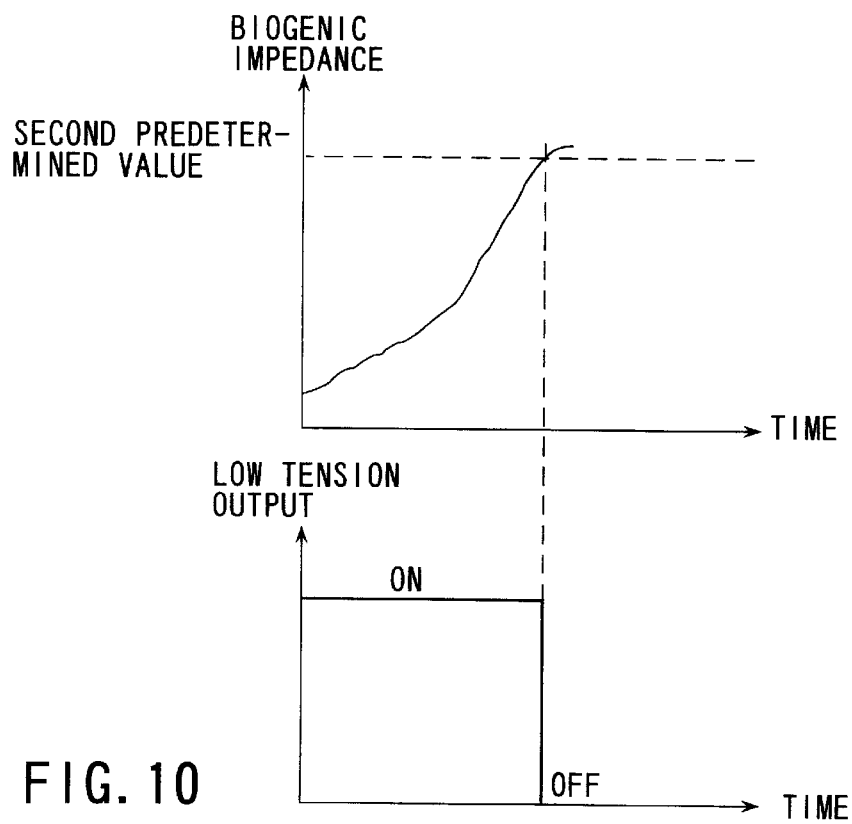
FIG. 10 is a graph showing output control of high frequency power in the heating mode of FIG. 7.

In the case of the heating mode in which low tension high frequency power is employed, a predetermined value is set as a second predetermined value smaller than the first predetermined value and as shown in FIG. 10, when a biogenic impedance has reached the second predetermined value during a set time, the processing is terminated under judgment that the treatment has been completed.

Figure 11:
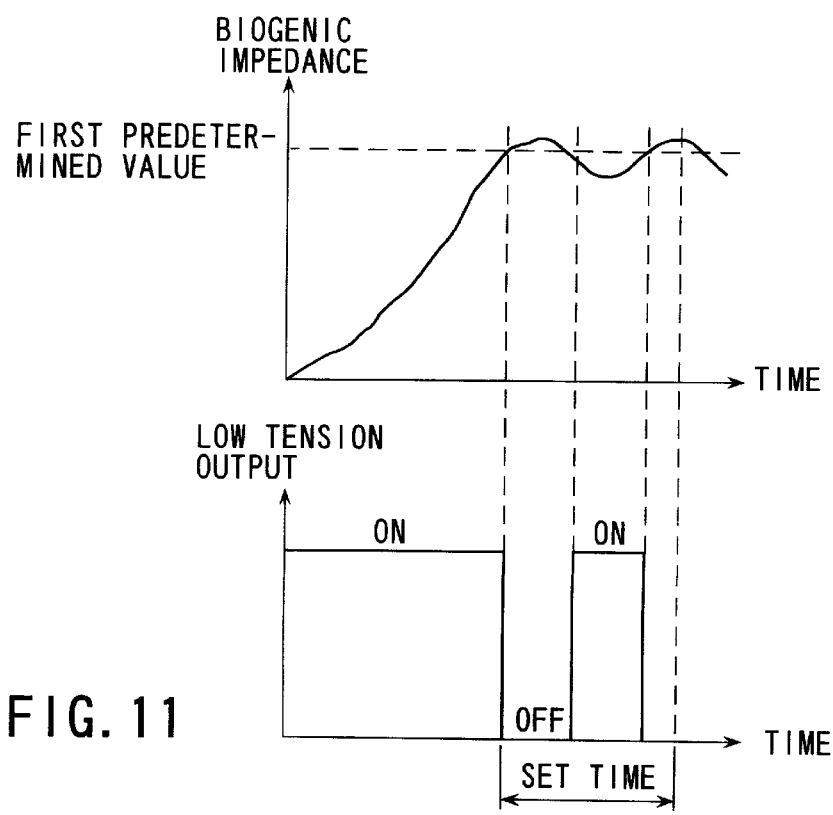
FIG. 11 is a graph showing a modification of output control of high frequency power of FIG. 10.

In the mean time, in the case of the heating mode, a way of processing is not limited to this but as shown in FIG. 11, even when a biogenic impedance has reached to the second predetermined value, low tension high frequency power is supplied in an ON/OFF manner so that a set time and a biogenic impedance keep the respective second predetermined values and after a set time is elapsed, the processing may be terminated under judgment that the treatment has been completed.

As described above, since in the embodiment, in the cases of the dissection mode and the coagulation mode, high tension high frequency power is employed, while in the case of the heating mode, low tension high frequency power is employed, heating treatment can be performed with safety and certainty together with operations of dissection, coagulation and the like of biogenic tissues.

Since processing in which continuous output longer than a predetermined time of output of high frequency power is forbidden is executed in the cases of the dissection mode and the coagulation mode, but not in the case of the heating mode, not only can treatment in the dissection mode or the coagulation mode be performed with safety and certainty, but treatment in the heating mode can be performed within a set time, so that heating treatment can be performed with certainty.

In the mean time, a temperature sensor is provided to a fore-end of the high frequency operative tool 3, a temperature of the peripheral region of an operative portion is directly detected in stead of a biogenic impedance and the temperature detected may be compared with a predetermined temperature for control.

Figure 12:
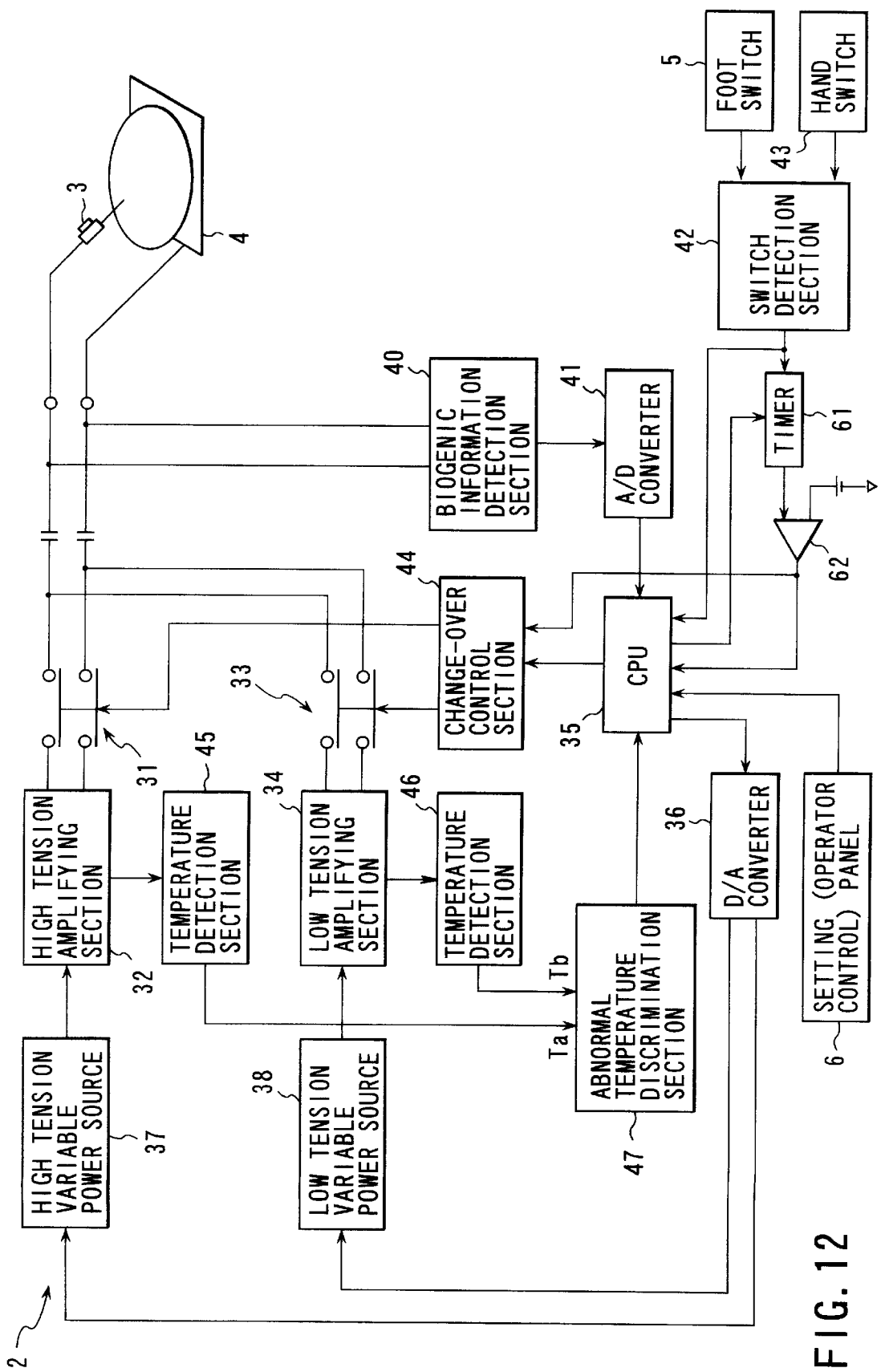
FIG. 12 is a block diagram showing a modified construction of the high frequency power generator of FIG. 1.

While, in the above described embodiment, prohibition of continuous output longer than a predetermined time of output of high frequency power in the dissection mode or the coagulation mode is realized by a software (step S16 of FIG. 5), a way of processing is not limited to this, but, for example, as shown in FIG. 12, a constitution can be adopted in which a timer 61 by which a time during which a switch detection signal of the switch detection section 42 assumes the ON state is measured and a comparator 62 by which a time measured by the timer 61 and a predetermined time are compared with each other are provided to the high frequency power generator 2.

In this case, the timer 61 can perform a count operation in the dissection mode and the coagulation mode under control of the CPU 35, while in the heating mode, the count operation is canceled. When a time measured by the timer 61 exceeds the predetermined value in comparison by the comparator 62, a time-up signal is sent to the change-over control section 44 and the CPU 35 from the comparator 62, and not only does the change-over section 44 set the high tension SW31 and the low tension SW33 to the OFF state according to the time-up signal, but the CPU 35 resets an output instruction signal to the D/A converter 36.

The timer 61 and the comparator 62 thus constitutes continuous operation prohibition means for prohibiting continuous output equal to or longer than a predetermined time of output of high frequency power in the dissection mode and the coagulation mode, while continuous-operation-prohibition cancellation means that the CPU 35 cancels operation of the continuous operation prohibition means is constituted in the heating mode by canceling a count operation of the timer 61. With this constitution, too, a similar action and effect to those of the embodiment can be obtained.

Figure 13:
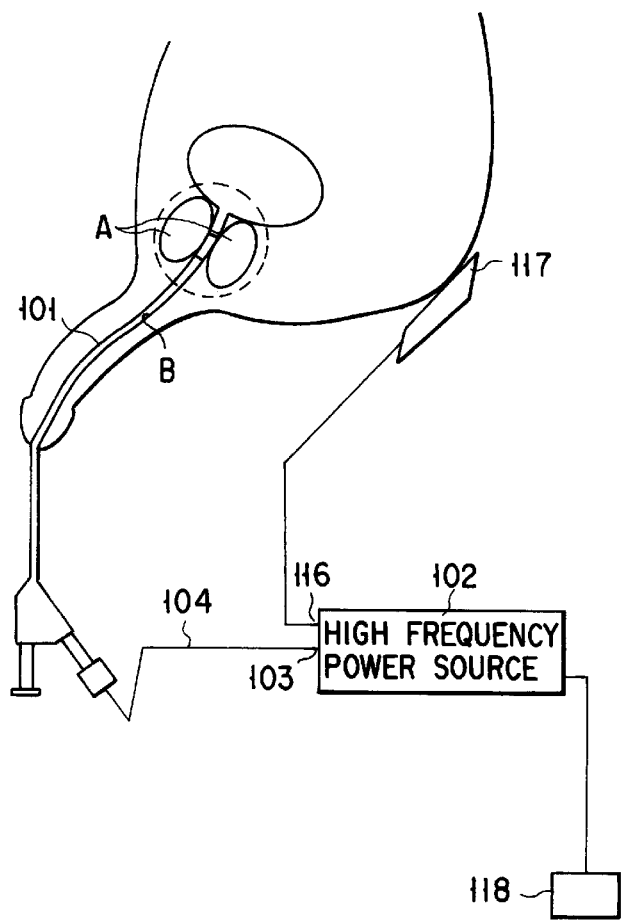
FIG. 13 is a diagram of a schematic construction of a high frequency treatment apparatus according to a second embodiment of the present invention.

FIGS. 13 to 17 show the second embodiment of the present invention. As shown in FIG. 13, a high frequency treatment apparatus according to the embodiment comprises: a probe 101 as a treatment tool which can be inserted into the urethra B; and a high frequency power source 102 as a high frequency generation section. The probe is electrically connected to the high frequency power source 102 by way of a electrode cable 104. A foot switch 118 for controlling an output of the high frequency power source 102. A foot switch 118 for controlling output of the high frequency power source 102 and an opposite electrode plate 117 for recovering a high frequency current which is supplied from electrodes 109, 110, described later, of the probe 101 are connected to the high frequency power source 102.

Figure 15:
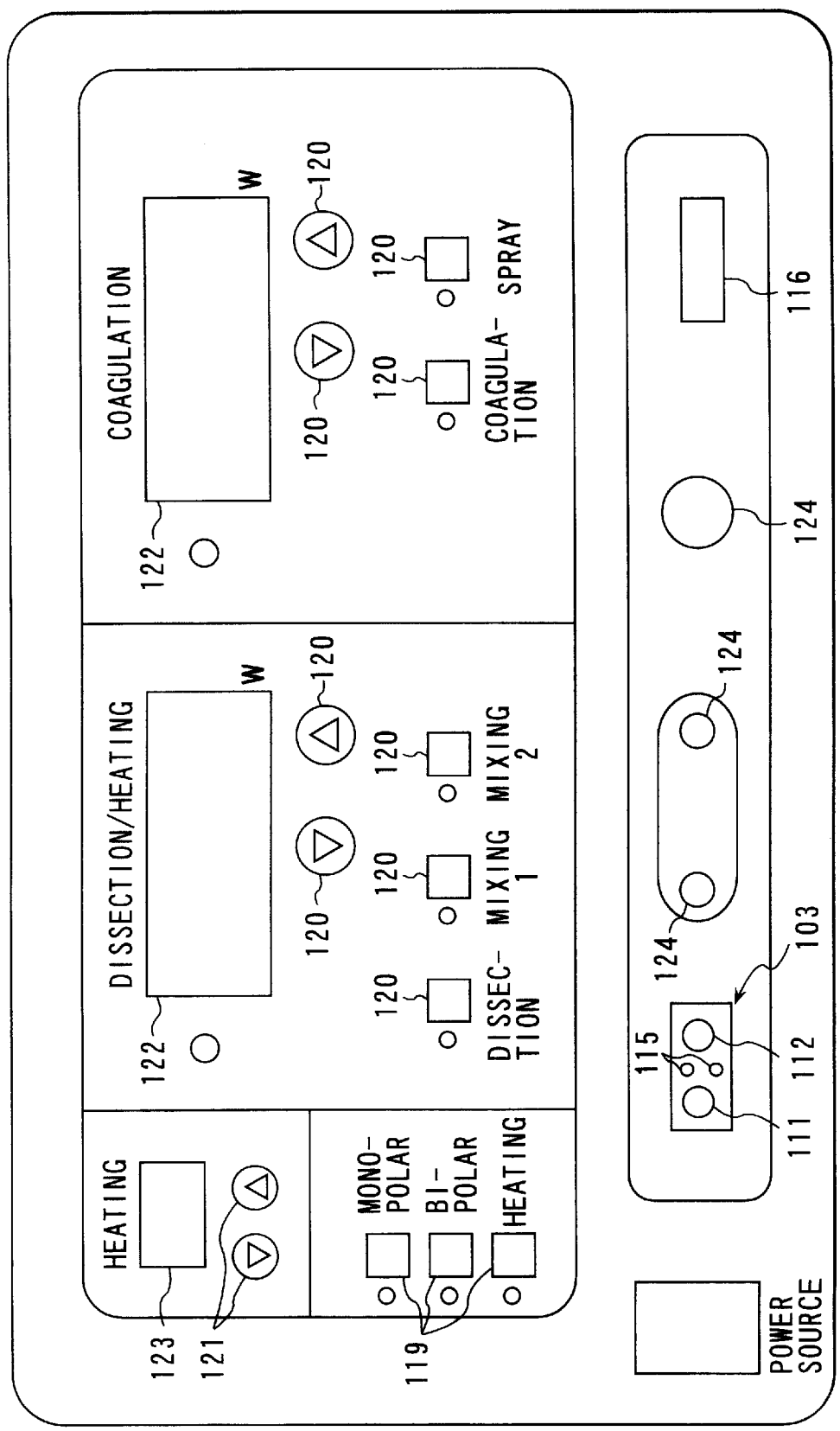
FIG. 15 is a front view of a front panel of a high frequency power source constituting the high frequency treatment apparatus of FIG. 13.

A front panel of the high frequency power source 102 is shown in FIG. 15. As shown in the figure, the front panel is provided with: an operation mode selection switch 119 for selecting a form and condition of operation, that is dissection or heating; an output mode setting switch 120 for setting a kind and power of out put; a temperature setting switch 121 for selecting a set temperature in the heating; an output setting indicator 122 for indicating an output power value set by the output mode setting switch 120; a temperature setting indicator 123 for indicating a set temperature in the heating set by the temperature setting switch 121; a heating electrode connection port 113 to which the electrode cable 104 is connected; an opposite electrode plate connection port 116 to which the opposite electrode plate 117 is connected; and an excision electrode connection port 124 to which an electrode for excision, not shown, is connected. The heating electrode connection port 113 is provided with high frequency output terminals 111, 112 and a temperature measurement terminal 115. The high frequency power source 102 comprises an output section for supplying high frequency power and a control section for controlling the output section.

Figure 14:
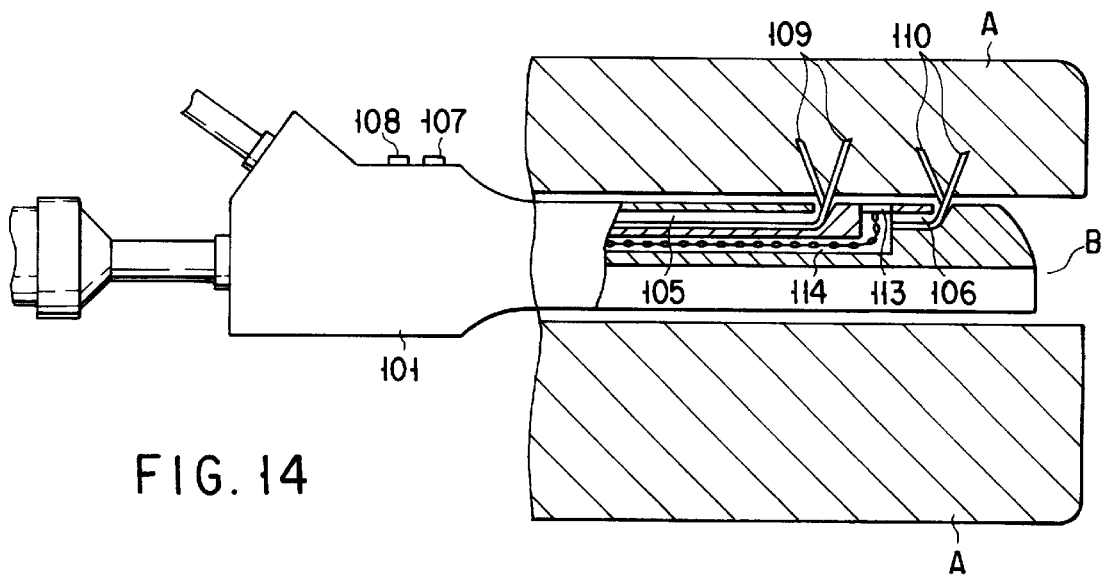
FIG. 14 is a sectional view of a probe constituting the high frequency treatment apparatus of FIG. 13.

As shown in FIG. 14, the probe 101 has two channels 105, 106. The fore-ends of the channels extend along a direction inclined to the central axis of the probe 101 and the channels 105, 106 respectively have openings on a side surface of the fore-end of the probe 101. Especially in the embodiment, the channel 105, 106 have the openings in the same side with respect to a plane which includes the central axis of the probe 101. Electrodes 109, 110 are in a forward/backward movable manner inserted in the inside of the channels 105, 106 respectively. Each fore-end of the electrode 109, 110 is forked in two ways and has two prongs like sharp needles. Operation switches 107, 108 for operating the electrodes 109, 110 so as to independently move forward or backward the electrodes 109, 110 in the respective channels 105, 106 are provided in the proximal side of the probe 101. A temperature sensor 113 is provided at the fore-end of the probe 101.

Two power supply lines extending from the respective electrodes 109, 110 extends through the insides of the probe 101 and the electrode cable 104 and when the electrode cable 104 is connected to the heating electrode connection port 103 of the high frequency power source 102, the two power supply lines are respectively connected to high frequency output terminals 111, 112 (see FIG. 15) of the heating electrode connection port 103. A signal line 114 extending from the temperature sensor 113 extends through the insides of the probe 101 and the electrode cable 104 and when the electrode cable 104 is connected to the heating electrode connection port 103 of the high frequency power source 102, the signal line 114 is connected to a temperature measurement terminal 115 of the heating electrode connection port 103.

Figure 16:
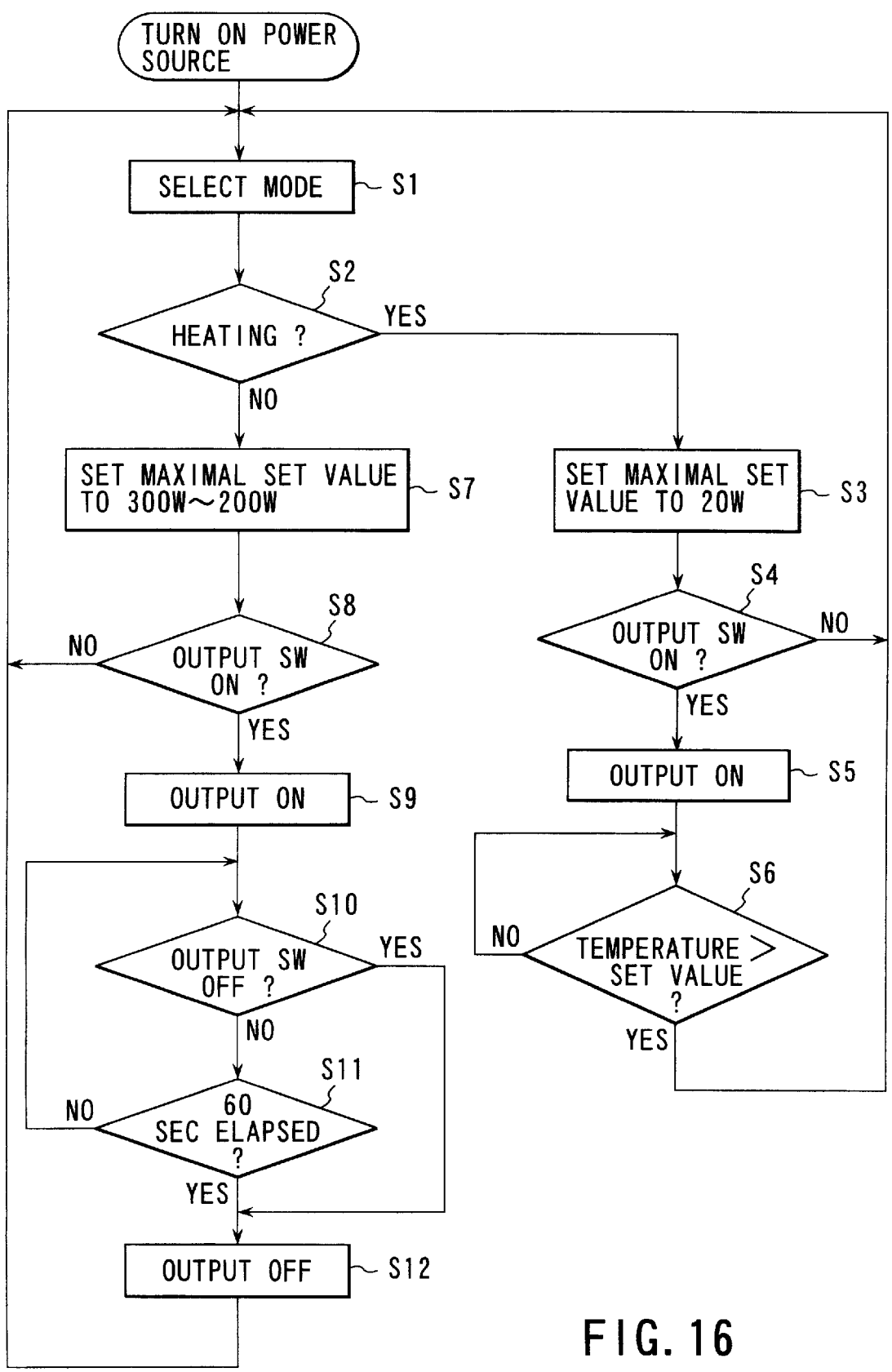
FIG. 16 is a flow chart showing output control of a high frequency power source.
Figure 17:
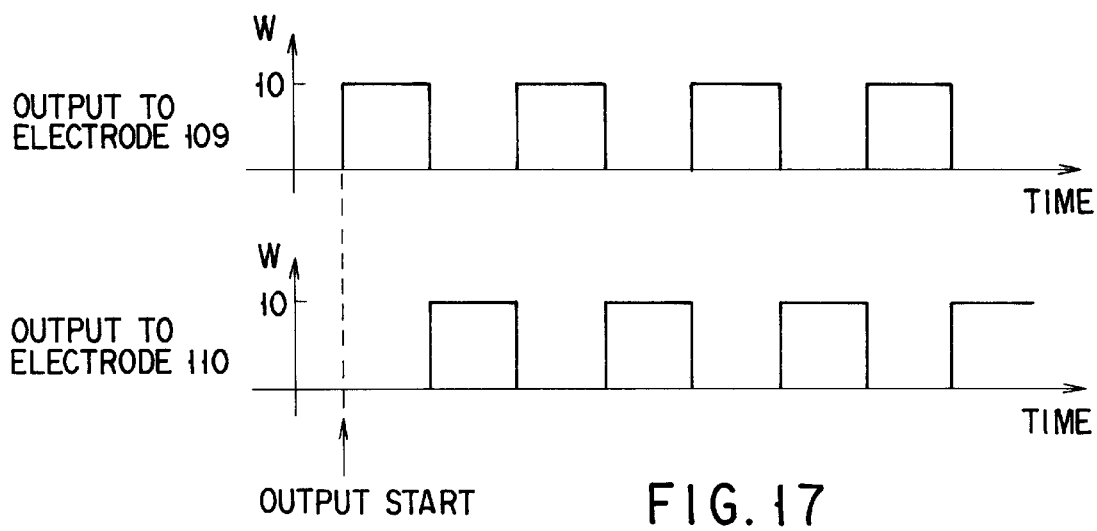
FIG. 17 is a time chart of high frequency power as output.

Then, the case where a prostate treatment is performed using the high frequency treatment apparatus with the above described construction will be described with reference to a flow chart of FIG. 16 and a waveform of FIG. 17.

When the prostate is subjected to a heat treatment, the opposite electrode plate 117 is mounted on a patient as shown in FIG. 13 and the opposite electrode plate 117, the probe 101 and the foot switch 118 are connected to the high frequency power source 102. Then, not only is a processing form and condition (operation mode) selected by the operation mode selection switch 119 on the front panel of the high frequency power source 102, but output power is set by the output mode setting switch 120 (step S1 of FIG. 16). At this point, heating is selected by the operation mode selection switch 119. The control section built in the high frequency power source 102 recognizes an operation mode set by the operation mode selection switch 119 (S2) and when a set mode is the heating mode, the control section makes setting of a kind of output by the output mode setting switch 120 impossible and further has power supplied from the output section restricted to the maximal 20 W (S3). That is, power setting more than 20 W by the output mode setting switch 120 is impossible. Thereafter, a temperature after the heating is completed is set by the temperature setting switch 121 and the setting preparation is completed.

When output setting by the front panel has been completed, the probe 101 is inserted through the urethra B and the fore-end of probe 101 is positioned in the vicinity of the prostate A. The electrodes 109, 110 are protruded from the openings of the channels 105, 106 to perform paracentesis into the prostate A by operating the switches 107, 108 provided at the proximal side of the probe 101. In this state, when the foot switch 118 is stepped down once (thereafter, a stepping-down pressure can be released), the control section recognizes the stepping-down (S4) and supplies high frequency power from the output section (S5). At this point, the control section makes the output section send out power which is indicated on the output setting indicator 122 in the timing as shown in FIG. 17 to the high frequency output terminals 111, 112 alternately.

The high frequency power sent out to the high frequency output terminals 111, 112 is supplied to the respective electrodes 109, 110 through the power supply lines and thereby, heating of the prostate is effected. In this case, since the two electrodes 109, 110 are employed and the fore-end of each of the electrodes 109, 110 is forked in two ways, not only is the prostate A heated in a uniform manner across a very large extent, but since power is alternately supplied to the high frequency output terminals 111, 112 (accordingly, the respective electrodes 109, 110), a high frequency current density does not decrease. The control section monitors a temperature of a treatment site through a detection signal from the temperature sensor 113 connected to the temperature measurement terminal 115 and stops high frequency output when a temperature of the treatment site exceeds a set temperature indicated on the temperature setting indicator 123 (S6).

On the other hand, when the prostate A is excised, an excision electrode, not shown, is connected to an excision electrode connection port 124 of the high frequency power source 102. Subsequently, not only is a processing form and condition (operation mode) selected by the operation mode selection switch 119 on the front panel of the high frequency power source 102, but a kind of output and output power are set by the output mode setting switch 120 (S1 of FIG. 16). At this point, a mono-polar type or a bipolar type is selected by the operation mode selection switch 119 according to an electrode in use. The control section built in the high frequency power source 102 recognizes an operation mode set by the operation mode selection switch 119 (S2) and when a set mode is the excision mode, that is when a monopolar or a bipolar type is selected, the control section limits power supplied from the output section to the order of 200 to 300 W as the maximum according to a kind of output set by the output mode setting switch 120 (S7). That is, the power more than 200 to 300 W cannot be set by the output mode setting switch 120 (the power can be set to a magnitude up to the order from 300 W to 200 W as the maximum according to a kind of an output).

After output setting by the front panel is completed, the excision electrode is inserted into the urethra B and the fore-end of the probe 101 is positioned in the vicinity of the prostate A. When the foot switch 118 is stepped down in this state, the control section recognizes the stepping-down (S8) and makes the output section supply high frequency power (S9). At this point, not only does the output section supply high frequency power only during a time when the foot switch 118 is kept stepped down, which is different from a time when the heating is effected (S10, S12), but when the output is continued for a 60 sec, the control section judges the output continuation as abnormality and stops high frequency output (S11, S12).

As described above, according to the high frequency treatment apparatus of the embodiment, since the two electrodes are employed and not only the fore-ends of the electrodes 109, 110 each are forked in two ways, but high frequency power is alternately supplied to the electrodes 109, 110, the prostate A can be heated in a uniform manner across a very large extent without any reduction in high frequency current density. Accordingly, paracentesis into an organism by the electrodes 109, 110 is not necessary to be repeated and a damage to a tunica mucosa of the urethra can be suppressed to the minimum. Besides, according to the high frequency treatment apparatus, operations of heating and excision can both be performed with provision of a single high frequency power source 102.

Figure 18:
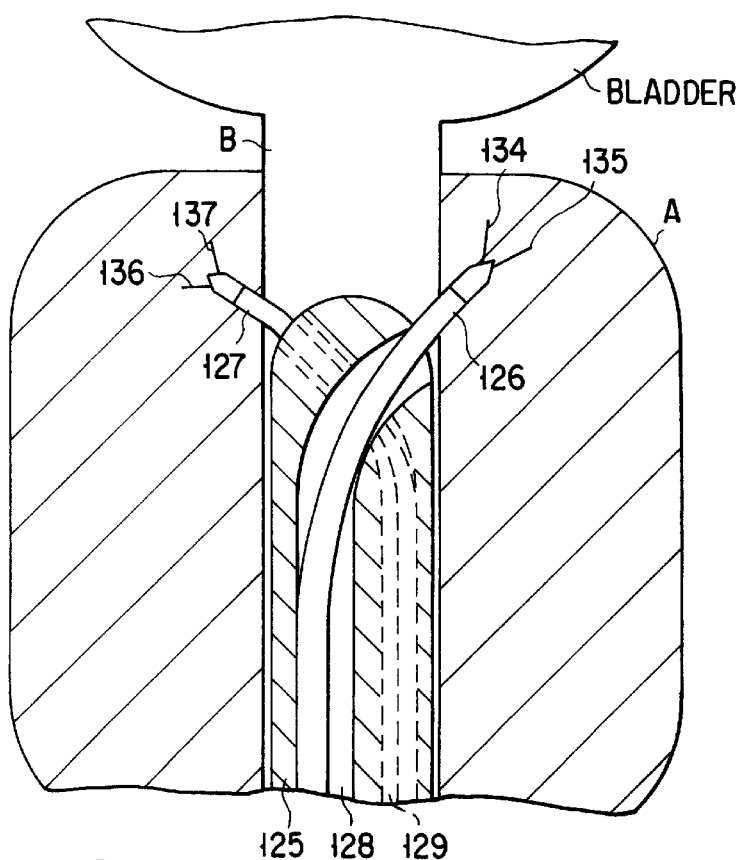
FIG. 18 is a sectional view of the fore-end of a probe constituting the high frequency treatment apparatus according to a third embodiment of the present invention.
Figure 19:
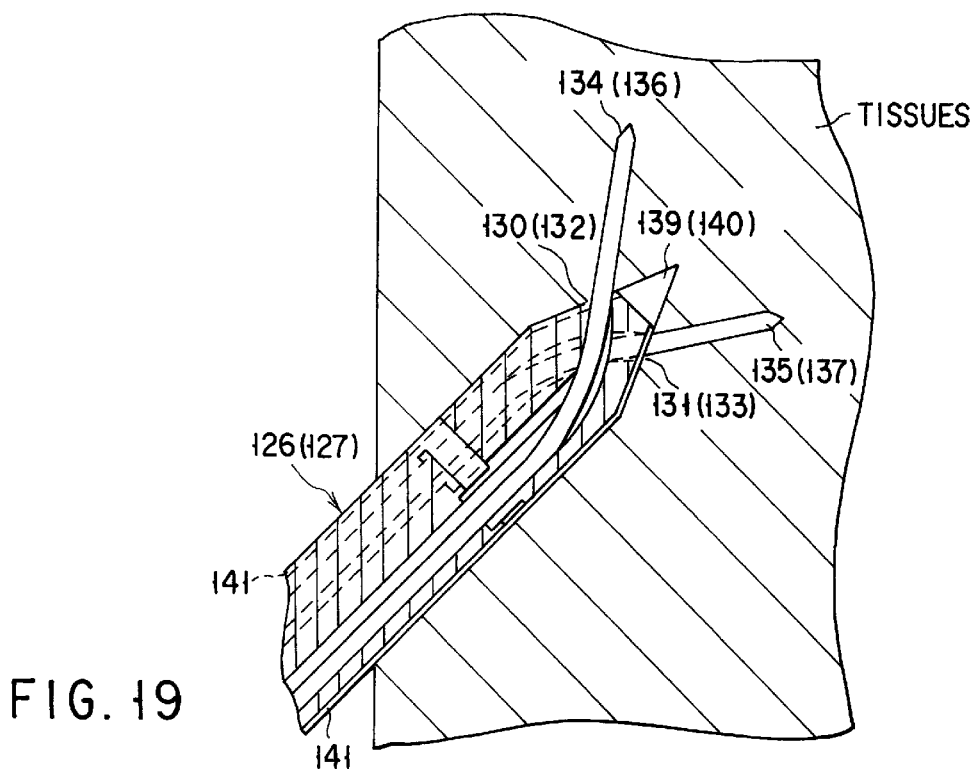
FIG. 19 is a sectional view showing a state in which a sheath protruding from the probe of FIG. 18 performs paracentesis into prostate tissue.
Figure 20:
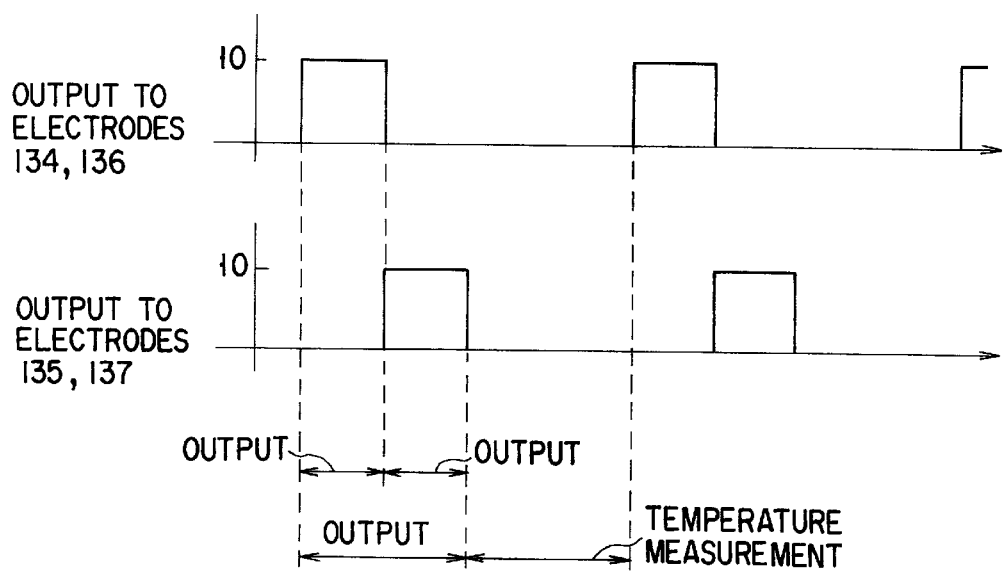
FIG. 20 is a timing chart of high frequency output and temperature measurement.

FIGS. 18 to 20 show the third embodiment of the present invention. A high frequency treatment apparatus of the embodiment comprises: a probe 125 as a treatment tool shown in FIG. 18; and a high frequency power source which is almost same as the second embodiment. The probe 125 is electrically connected to the high frequency power source through an electrode cable.

As shown in FIG. 18, the probe 125 has two channels 128, 129. The fore-ends of the channels 128, 129 extend along a direction inclined to the central axis of the probe 125 and have openings at the fore-end of the probe 125. Especially in the embodiment, the channels 128, 129 respectively have the openings in the opposed sides with respect to a plane including the central axis of the probe 125. Sheaths 126, 127 formed of insulating material are respectively inserted in the insides of the channels 128, 129 in a forward/backward movable manner. The fore-ends of the sheaths 126, 127 each have a sharp needle like shape. An operation switch for operating the sheaths 126, 127 so as to move forward or backward the sheaths 126, 127 in the respective channels 128, 129 independently is provided in the proximal side of the probe 125.

As shown in FIG. 19, the sheath 126 (127) has two channels 130, 131 (132, 133). The fore-ends of the channels 130, 131 (132, 133) extend along a direction inclined to the central axis of the sheath 126 (127) and has an opening at the fore-end of the sheath 126 (127). Especially in the embodiment, the channels 130, 131 (132,133) respectively have openings in the opposed sides with respect to a plane including the central axis of the sheath 126 (127). Electrodes 134, 135 (136, 137) made of conductive material are respec-tively inserted in the insides of the channels 130, 131 (132, 133) in a forward/backward movable manner. The fore-ends of the electrodes 134, 135 (136, 137) each have a sharp needle like shape. The electrodes 134, 135 (136, 137) are operated so as to be independently moved forward or backward in the insides of the channels 130, 131 (132, 133) by an operation switch, not shown.

Two power supply lines extending from the electrodes 134, 135 extend through the insides of the sheath 126 and the electrode cable and when the electrode cable is connected to a heating electrode connection port of the high frequency power source (see FIG. 15), the two power supply lines are respectively connected to corresponding high frequency output terminals of the heating electrode connection port. The two power supply lines extending from the electrodes 136, 137, too, extend through the insides of the sheath 127 and the electrode cable and when the electrode cable is connected to the heating electrode connection port of the high frequency power source, the two power supply lines are respectively connected to other corresponding high frequency output terminals of the heating electrode connection port.

The sheath 126 (127) can freely be bent across almost the entire length except the fore-end. A temperature sensor 139 (140) is provided at the fore-end of the sheath 126 (127). A signal line 141 extending from the temperature sensor 139 (140) extends through the insides of the sheath 126 (127) and the electrode cable and when the electrode cable is connected to the heating electrode connection port of the high frequency power source, the signal line 141 is connected to the temperature measurement terminal of the heating electrode connection port. In the mean time, the other construction is same as the second embodiment.

Then, the case where a prostate treatment is performed using the high frequency treatment apparatus with the above construction will be described.

When the prostate is subjected to heat treatment, as in the second embodiment, an opposite electrode plate is mounted on a patient and the opposite electrode plate, the probe 125 and the foot switch are connected to the high frequency power source. Then, switches on the front panel of the high frequency power source are operated and output setting is performed as in the second embodiment. In the mean time, output limitation and the like by a control section are performed in a similar way to the second embodiment.

After the output setting by the front panel is completed, the probe 125 is inserted into the urethra B and the fore-end of the probe 125 is positioned in the vicinity of the prostate A. The sheaths 126, 127 are protruded from the openings of the channels 128, 129 to perform paracentesis into the prostate A by operating the switch provided in the proximal side of the probe 125. Subsequently to this, the electrodes 134, 135 (136, 137) of the sheaths 126 (127) are protruded from the openings of the channels 130, 131 (132, 133) to perform paracentesis into the prostate A by operating the switch.

The foot switch is once stepped down in this state (thereafter the stepping-down pressure may be released), the control section recognizes the stepping-down and makes the output section supply high frequency power. At this point, the control section sequentially makes the output section supply power indicated on the output setting indicator to the high frequency terminals (accordingly, to the electrodes 134, 135, 136, 137) in the timing shown in FIG. 20. That is, the control section sequentially supplies power to the electrodes 134, 135, 136, 137 through the output section and thereafter stops output for a certain period, during which output stoppage the control section detects (measures) temperature of a treatment site while taking in signals from the temperature sensors 139, 140. In the mean time, operation control thereafter in the heating mode and operation control in the dissection mode are same as the second embodiment.

As described above, according to the high frequency treatment apparatus of the embodiment, since the four electrodes 134, 135, 136, 137 are employed and not only do the electrodes 134, 135, 136, 137 perform paracentesis into the prostate in a branched and diffused manner together with the sheaths 126, 127, but high frequency power sequentially supplied to the electrodes 134, 135, 136, 137, the prostate A can at a time be heated across a large extent in a uniform manner without any reduction in a high frequency current density. Therefore, repetition of paracentesis into an organism by the electrodes 134, 135, 136, 137 is unnecessary and besides injuries in the tunica mucosa of the urethra can be suppressed to the minimum. That is, a large extent can be heated with a small paracentesis injury.

In the high frequency treatment apparatus of the embodiment, high frequency output is not effected in temperature measurement. Therefore, temperature measurement is not affected by high frequency (noise). For this reason, addition of a circuit for noise elimination is unnecessary, which simplifies a structure of the whole circuitry.

Figure 21:
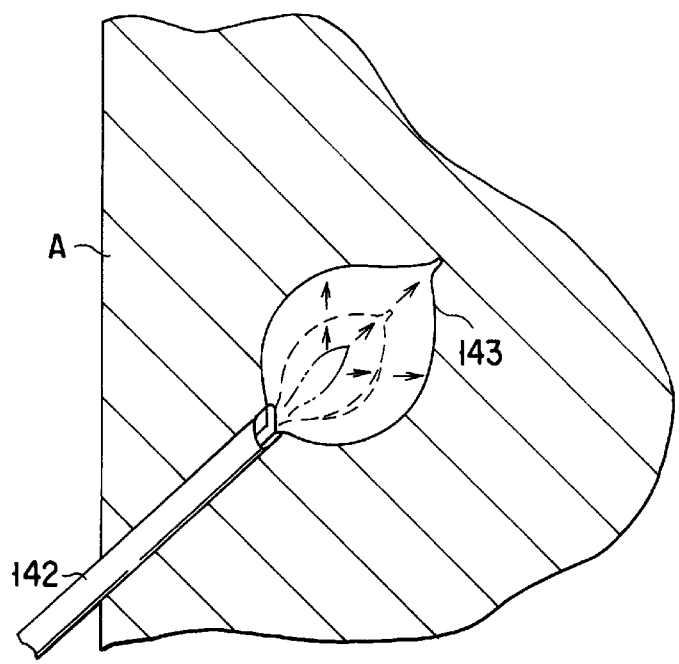
FIG. 21 is a sectional view according to a modification of the third embodiment.

Besides, in the third embodiment, the sheath 126 (127) and the electrodes 134, 135(136, 137) may be constructed as shown in FIG. 21. That is, an electrode having a loop-like shape is accommodated in a cylindrical sheath 142 in a freely forward and backward movable manner. In this case, the electrode 143 is given a habit that when the electrode 143 is protruded from the sheath 142, the electrode 143 is expanded. In this structure, when the loop-like electrode 143 performs paracentesis into the prostate A and a current is made to flow through the electrode 143, tissues of the prostate is, for example, dissected by the electrode 143. As the dissection progresses, the electrode 143 assumes its expanded state drawn by a solid line in the figure starting from a contracted state drawn by a dotted line as shown in the figure because of its expansion habit.

Figure 22B:
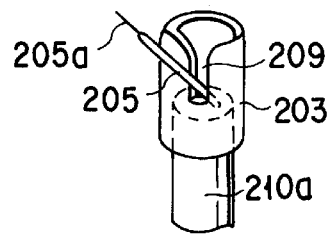
FIG. 22B is an enlarged view showing the fore-end of the high frequency treatment apparatus of FIG. 22A.
Figure 22A:
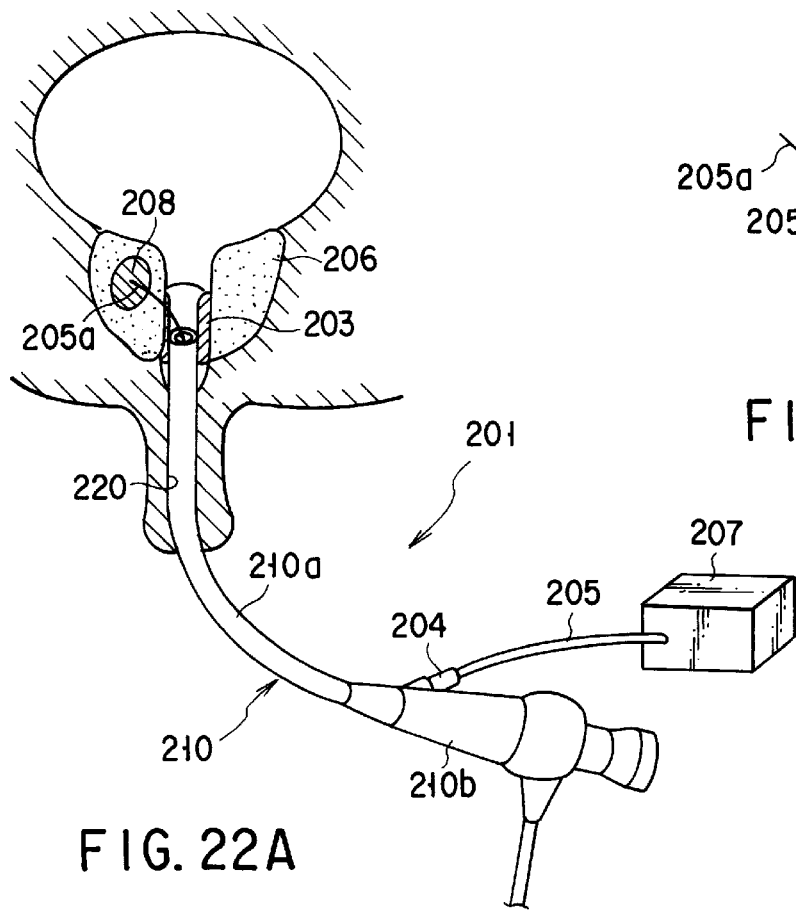
FIG. 22A is an overall construction of a high frequency treatment apparatus according to a fourth embodiment of the present invention.

FIGS. 22A and 22B show the fourth embodiment of the present invention. As shown in FIG. 22A, a high frequency treatment apparatus according to the embodiment is a prostate treatment apparatus 201, which comprises: a flexible endoscope 210 having an insertion section 210a which can be inserted into urethra 220; and an operative tool 205 as a treatment tool, which is connected to an energy generator 207, and which can be inserted through the insertion section 210a of the endoscope 210. The energy generation means 207 is constituted of a high frequency power generator (200 KHz to 800 KHz) as a high frequency generation section. The energy generation means 207 may be constituted of a microwave generator (100 MHz to 3000 MHz) or the like.

The endoscope 210 comprises: the insertion section 210a; an operation section 210b connected to the base end of the insertion section 210a; and the body thereof. A channel (not shown) is formed in the insertion section 210a across the entire length thereof. An operative tool introducing port 204 which communicates with the channel is provided in the operation section 210b. On the other hand, the operative tool 205 has an operative section 205a, which has a needle-like shape, and which actually performs paracentesis into the prostate 206, at its fore-end. The fore-end side of the operative tool 205 has a bending habit so that the needle-like operative section 205a can easily performs paracentesis into a desired site of the prostate 206 which is located to the side of the urethra 220.

Besides, a cylindrical cover member 203 with an opening at its fore-end is mounted, for example in a mountable and demountable manner, at the fore-end of the insertion section 210a of the endoscope 210. The cover member 203 has a length to secure a good visual field toward the forward side of the insertion section 210a by pressing away prostate tissues which covers the fore-end side of the insertion section 210a when being inserted into the urethra 220. As in detail shown in FIG. 22B, a cut-away 209 extending across a predetermined length from the brim of the fore-end opening is provided in the side surface of the cover member 203. A width of the cut-way 209 is set to a size through which the operative tool 205 can pass.

When a treatment of the prostatomegaly is performed using the prostate treatment apparatus 201 with the above described construction, not only is the insertion section 210a of the endoscope 210 inserted into the urethra 220, but the operative tool 205 which is connected to the energy generation means 207 through the operative tool introducing port 204 provided in the operation section 210b of the endoscope 210 is inserted into the channel of the insertion section 210a. Then, when, as shown in FIG. 22A, the fore-end of the insertion section 210a is positioned in the vicinity of a diseased part 208 of the prostate 206, the needlelike operative section 205a of the operative tool 205 is projected from the fore-end of the insertion section 210a and the operative section 205a is forced to penetrate into the prostate 206 up to the diseased part 208 thereof under observation through the endoscope 210.

In this case, the operative section 205a is guided through the cut-way of the cover member 203 by operation at the proximal side so as to perform paracentesis into the diseased part 208 of the prostate 206 which is located to the side of the urethra 206 while using the bending habit of the fore-end side of the operative tool 205 (see FIG. 22B). In the operation, the visual field toward the forward side of the insertion section 210a is favorably secured by the cover member 203 which presses away the prostate tissues covering the fore-end side of the insertion section 210a.

When it has been recognized under observation in a good visual field by the endoscope 210 that the operative section 205a is sure to penetrate into the diseased part 208 of the prostate 206, a high frequency current, for example, is made to flow into the diseased part 205a from the energy generation means 207 and the diseased part 208 of the prostate 206 in which the operative section 205a is positioned is heated to be cauterized. With this cauterization, the diseased part is necrotized and absorbed through separation over a long time, so that the hypertrophy of the prostate 206 is eliminated and the urethra 220 comes to restore an effective channel. High frequency control in this case is performed in a similar way to the first embodiment. That is, in the embodiment, a setting section for setting a treatment mode (control mode) is provided and the maximal value of high frequency output is confined to be equal to or less than a predetermined value according to a set treatment mode (heating, coagulation, dissection and the like).

As described above, since the prostate treatment apparatus 201 of the embodiment presses away the prostate tissues which cover the fore-end side of the insertion section 210a by the cover member 203 mounted at the fore-end of the insertion section 210a of the endoscope 210 and thereby, a visual field toward the forward side of the insertion section 210a can favorably be secured, paracentesis into the treatment site, which is a target, by the operative section 205a of the operative tool 205 can be performed with certainty and accuracy.

Besides, since the prostate treatment apparatus 201 of the embodiment has the bending habit at the fore-end side of the operative tool 205, paracentesis into a diseased part of the prostate which is located to the side of the urethra 220 can easily be performed without any bending the urethra 220. Therefore, heating of a deep site of the prostate 206 can be performed without any physical pain felt by a patient.

While, in the embodiment, easy paracentesis by the needle-like operative section 205a into a desired site in the prostate 206 which is positioned to the side of the urethra 220 can easily be effected by giving a bending habit to the fore-end side of the operative tool 205, a rise table which can rise and fall is provided at the fore-end side of the channel of the insertion section 210a of the endoscope 210 and, with the help of this rise table, the fore-end side of the operative tool 205 may be guided to the diseased part 208 of the prostate 206 which is positioned to the side of the urethra 220. In this case, a direction of the opening at the fore-end side of the channel of the endoscope 210 may be directed toward the diseased part side in advance. Besides, in the embodiment, the cover member 203 may be formed of a transparent material. When the cover member 203 is formed of a transparent material, observation by the endoscope 210 in the urethra 220 can be secured even without an opening at the fore-end of the cover member 203.

Figure 23A:
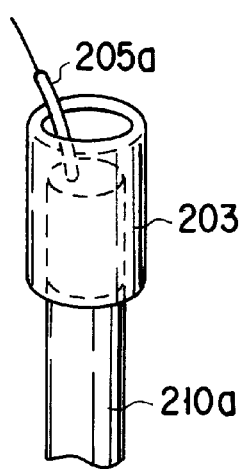
FIG. 23A is an enlarged view of a main part of a high frequency treatment apparatus according to a fifth embodiment of the present invention.

FIG. 23A shows the fifth embodiment of the present invention. While, in the fourth embodiment, the cut-away 209 is formed in the cover member 203 in order to protrude the operative section 205a toward the side, in the embodiment no cut-away is formed in a cover member 203. In the mean time, the other construction is same as the fourth embodiment. With such a construction in use, an operative section 205a is protruded into the urethra 220 through an opening at the fore-end of the cover member 203 and paracentesis into a diseased part 208 of the prostate 206 which is positioned to the side of the urethra 220 is effected with the help of a bending habit of the fore-end side of an operative tool 205. It is needless to say that, in this case, too, a visual field toward the fore-end side of an insertion section 210a is favorably secured by the cover member 203.

Figure 23B:
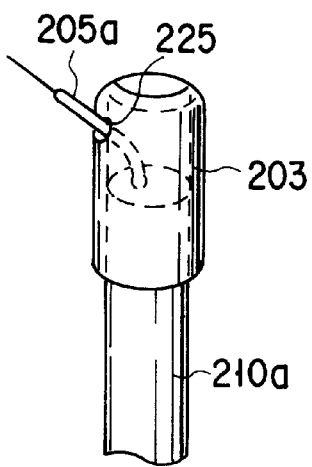
FIG. 23B is an enlarged view of a main part of a high frequency treatment apparatus according to a sixth embodiment of the present invention.

FIG. 23B shows the sixth embodiment of the present invention. In the embodiment, a hole 225 through which an operative tool 205 can pass is formed in the side surface of a cover member 203. The other construction is same as the fourth embodiment. With such a construction in use, an operative section 205a is made to pass through the hole 225 of the cover member 203 taking advantage of a bending habit of the fore-end side of the operative tool 205 and paracentesis into a diseased part 208 of the prostate 206 which is positioned to the side of the urethra 220 by the operative section 205a is effected through the hole 225. It is also needless to say that, in this case, too, a visual field toward the fore-end side of an insertion section 210a is favorably secured by the cover member 203.

Figure 24:
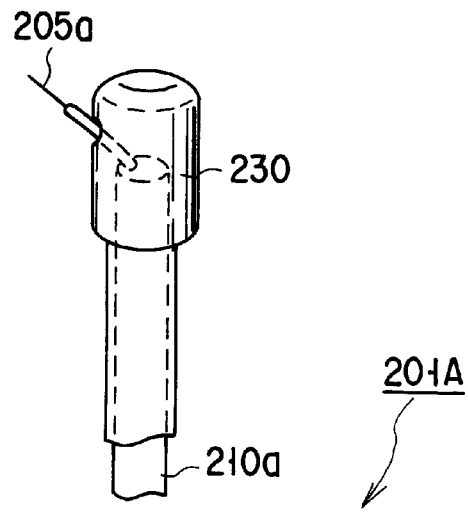
FIG. 24 is a diagram of an overall construction of a high frequency treatment apparatus according to a seventh embodiment of the present invention.
Figure 24:
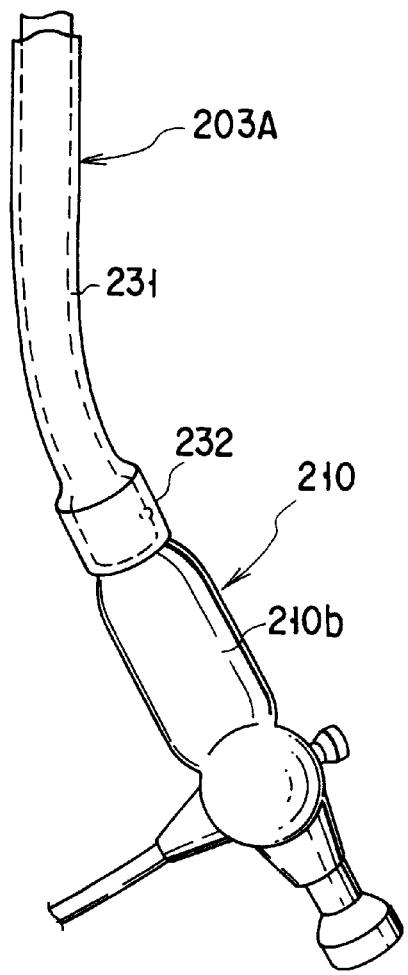

FIG. 24 shows the seventh embodiment of the present invention. A prostate treatment apparatus 201A of the embodiment has the same endoscope 210 as that of the fourth embodiment and a cover member 203A. The cover member 203A comprises: a tissue pressing-away section 230 for pressing away prostate tissues, which is located to the fore-end side of an insertion section 210a ahead of the insertion section 210a thereof; a sheath section 231 through which the insertion section 210a of the endoscope 210 can be inserted; and a fixation section 232 which is fixedly mounted to an operation section 210b of the endoscope 210. The cover member 203A has positioning means for maintaining a distance between the fore-end of a tissue pressing-away section 230 and the fore-end of insertion section 210a at a predetermined distance (a distance with which a sufficient visual field toward the forward side of the insertion section 210a is secured) by positioning the fore-end of the insertion section 210a of the endoscope 210 which is inserted into a sheath section 231. The positioning means is constituted of a protrusion which is provided on the inner side surface of the sheath 231 or the tissue pressing-away section 230, and which can be hit by the fore-end of the insertion section 210a. Accordingly, with such a construction, too, a similar effect to the fourth embodiment can be attained.

Figures 25A, 25B:
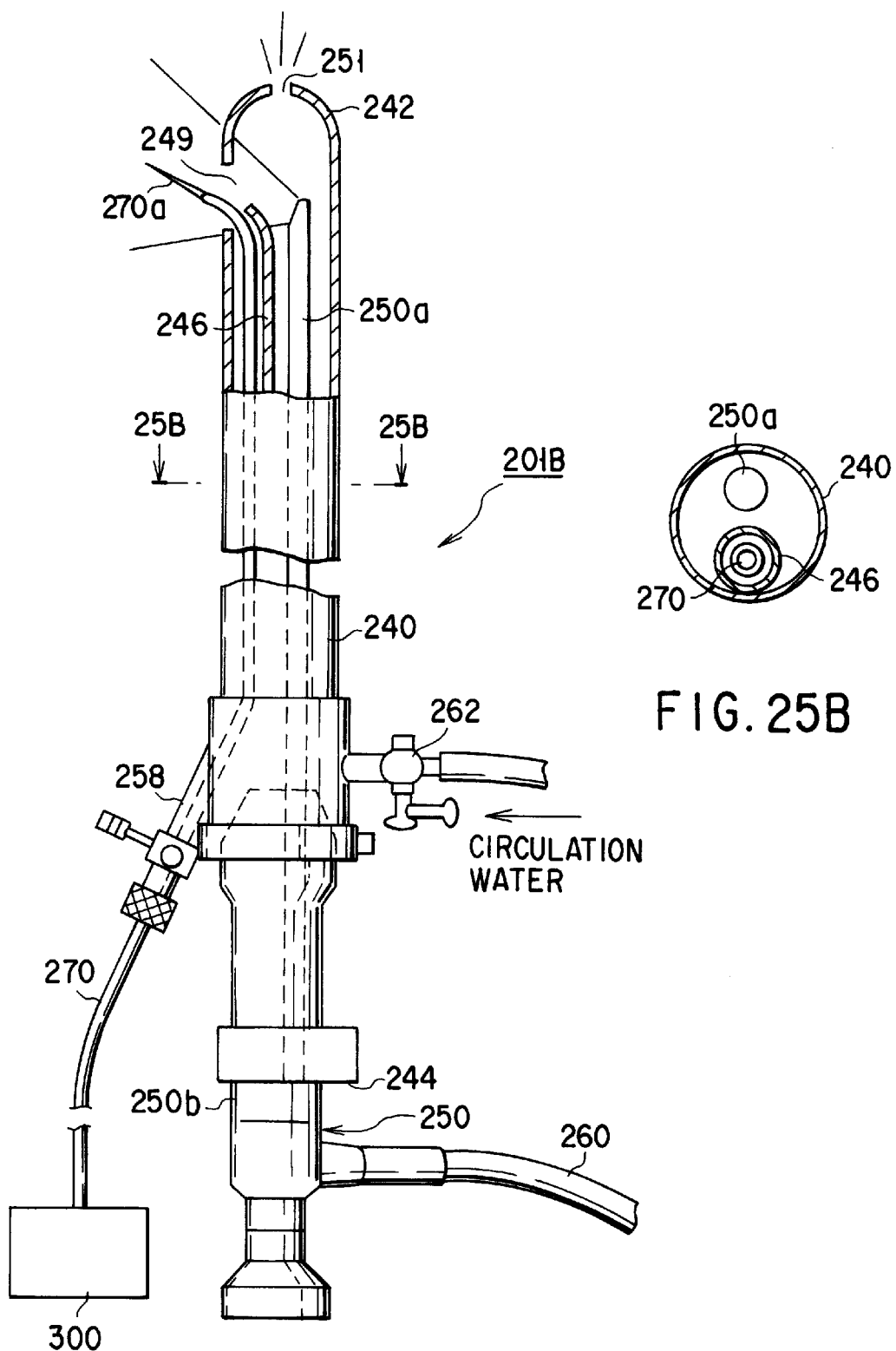
FIG. 25A is a diagram of an overall construction of a high frequency treatment apparatus according to a eighth embodiment of the present invention.
FIG. 25B is a sectional view taken on line 25B—25B of FIG. 25A.

FIGS. 25A and 25B show the eighth embodiment of the present invention. A prostate treatment apparatus 201B of the embodiment has a long sheath member 240 corresponding to the cover member 203A of the seventh embodiment and an optical view tube (endoscope) 250 which is inserted in the sheath member 240. The fore-end of the sheath member 240 is closed by a spherical surface 242. A small hole 251 is formed in the spherical surface 242. An opening section 244 which allows insertion and pulling off of the optical view tube 250 facing the inside of the sheath member 240 is formed at the base end of the sheath member 240. The sheath member 240 is provided with a cock section 262 for guiding a circulation liquid into the sheath member 240 and a forceps port 258 for inserting a high frequency electrode 270 as a treatment tool into the sheath member 240. The forceps port 258 is formed in the sheath member 240 and communicates with a channel 246 for guiding the high frequency electrode 270. The fore-end side of the channel 246 is bent being directed to the side and an opening 249 is formed in the peripheral side surface of the sheath member 240 at an position opposed to the fore-end of the bent channel 246.

The body of the optical view tube 250 comprises an insertion section 250a which can be inserted into the urethra and an operation section 250b. A light guide fiber 260 which is connected to an optical source apparatus, not shown, is connected to the operation section 250b. A high frequency electrode 270 has a needle-like operative section 270a, which performs paracentesis into the prostate, at the fore-end thereof. Besides, the high frequency electrode 270 is connected to a high frequency power source 300 as a high frequency generation section and thereby a high frequency current is supplied to the operative section 270a.

The sheath member 240 has positioning means for maintaining a distance between the spherical surface 242 and the fore-end of the insertion section 250a at a predetermined distance (a distance with which a sufficient visual field toward the forward side of the insertion section 205a is secured) by positioning the fore-end of the insertion section 250a of the optical view tube 250 which is inserted into the sheath member 240. The positioning means is constituted, for example, of a protrusion which is provided on the inner side surface of the sheath member 240, and which can be hit by the fore-end of the insertion section 250a. The optical view tube 250 is positioned so that the observation window is opposed to the opening 249 in the state in which the fore-end of the insertion section 250a is positioned by the positioning means.

The prostate treatment apparatus 201B with such a construction is used in a state in which the high frequency electrode 270 and the optical view tube 250 are mounted to the sheath member 240. In this case, the operative section 270a of the high frequency electrode 270 which is inserted into the channel 246 of the sheath member 240 through the forceps port 258 can protrude to the side by guidance of the fore-end side of the bent channel 246 through the opening 249. In the optical view tube 250, not only is the fore-end of the insertion section 250a separated from the fore-end (spherical surface 242) of the sheath member 240 by a predetermined distance, but the observation window is oppositely positioned to the opening 249, by the positioning means.

In such an arrangement condition (the operative section 270a of the electrode 270 is accommodated in the channel 246), the sheath member 240 is inserted through the urethra up to a position of the prostate and when the prostate is recognized with the optical view tube 250, the operative section 270a of the high frequency electrode 270 is protruded to the side through the opening 249 to penetrate into the prostate to reach a disease part. When a high frequency current is supplied to the operative section 270a from the high frequency power source 300 in that state, the diseased part of the prostate is heated and cauterized. It is needless to say that during the operation, the visual field toward the fore-end side of the insertion section 250a can favorably be secured by the sheath member 240. High frequency control in this case is effected in a similar manner to the first embodiment. That is, in the embodiment, a setting section for setting a treatment mode (control mode) is provided and the maximal value of high frequency output is confined to be equal to or less than a predetermined value according to a set treatment mode (heating, coagulation, dissection and the like).

Besides, in such a treatment, when a cleaning liquid (circulation liquid) is introduced into the sheath member 240 through the cock 262, the cleaning liquid flows to the diseased part from the opening 249 of the sheath member 240. Furthermore, a contaminated cleaning liquid can also be sucked through the small hole 251 formed in the spherical surface 242 of the fore-end of the sheath member 240. When an observation range of the optical view tube 250 is of a wide angle or when an area of the opening 249 provided in the sheath member 240 is required to be as small as possible, the peripheral region of the opening 249 may be made of a transparent material.

Figure 26:
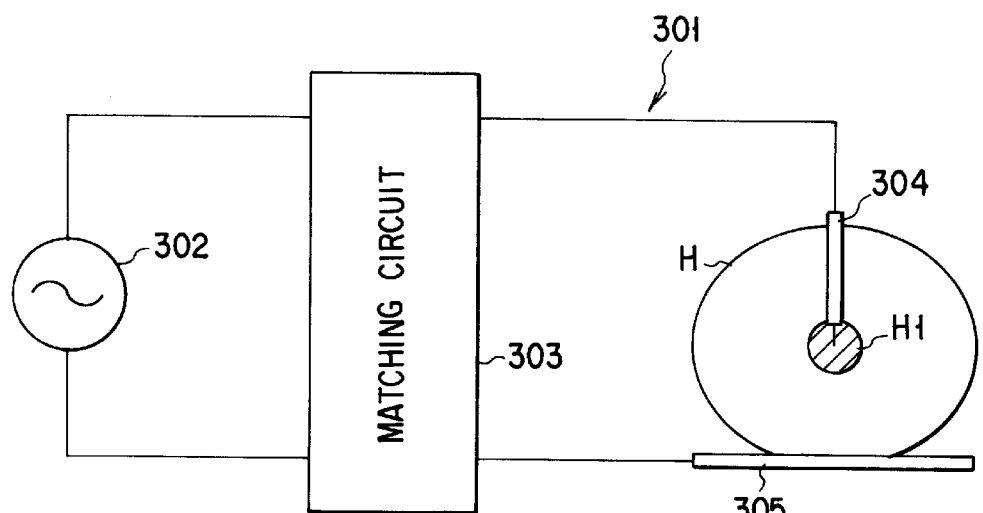
FIG. 26 is a diagram of a schematic construction of a high frequency treatment apparatus according to a ninth embodiment of the present invention.
Figure 27:
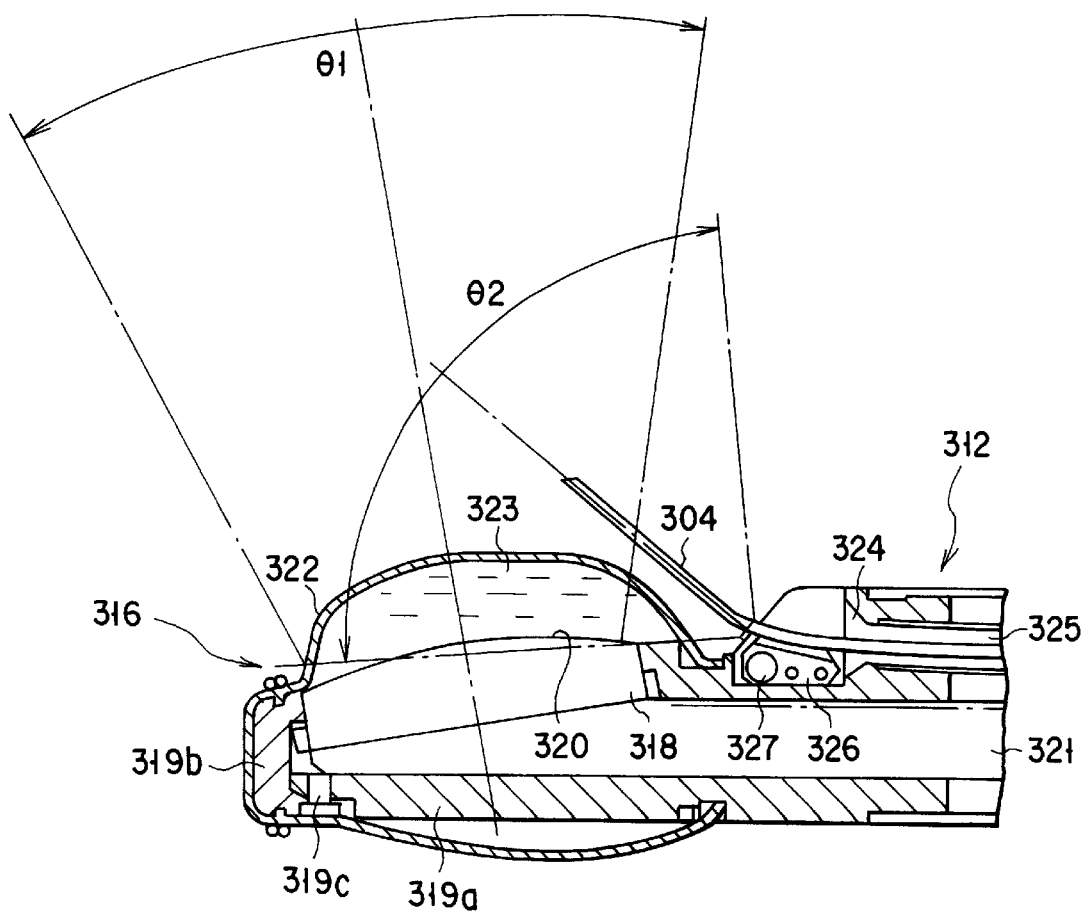
FIG. 27 is a longitudinal sectional view of a fore-end portion of an insertion section of an ultrasonic endoscope.
Figure 28:
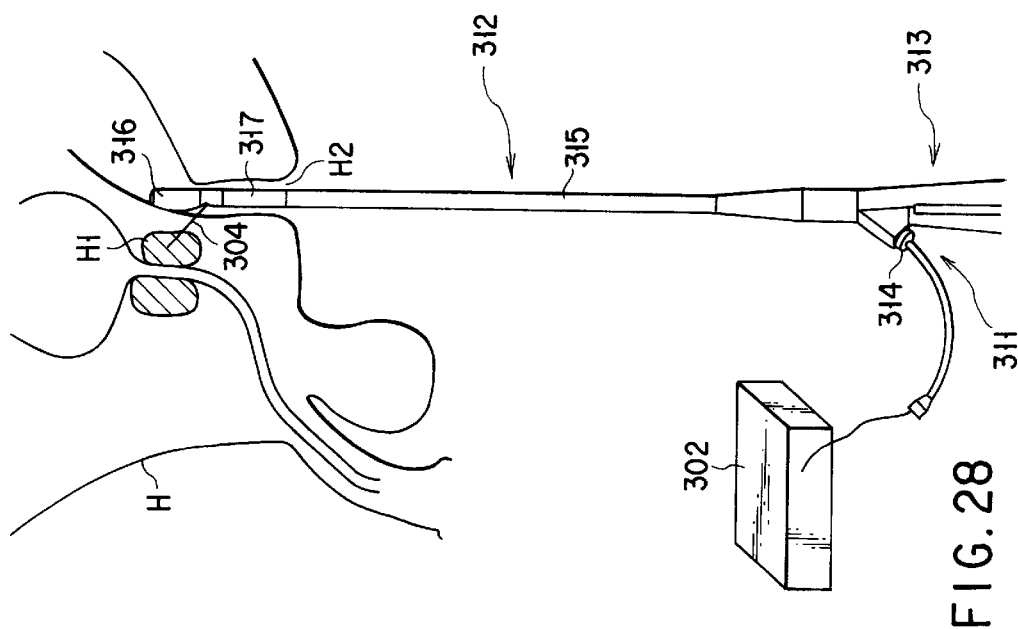
FIG. 28 is a representation showing a state in which the high frequency treatment apparatus of FIG. 26 is in operation.
Figure 30:
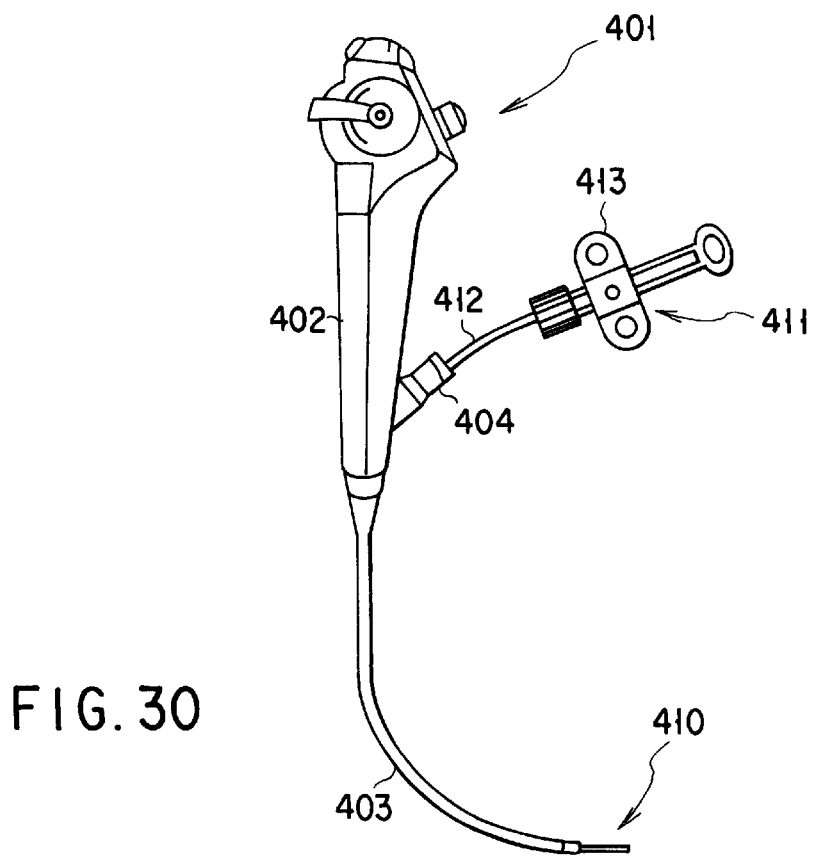
FIG. 30 is a perspective view showing a state in which a treatment tool of a high frequency treatment apparatus according to an eleventh embodiment of the present invention is inserted through an endoscope.

FIGS. 26 to 28 show the ninth embodiment of the present invention. A high frequency treatment apparatus 301 of the embodiment, as shown in FIG. 26, comprises: a high frequency power source 302; matching circuit 303; a penetration electrode (insertion section) 304 as a treatment tool; and an external electrode 305. The high frequency power source 302 is connected to the penetration electrode 304 on the one hand and to the external electrode 305 on the other hand through the matching circuit 303 for matching with an impedance of an organism (patient) H.

The external electrode 305 is arranged at a predetermined position on the outside of the organism H, while the penetration electrode 304 is forced to penetrate into the organism H. A high frequency current flows between the penetration electrode 304 and the external electrode 305 through the matching circuit 303 of the high frequency power source 302. With such construction and operation, a high frequency current is given only to the prostate $H_1$ which is a treatment site of the organism H where a predetermined operation is performed and heating, coagulation, cauterization and the like are performed for the prostate which is an treatment site. The high frequency control in this case is performed in a similar manner to the first embodiment. That is, in the embodiment, a setting section for setting a treatment mode (control mode) is provided and the maximal value of a high frequency output is confined to be equal to or less than a predetermined value according to a set treatment mode (heating, coagulation, dissection and the like).

An ultrasonic endoscope 311 as shown in FIG. 28 as observation means for observing the prostate is provided in the high frequency treatment apparatus 301 of the embodiment. An operation section 313 of the proximal side in the base end portion of a narrow and long insertion section 312 which is inserted into an organism is connected to the ultrasonic endoscope 311. The base end portions of a universal cord, not shown, and an ultrasonic cord, not shown, are connected to the proximal side operation section 313. An endoscope connector, not shown, is connected to the fore-end portion of the universal cord and an ultrasonic connector, not shown, is connected to the fore-end portion of the ultrasonic cord.

The operation section 313 is provided with an operative tool insertion port 314 for an operative tool, degased water and the like, and buttons for gas feed, water feed and the like, not shown. The penetration electrode 304 which is connected to the high frequency power source 302 for the high frequency treatment apparatus 301 is inserted into the operative tool insertion port 314. The insertion section 312 is provided with: a narrow, long flexible section 315; a fore-end structure section 316 which is provided at the farthermost fore-end of the insertion section 312; and a curved section 317 provided between the flexible section 315 and the fore-end structure section 316.

FIG. 27 shows a schematic construction of the fore-end structure section 316 of the insertion section 312. The fore-end structure section 316 is provided with an ultrasonic probe holding section 319 for holding the ultrasonic probe 318. The ultrasonic probe holding section 319 is provided with the holding section body 319a formed in the fore-end structure section 316 and a fore cover 319b provided at the fore-end portion of the holding section body 319a. The fore cover 319b is fixedly connected to the holding section body 319a by a fixation screw 319c and an adhesive with which the interior is filled.

The ultrasonic probe 318 is mounted to the ultrasonic probe holding section 319 in a state in which an ultrasonic wave transmission/reception face 320 thereof is directed to the side. FIG. 27 shows a scanning section of the ultrasonic probe 18, in which $\theta_1$ indicates the scanning section (scanning range) of the ultrasonic probe 318. Besides, the fore-end portions of a plurality of signal cables 321 are connected to the ultrasonic probe 318. The base end portion sides of the signal cables 321 are connected to the ultrasonic connector through an insertion section 312, the operation section 313 and further by way of an ultrasonic cord therefrom. A balloon 322 having a bag-like shape is fixedly provided in the vicinity of the ultrasonic probe 318 so as to cover the ultrasonic wave transmission/reception face 320 of the. ultrasonic probe 318 in a attachable/detachable manner. The fore-end side of the balloon 322 is fixed to the fore cover 319b of the ultrasonic probe holding section 319 with an operative thread or the like. Injection and discharge of degased water 323 can be effected in the balloon 322 through tubes, not shown.

The fore-end structure section 316 of the embodiment has a forceps port 324 provided in the ultrasonic wave transmission/reception face 320 side of the ultrasonic probe 318 backward from the ultrasonic probe 318. The forceps port 324 communicates with the fore-end of a channel 325 for inserting an operative tool, which is arranged almost in parallel to a signal cable 321 in the insertion section 312. The base end portion of the channel 325 for inserting the operative tool communicates with the operative tool inserting port 314. The forceps port 324 is arranged in the rear position of the ultrasonic probe 318 so that the penetration electrode 304 is guided in a freely projectable and withdrawable manner in the scanning section of the ultrasonic probe 318. The penetration electrode 304 of the high frequency treatment apparatus 301 which is inserted into the channel 325 for inserting the operative tool from the operative tool inserting port 314 is guided out to the outside from the forceps port 324 and protruded from the fore-end structure section 316.

Besides, a rise table 326 is disposed at a position facing the forceps port 324 in the outlet side of the forceps port 324. The rise table 326 is mounted to the fore-end structure section 316 in a manner such that the table can be pivoted about a pivotal axis 327. A rise angle $\theta_2$ of the rise table 326 can be adjusted at an arbitrary angle by operation of a rise operation lever or the like of a proximal side operating section 313. Therefore, a guiding-out angle of the penetration electrode 304, which is inserted into the channel 325 for inserting the operative tool, and which is guided out to the outside from the forceps port 324, is adjustable in company with a rise operation of the rise table 326. A rise angle $\theta_2$ of the rise table 326 is set so that the penetration electrode 304 may be positioned in the scanning section 317 of the ultrasonic probe 318. The penetration electrode 304 is forced to penetrate into the prostate $H_1$ of the organism H by way of the channel 325 of the ultrasonic endoscope 311.

Then, operations of the above described construction will be described. When the prostate $H_1$ is treated using the high frequency treatment apparatus of the embodiment, the penetration electrode 4 of the high frequency treatment apparatus 301 is first inserted into the channel 325 of the ultrasonic endoscope 311 through the operative tool insertion port 314 of the ultrasonic endoscope 311 and the fore-end of the electrode 304 is advanced to the position of the rise table 326. In this state, the ultrasonic endoscope 311 is inserted from the rectum $H_2$ side and advanced to the position of the prostate $H_1$, and there, the prostate $H_1$ is observed by ultrasonic echo. The observation range in this case is the scanning section $\theta_1$ of the ultrasonic probe 318 shown in FIG. 27 and an operative site is specified by an ultrasonic image which is attained from the this range.

The penetration electrode 304 is further advanced in the state in which the operative site has been specified by the ultrasonic image and the rise table 326 is adjusted so that the fore-end of the electrode 304 is placed at the specified site. The rise angle $\theta_2$ which is a pivoting angle range of the rise table 326 crosses the scanning section $\theta_1$ of the ultrasonic probe 318. Accordingly, a position of the penetration electrode 304 can be confirmed by the ultrasonic endoscope 311 all the time. Thereafter, the penetration electrode 304 cauterizes the specified site and when another site is subsequently cauterized, the same procedures can be applied. The penetration electrode 304 is drawn out after the treatment of all sites is completed, whereby the treatment operation is terminated.

Therefore, the above construction has the following effects. That is, in the embodiment, when treatment of the prostate is performed, the penetration electrode 304 of the high frequency treatment apparatus 301 which is used for heating the prostate $H_1$ is inserted into the channel 325 of the ultrasonic endoscope 311 with which the prostate $H_1$ can be observed and in this state, a ultrasonic endoscope 311 is inserted from the rectum $H_2$ side. Subsequently, the prostate $H_1$ is observed by the ultrasonic endoscope 311 and when a site to be dissected of the prostate $H_1$ is confirmed, the penetration electrode 304 of the high frequency treatment apparatus 301 is advanced to the dissection site, paracentesis into the site is performed there and cauterization can be started. Therefore, since the prostate $H_1$ can be dissected while observing the prostate $H_1$, treatment can for certain be performed with no error in locating the treatment site. Besides, since the ultrasonic endoscope 311 which is an observation apparatus is inserted into the body from the rectum $H_2$ side, a pain felt by a patient can be reduced as compared with insertion from the urethra side.

Figure 29:
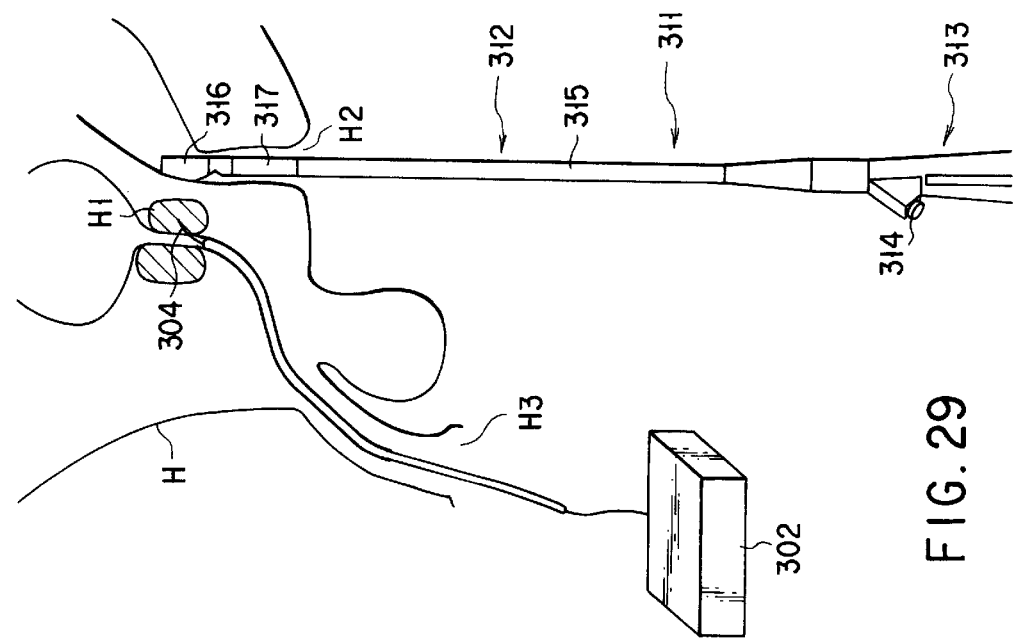
FIG. 29 is a representation showing a state in which a high frequency treatment according to a tenth embodiment of the present invention is in operation.

FIG. 29 shows the tenth embodiment of the present invention. In the embodiment, the construction of the high frequency treatment apparatus of he ninth embodiment (FIGS. 26 to 27) is modified in the following way. That is, not only is an ordinary ultrasonic endoscope 311 inserted from the rectum $H_2$ side of a patient, but the penetration electrode 304 of the high frequency treatment apparatus 301 is inserted from the urethra H3 side and the penetration electrode 304 is forced to penetrate into the prostate $H_1$. Then, since confirmation of the prostate $H_1$ and confirmation of the penetration electrode 304 can simultaneously be effected in the embodiment, too, a similar effect to the ninth embodiment can be attained. In the mean time, while, in the above described embodiment, an apparatus by which the prostate $H_1$ is treated by high frequency is shown, micro waves or a thermotherapy tool can substitute for the penetration electrode 304 of the high frequency treatment apparatus 301.

FIGS. 30 to 35 show the eleventh embodiment of the present invention. A high frequency treatment apparatus of the embodiment has an endoscope 401 of a flexible type shown in FIG. 30. An operation section 402 of the endoscope 401 communicates with a flexible insertion section 403 and a channel for inserting an operative tool is formed from an operative tool inserting port 404 of the operation section 402 to the fore-end of the insertion section 403 in the endoscope 401. A high frequency treatment operative tool 411 as a treatment tool according to the embodiment is inserted into the operative tool inserting channel.

Figure 31:
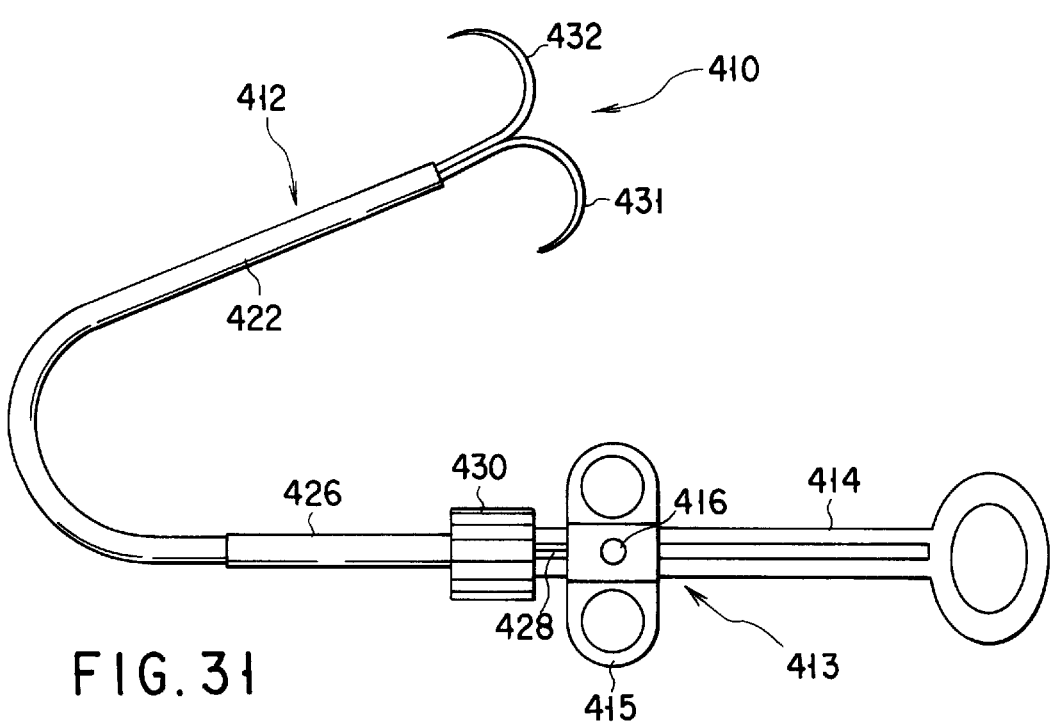
FIG. 31 is an overall view of the treatment tool of FIG. 30.

The high frequency treatment operative tool 411, as shown in FIG. 31, is constructed of: a sheath section 412; and an operation section 413 which is connected to the proximal end of the sheath section 412 in a freely attachable/detachable manner. The operation section 413 comprises: a handle body 414 having an electrically insulating property, which is the body portion; and a slider 415 having electrically insulating property, which moves forward and backward on the handle body 414, and which is used for moving a needle-like electrode section 410. A power supply terminal 416 for connecting an external high frequency power source apparatus (high frequency generation section) thereto is provided on the slider 415. The external high frequency power source apparatus, also not shown, is connected to the power supply terminal 416 through a power source cord, not shown, during a working time.

Figure 32:
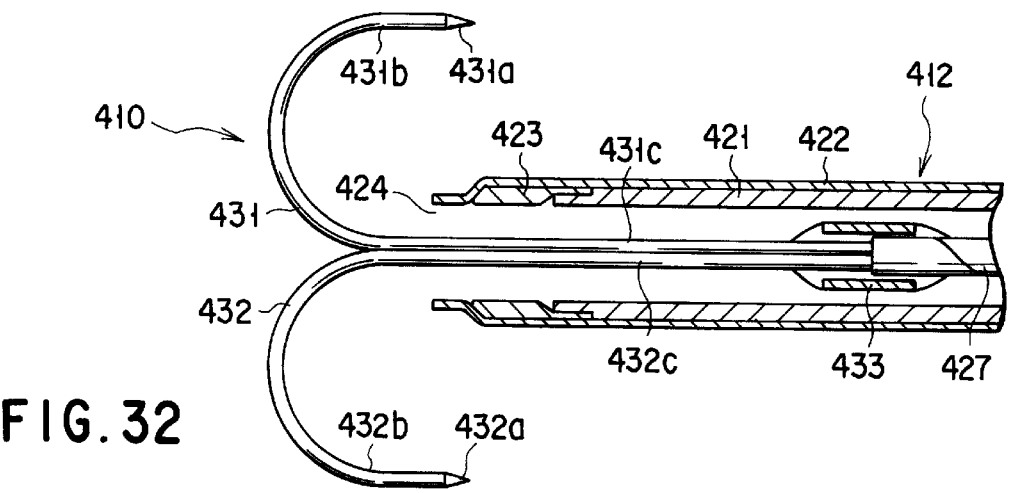
FIG. 32 is a longitudinal sectional view of a fore-end portion of the treatment tool of FIG. 30 showing a state in which a needle like electrode section is protruded from the fore-end of a sheath.

The sheath section 412, as shown in FIG. 32, has a multiple tube structure that is constructed of an inner sheath 421 having flexibility made from a metallic tight-sealed coil and an outer sheath 422 having flexibility and electrically insulating property, which covers the inner sheath 421, and a fore-end tip 423 concentrically arranged is connected to the fore-end portion of the inner sheath 421. The fore-end of the outer sheath 422 protrudes from the fore-end tip 423 toward the fore-end side and contracted in diameter, and a fore-end opening 424 is formed at the protruding portion having a smaller diameter of the outer sheath 422.

Figure 33:
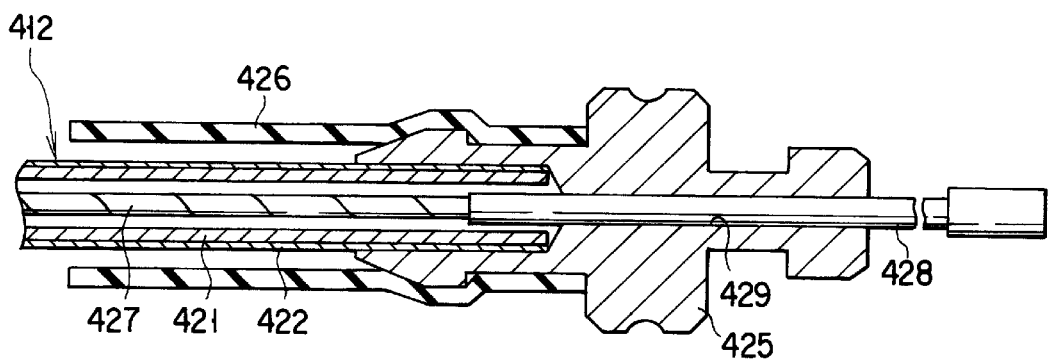
FIG. 33 is a longitudinal sectional view of a proximal portion of a sheath section of the treatment tool of FIG. 30.

As shown in FIG. 33, a connection member 425 for connecting the sheath section 412 to the handle body 414 of the operation section 413 is connected to the proximal side end portion of the sheath section 412. The connection member 425 is fixedly mounted to the proximal end portion of the sheath section 412 while the proximal side end portion of a folding-fixation tube 426 which, in an engaging manner, covers the proximal end portion of the sheath section 412 is attached to the proximal end portion of the sheath section 412 in an engaging manner. A guide hole 429 through which a conductive operation pipe 428 which is connected to a conductive operating wire 427 communicating with a needle-like electrode 410, described later, is inserted in a freely slidable manner is formed in the connection member 425. The operation pipe 428 is electrically conductive with the power supply terminal 416. The operation pipe 428 is connected to the slider 415 in a freely demountable manner. The connection member 425 of the sheath section 412 is connected to the handle body 414 of the operation section 413 in a freely mountable and demountable manner by a connection ring 430 (see FIG. 31).

Figure 34:
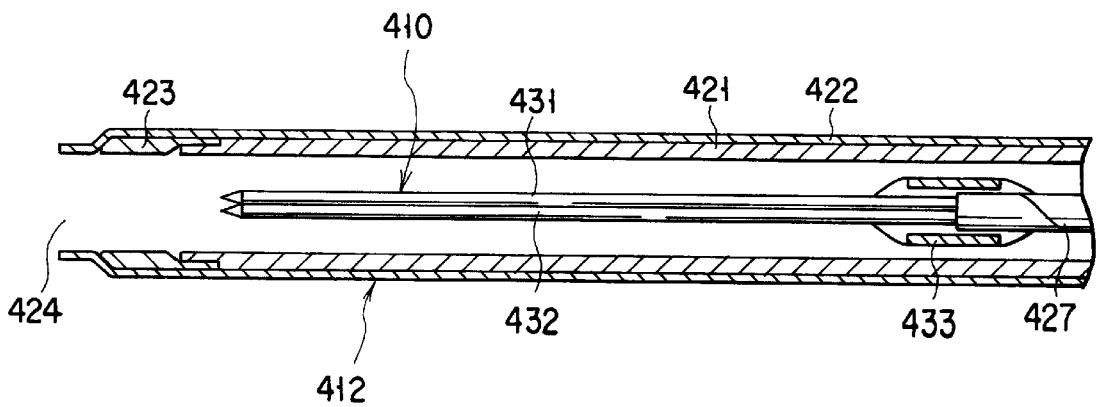
FIG. 34 is a longitudinal sectional view of a fore-end portion of the treatment tool of FIG. 30 showing a state in which a needle like electrode section is withdrawn in a sheath.

The needle-like electrode 410 is constructed of a pair of needle-like electrodes 431, 432 as shown in FIGS. 32 and 34, and the fore-end portions of the needle-like electrodes 431, 432 each are of a sharp needle-tip portion 431a, 432a. The base ends of the needle-like electrodes 431, 432 are connected to the fore-end of the operation wire 427 using a pipe 433, for example, by soldering. The pair of needle-like electrodes 431, 432 can be moved in the sheath section 412 together with the operation wire 427 forward and backward. The needle-like electrodes 431, 432 are made of a conductive material and have flexibility and elasticity. When the electrodes 431, 432 are accommodated in the sheath section 412 while being withdrawn as schematically shown in FIG. 34, they show a state of having an almost straight shape by being restricted with the inner surface of the sheath section 412 and on the other hand, as the fore-end portions of the needle-like electrodes 431, 432 are projected from the fore-end opening 424 of the sheath section 412, the fore-end portions of the electrodes 431, 432 each show a curved shape in which the fore-end portions thereof expand so that the dismal ends are respectively directed in outward opposed directions and each dismal end is curved so as to a sense thereof is reversed at a last stage of projection of the electrodes. An angle of the curving exceeds 90 degrees from the direction of the fore-end and an angle of the curving of 180 degrees is most preferable as shown in FIG. 32. Besides, the dismal end portions 431b, 432b which are the fore-end portions of the needle-like electrodes 431, 432 preferably assume a shape of a straight line each. Besides, when the fore-end portions of the electrodes 431, 432 are projected from the fore-end opening 424 of the sheath section 412, the base end portions 431c, 432c which remain in the sheath section 412, too, preferably assume a shape of a straight line each along a lengthwise axis direction of the sheath section 412 and the operation wire 427. The portions of the needle-like electrodes 431, 432 other than the straight distal end portions 431b, 432b including the needle tip portions 431a, 432a are preferably covered with an electrically insulating material.

Figure 35:
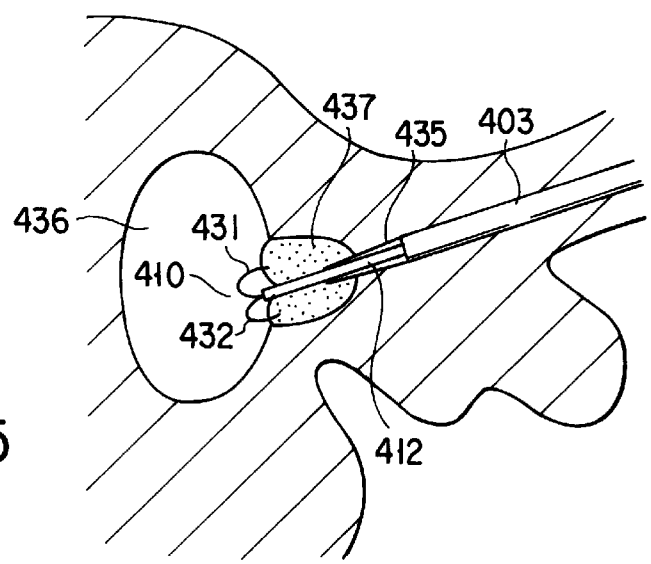
FIG. 35 is a sectional view showing a state in which the treatment tool of FIG. 30 is in operation.

When the prostatomegaly treatment is performed using the high frequency treatment operative tool 411, the insertion section 403 of the endoscope 401 is inserted through the urethra 435 as shown in FIG. 35 and the sheath section 412 of the high frequency treatment operative tool 411 is introduced into the bladder 436 through the operative tool inserting channel of the endoscope 401. At this point, since the needle-like electrode section 410 is accommodated, being withdrawn, in the sheath section 412 as shown in FIG. 34, the needle-like electrodes 431, 432 of the needle-like electrode section 410 do not disturb the introduction of the high frequency treatment operative tool 411.

When the fore-end of the sheath section 412 of the high frequency treatment operative tool 411 is positioned in the bladder 436, the slider 415 of the operation section 413 is advanced and the needle-like electrodes 431, 432 of the needle-like electrode section 410 is protruded from the fore-end opening 424 of the sheath section 412. As the needle-like electrodes 431, 432 are protruded from the fore-end opening 424 of the sheath section 412, the fore-end portions each show a curve shape in which the fore-end portions expand in outward opposed directions and at the last stage, as shown in FIG. 32, the fore-end portions 431a, 432a of the needle-like electrodes 431, 432 each are directed toward the proximal end side in a straight shape. Therefore, when the high frequency treatment operative tool 411 is pulled toward the proximal side together with the sheath section 412, the needle-like electrodes 431, 432 of the high frequency treatment operative tool 411 are advanced toward the prostate 437 from inside the bladder and the needle tip portions 431a, 432a are thrust through the prostate 437. FIG. 35 shows the state after the thrusting through of the needle-like tip portions 431a, 432a. After the needle-like electrodes 431, 432 perform paracentesis into the prostate 437, a high frequency current from the high frequency power source is supplied between the electrodes 431, 432 and the external electrode and tissues in the prostate 437 is destroyed or evaporated away. In the mean time, high frequency control in this case is performed in a similar manner to the first embodiment. That is, a setting section for setting a treatment mode (control mode) is provided and the maximal value of high frequency output is confined to be equal to or less than a predetermined value according to a set treatment mode (heating, coagulation, dissection and the like).

According to the embodiment, as described above, since it is certain that the needle-like electrodes 431, 432 can perform paracentesis into the prostate 437 at a right angle, operation in the paracentesis into the prostate can be easy and sure. Besides, since the endoscope 401 of a flexible type is employed, a pain felt by a patient is alleviated.

Figure 36:
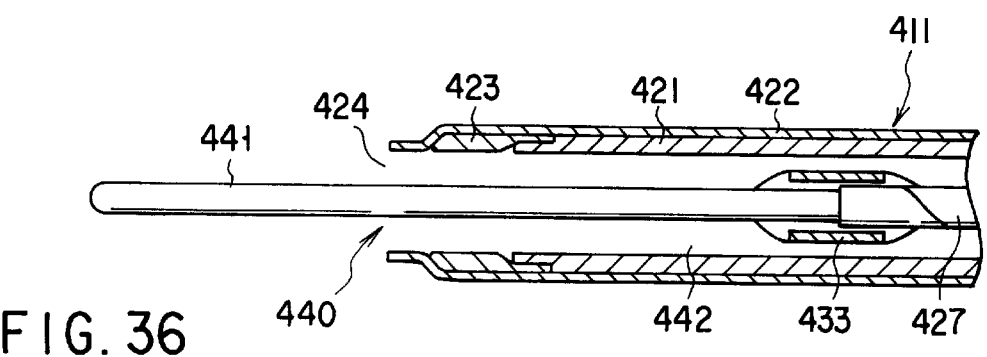
FIG. 36 is a longitudinal sectional view of a fore-end portion of a treatment tool of a high frequency treatment apparatus according to a twelfth embodiment of the present invention.
Figure 37:
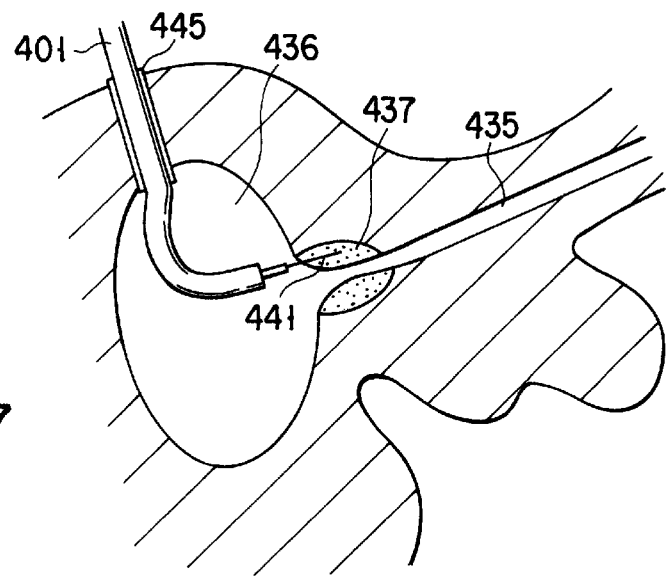
FIG. 37 is a sectional view showing a state in which the treatment tool of FIG. 36 is in operation.

FIGS. 36 and 37 show the twelfth embodiment. In a high frequency treatment operative tool 411 of the embodiment, a needle-like electrode section 440 is a single needle-like electrode 441 made of a conductive material and having an almost straight shape. The base end of the needle-like electrode 441 is connected to the fore-end of an operation wire 427. The needle-like electrode 441 can freely forward or backward move along an axial direction of an inner cavity 442 of the sheath section 412 by forward or backward, moving the operation wire 427 in the inner cavity 442 of the sheath section 412 with an operation section 413, and can be protruded from an fore-end opening 424 of the sheath section 412 or withdrawn to be accommodated in the sheath section 412 as shown in FIG. 36. The other construction of the sheath section 412, a structure of the proximal side operation section and the like are same as the eleventh embodiment.

When a treatment of the prostatomegaly is effected using the high frequency treatment operative tool 411 with such a construction, an insertion section 403 of an endoscope 401 is inserted into the bladder 436 through a fistula tube 445 provided in the body surface and the fore-end of the insertion section 403 of the endoscope 401 is advanced so that the prostate 437 can be observed in a front view thereof. Then, the sheath section 412 of the high frequency treatment operative tool 411 is inserted through an operative tool inserting channel of the endoscope 401 and the fore-end portion of the sheath section 412 is protruded from the insertion section 403 of the endoscope 401. The needle-like electrode 441 is further protruded from the sheath section 412 and the fore-end of the needle like electrode 441 is forced to perform paracentesis into the prostate 437 while confirming a position of the prostate 437 with the endoscope 401. After the paracentesis is completed, a high frequency current is supplied to the needle-like electrode 441 from the high frequency power source and tissues in the prostate 437 is destroyed or evaporated away, as describe above.

According to the embodiment, as described above, since the needle-like electrode 441 can perform the paracentesis at a right angle, operation in the paracentesis can be easy and sure on the prostate 437. Besides, since the paracentesis can be performed in the visual field of the endoscope 401, the paracentesis operation is easy and highly safe.

Figure 38:
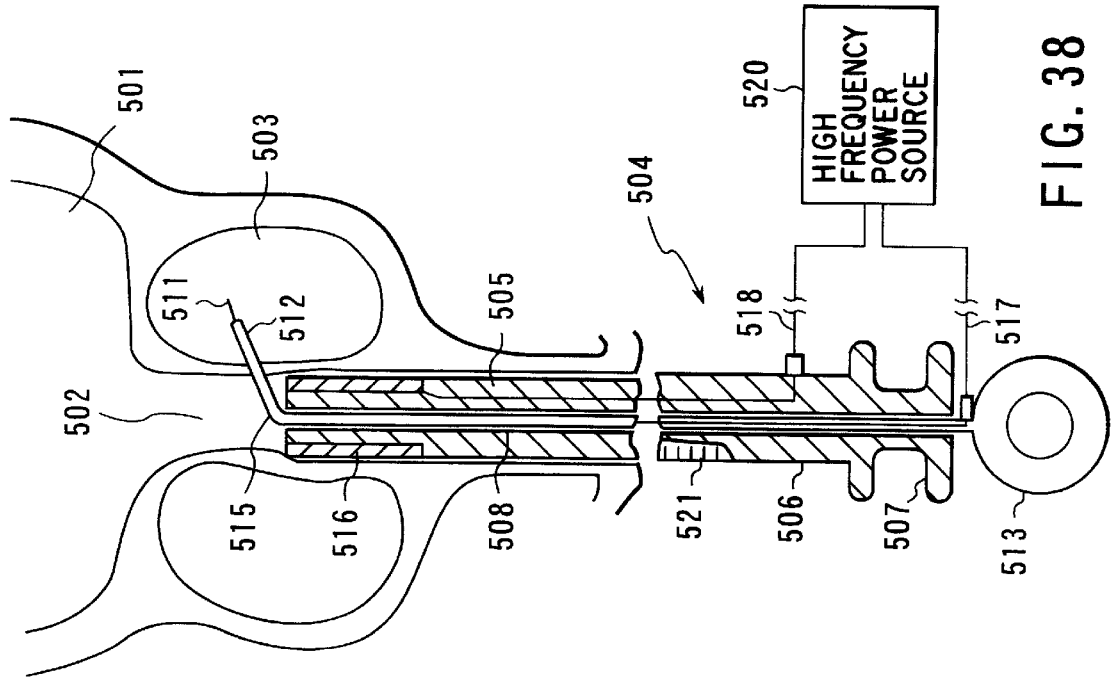
FIG. 38 is a diagram of a construction of a high frequency treatment apparatus according to a thirteenth embodiment of the present invention.

FIG. 38 shows the thirteenth embodiment of the present invention. A high frequency treatment apparatus of the embodiment is constructed of an electrode probe 504 as a treatment tool and a high frequency power source 520 as a high frequency generation section. In the figure, 501 indicates the bladder of an organism, 502 the urethra, and 503 a hypertrophic part of the prostate. The electrode probe 504 has an insertion section 505 which can be inserted into the urethra (biogenic lumen) 502 and an operation section 506 is provided at the proximal end of the insertion section 505. A finger hook section 507 is formed in the operation section 506. An insertion channel (inner cavity) 508 which penetrates through the central portion along the longitudinal direction of the insertion section 505 is formed in the insertion section 505. An insulating tube 512 made of an electrically insulating material, which covers a power supply wire (lead wire) of a first electrode 511 can be inserted in the insertion channel 508. The insulating tube 512 has at least a length enough for the proximal side end to protrude from the operation section 506 when the insulating tube 512 is inserted into the insertion channel 508. An operation member 513 for moving the insulating tube 512 forward or backward is connected to the proximal end of the insulating tube 512. The first electrode 511 is provided at the fore-end of the insulating tube 512 in an exposed manner and a paracentesis needle electrode section is formed by this exposed portion.

A deflection section 515 for guiding a direction along which the fore-end portion of the insulating tube 512 which protrudes from the insertion channel 508 so as to conform with an insertion direction toward the urethra 502, that is a direction toward the side which forms a predetermined angle to the central axis direction of the insertion section 505 is provided at the fore-end of the insertion section 505. Here, the fore-end portion of the insulating tube 512 is guided out with a slight obliqueness to the side and paracentesis of the needle-like first electrode 511 into the tissues of the hypertrophic part 503 of the prostate is performed. A second electrode 516. having a larger surface area than that of the first electrode 511 is provided along the outer periphery of the fore-end portion of the insertion section 505. The second electrode 516 is constructed of a conductive member having the shape of a thin film cylinder which is mounted to the fore-end of the insertion section 505 along all peripheral surface thereof.

A first lead wire 517 is connected to the first electrode 511 and a second lead wire 518 is connected to the second electrode 516. The lead wires 517, 518 are electrically connected to the high frequency power source 520 in a state in which the lead wires 517, 518 are insulated from each other. Besides, scale marks 521 with which an insertion length of the insertion section 505 into the urethra 502 is confirmed is provided in the base end side peripheral portion of the insertion section 505.

Then, operations of the above construction will be described.

A position of a hypertrophic portion 503 of the prostate is observed by an ultrasonic probe or the like, not shown, which is inserted into the anus and a length by which the insertion section 505 is inserted into the urethra 502 is measured in advance. Then, the insertion section 505 is inserted into the urethra 502. A length by which the insertion section 505 is inserted is determined while a scale mark 521 is matched with the measured length value. The insulating tube 512 provided with the first electrode 511 which is a paracentesis electrode is subsequently slid by operating the operation member 513 and the fore-end of the insulating tube 512 is advanced toward the side with the help of the deflection section 515, whereby the first electrode 511 is forced to perform paracentesis into the central position of the hypertrophic portion 503 of the prostate (see FIG. 38). When power is supplied from the high frequency power source 520 in this state, since a high frequency current is made to flow from the tiny first electrode 511 into the second electrode 516, which has a comparatively large area, and which is arranged in the urethra in the vicinity of the first electrode 511, the fore-end portion of a very small size of the first electrode 511 which has a smaller area locally produces heat and a coagulation treatment of the hypertrophic portion 503 of the prostate is carried out. A coagulation treatment is further carried out while changing a paracentesis position of the first electrode 511. Such procedures are continuously repeated some times. In the mean time, high frequency control is effected in a similar manner to that in the first embodiment. That is, in the embodiment, a setting section for setting a treatment mode (control mode) is provided and high frequency output is confined to be equal to or less than a predetermined value according to a set treatment mode (heating, coagulation, dissection, and the like).

In the embodiment, as described above, since the second electrode 516 is provided along the outer peripheral portion of the fore-end of the insertion section 505 with a comparatively large area and a site located between the first electrode 511 and the second electrode 516 is supplied with a local current, not only can heat efficiently be produced at the fore-end portion of the first electrode 511, but a coagulation treatment can locally carried out with safety.

Since the second electrode 516 is placed at a position of a hypertrophic portion 503 of the prostate in advance and the first electrode 511 performs paracentesis into a site in the hypertrophic portion 503 of the prostate, a comparatively large. extent of the hypertrophic portion 503 of the prostate can be cauterized even in one run of paracentesis. Besides, when paracentesis of the first electrode 511 into sites of the hypertrophic portion 503 of the prostate is repeatedly run more than once, a more larger extent of the hypertrophic portion 503 of the prostate can be cauterized. Besides, since the second electrode 516 is arranged along the outer periphery of the insertion section 505, a comparatively large area can be secured for the second electrode 516 and as a result, a current is concentrated in the first electrode 511 and cauterization of the hypertrophic portion 503 of the prostate can efficiently be carried out.

Figure 39:
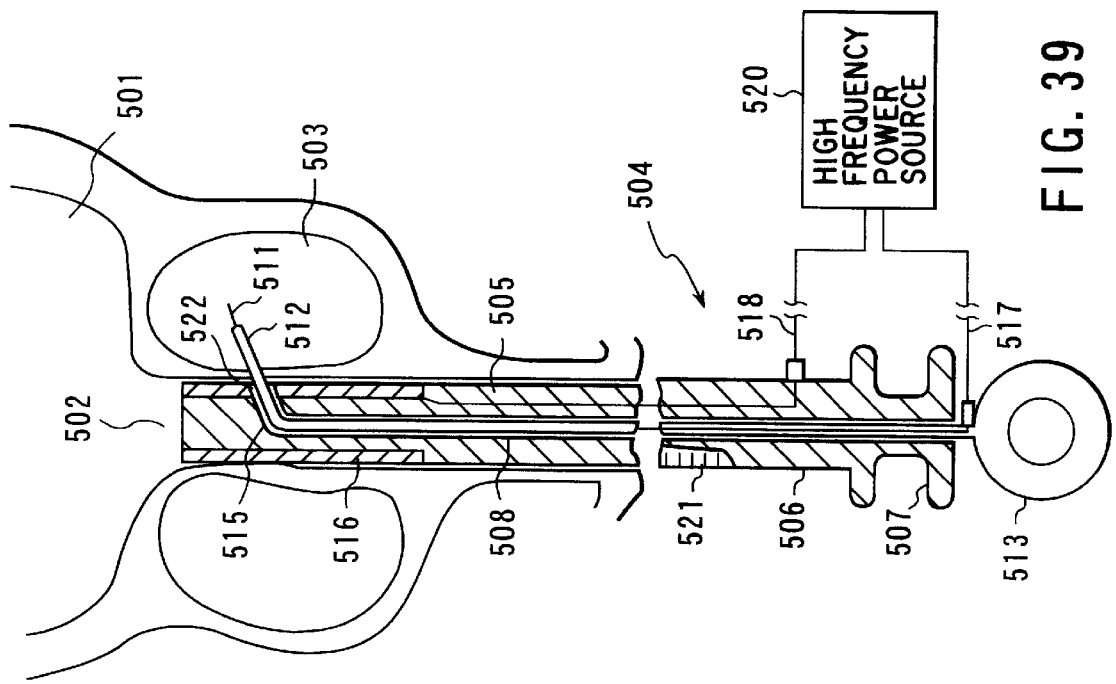
FIG. 39 is a diagram of a construction of a high frequency treatment apparatus according to a fourteenth embodiment of the present invention.

FIG. 39 shows the fourteenth embodiment of the present invention. The embodiment is modification of the thirteenth embodiment and different from the thirteenth embodiment only second electrode 516 and in a structure of a deflection section 515 through which a first electrode 511 is guided out with a deflection. Since the other construction is same as the thirteenth embodiment, description thereof is omitted. That is, a second electrode 516 is provided along the outer periphery of the fore-end portion of an insertion section 505. A side hole 522, which faces in the direction toward the side, and which communicates with an insertion channel 508 is provided in the fore-end peripheral wall portion of the insertion section 505 which is located at a part of the outer peripheral surface of the second electrode 516. The side hole 522 not only guides the fore-end of an insulating tube 512 which is introduced into the insertion channel 508, but constitutes a deflection section 515 for guiding a direction along which the fore-end of the insulating tube 512 is guided out to conform with a direction which forms a predetermined angle to an insertion direction into the urethra 502 and deflecting the direction along which the fore-end of the insulating tube 512 toward the side. An electrode surface area of the second electrode 516 is larger than that of the thirteenth embodiment. The side hole 522 through which the first electrode passes is provided at a site of a distance inward from the fore-end of the second electrode 516. Functions of such a construction is omitted since the positioning method of the insertion section 505, the power supply method and the like are similar to the case of the thirteenth embodiment.

In the embodiment, as described above, since the side hole 522 through which the fore-end portion of the insulating tube 512 is guided out is located at a site in the region covered by the second electrode inward from both ends, the surface area of the second electrode 516 is large as compared with that of the thirteenth embodiment and the first electrode 511 can be arranged at a site close to the middle of the region covered by the second electrode 516, even when output of a high frequency power source 520 is raised, a treatment can be carried out with efficiency and safety.

Figure 40:
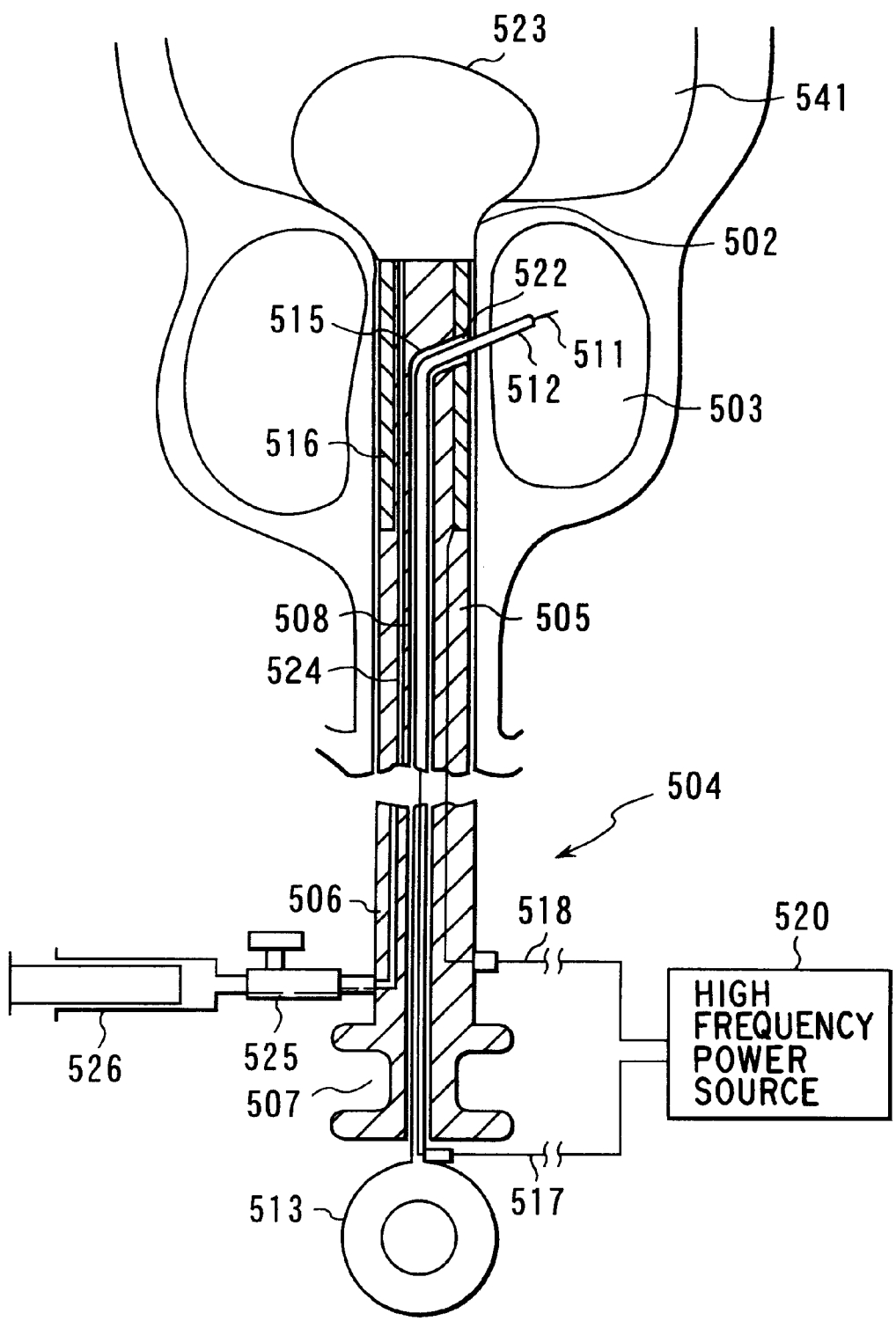
FIG. 40 is a diagram of a construction of a high frequency treatment apparatus according to a fifteenth embodiment of the present invention.

FIG. 40 shows the fifteenth embodiment of the present invention. The embodiment is modification of the fourteenth embodiment and only an insertion position determining means of an insertion section 505 is different from that of the fourteenth embodiment. The other construction is same as the above described fourteenth embodiment and description thereof is omitted.

A balloon 523 made of rubber such as latex or the like is mounted at the fore-end portion of an insertion section 505. A conduit 524 which communicates with the balloon 523 is provided in the interior of the insertion section 505. Fluid such as air is sent into the balloon 523 through the conduit 524 and the balloon 523 can be expanded. The conduit 524 communicates with a cock 525 which is provided in a proximal side operation section 506 of the insertion section 505. Fluid supply means 526 such as a syringe is connected to the cock 525.

In such a construction, the insertion section 505 is inserted into the urethra 502 with no expansion of the balloon 523. The fore-end of the insertion section 505 is inserted to be positioned in a bladder 501 and the fluid supply means 526 is operated in this state and the fluid is sent into the balloon 523 to inflate the balloon 523. When the insertion section 505 is pulled back in this state, the balloon 523 is put into contact with a neck portion of the bladder 501 as shown in FIG. 40. Hence, the insertion section 505 is positioned relatively to the hypertrophic portion 503 of the prostate. Thereafter, a coagulation treatment is performed in a similar manner to the fourteenth embodiment.

In the embodiment, as described above, since the balloon 523 is employed, positioning of a first electrode 511 which is a penetration electrode relative to the hypertrophic portion 503 of the prostate can easily be performed. Other effects are similar to those of the fourteenth embodiment. In the mean time, while in the thirteenth to fifteenth embodiments, the case where the single first electrode 511 is employed is described, a plurality of first electrodes may be used.

Figure 41:
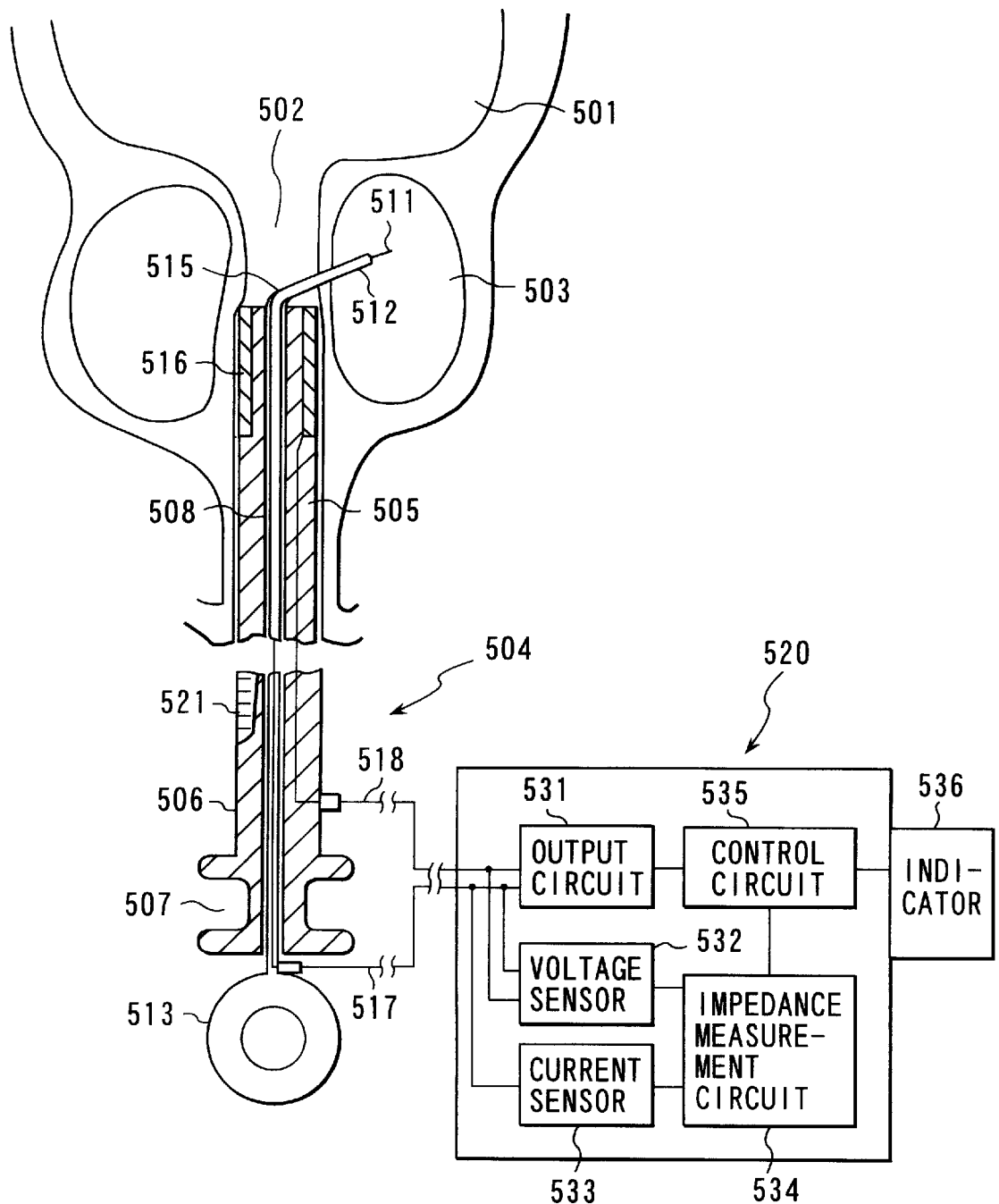
FIG. 41 is a diagram of a construction of a high frequency treatment apparatus according to a sixteenth embodiment of the present invention.

FIG. 41 shows the sixteenth embodiment of the present invention. The embodiment is different in construction of a high frequency power source 520 from the above described thirteenth embodiment and the other construction is same as the embodiment and therefore description thereof is omitted.

A high frequency power source 520 in the embodiment has an output circuit 531 and a first electrode 511 and a second electrode 516 are connected to an output circuit 531 through lead lines 517, 518. A voltage sensor 532 and a current sensor 533 which respectively measure a voltage value and a current value on the output side of the output circuit 531 are provided in the high frequency power source 520. The voltage sensor 532 and the current sensor 533 are connected to an impedance measurement circuit 534 and the impedance measurement circuit 534 is connected to a control circuit 535. The control circuit 535 is connected to not only the output circuit 531 but an indicator 536 which notices a coagulation state based on a measurement value of impedance using light or sound.

In the embodiment, an insertion section 505 is inserted in the urethra 502 to a predetermined position and a tissue impedance between the first electrode 511 and the second electrode 516 based on a voltage value and a current value of a high frequency output is measured by the impedance measurement circuit 534 in a stage in which a coagulation treatment by high frequency is carried out. When a measurement value or a change in the impedance has reached a predetermined value, the control circuit 535 sends a signal indicating completion of coagulation to the indicator 536. The indicator 536 notices an operator of completion of coagulation with light or sound based on the signal. When a measurement value or a change in measurement value has reached the predetermined impedance or the predetermined change in impedance, the control circuit 535 may send a signal to the output circuit to automatically stop a high frequency output or reduce the output. The operator pulls out the first electrode 511 based on the notice of the completion of coagulation and then performs another paracentesis at a different position changing a position to perform coagulation. Such procedures are repeated more than one run of paracentesis and thus a coagulation treatment across a large extent can be performed.

In the embodiment, as described above, since an impedance is measured, a coagulation treatment across a large extent can correctly be carried out for certain. Since an impedance of local tissues is measured by a bipolar method, a coagulation state can correctly be monitored.

Figure 42:
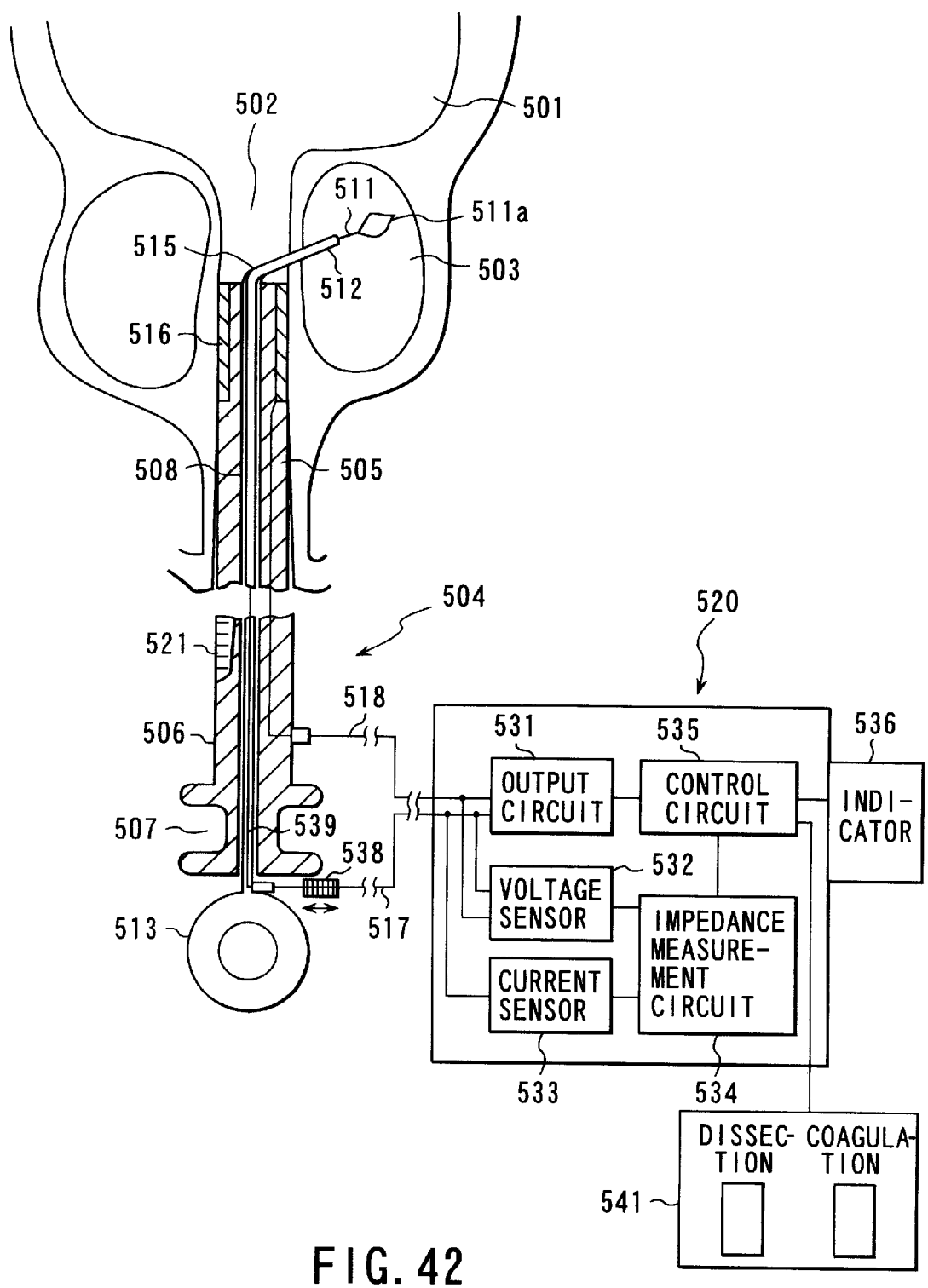
FIG. 42 is a diagram of a construction of a high frequency treatment apparatus according to a seventeenth embodiment of the present invention.
Figure 43:
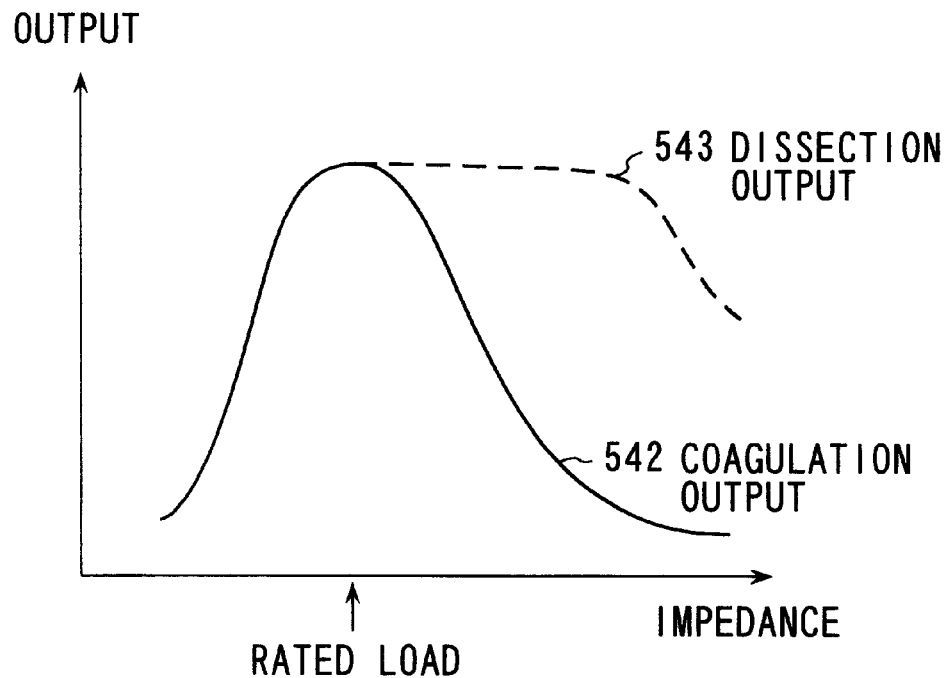
FIG. 43 is a characteristic graph of output in the coagulation mode.
Figure 44:
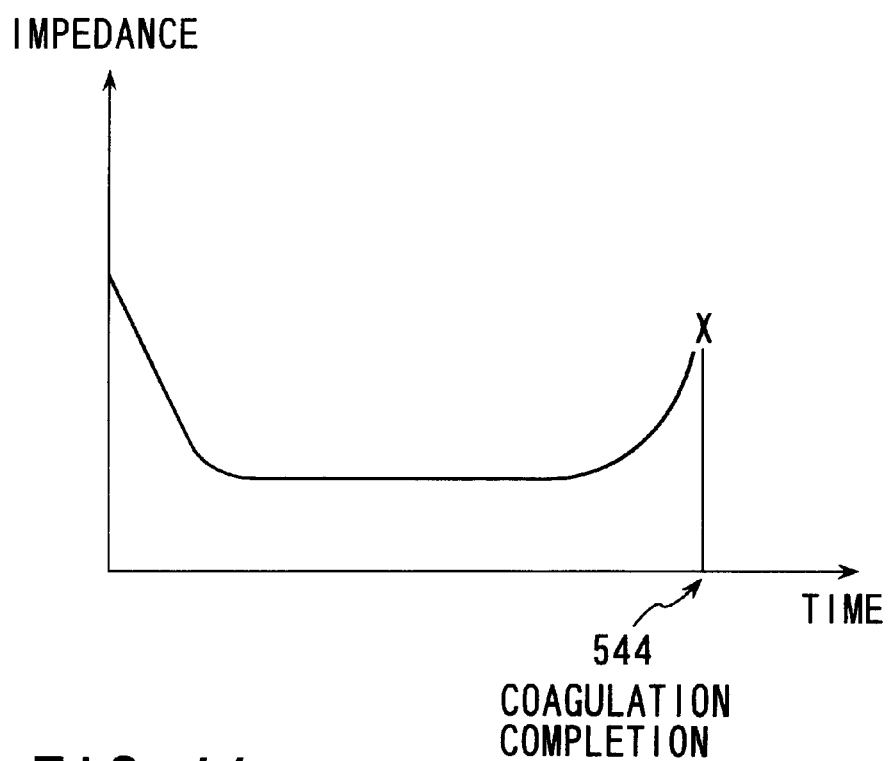
FIG. 44 is a graph showing a change in impedance in the coagulation mode.

FIGS. 42 to 44 show the seventeenth embodiment of the present invention. The embodiment is modification of the above described sixteenth embodiment. The embodiment is different from the sixteenth embodiment in a construction of a first electrode 511 and a construction of a high frequency power source 520. Since the other construction is same as the sixteenth embodiment, description thereof is omitted.

The fore-end portion of the first electrode 511 as a penetration electrode is formed in the shape of a snare wire and an operation in which the fore-end of the first electrode 511 can be changed from a needle like state as shown in FIG.

41 to a loop like state 511a as shown in FIG. 42 by a push/pull operation of an electrode shape control section 538 which is provided at an operation member 513 is enabled. For example, a base portion of the first electrode 511 is partly pulled in from the fore-end of an insulating tube 512 through a power supply wire 539 which is inserted in the insulating tube 512 in a freely forward and backward movable manner and thereby the first electrode 511 is closed and assume a needle-like shape. On the other hand, a base portion of the first electrode 511 is partly sent out from the fore-end of the insulating tube 512 and thereby the first electrode 511 expands by a self-elastic force and forms a loop like shape. A foot switch 541 is connected to a control circuit 535 of a high frequency power source 520 and dissection output or coagulation output can be selected by operation of this foot switch 541.

Here, load characteristics of dissection output and coagulation output of the high frequency power source 520 will be described using FIG. 43. In general, a coagulation characteristic of a bipolar type shows an output characteristic in which an output is decreased as shown by a solid line 542 in the figure when a rated load has been exceeded as coagulation progresses. Here, when an output characteristic in which a high output is maintained even in a high impedance region as shown by a broken line 543 is set, tissues can be dissected even in a bipolar type.

Then, operations of the above construction will be described.

A coagulation operation is selected by the foot switch 541 in a state in which a shape of the fore-end of the first electrode 511 assumes a needle-like shape as shown in FIG. 41. Coagulation progresses as time, then, elapses as shown in FIG. 44 and the operator is noticed of completion of coagulation at a coagulation completion time 544 when an impedance value or a change in impedance reaches a predetermined value. Alternatively, a coagulation output may automatically be stopped or reduced at a coagulation completion time 544.

Here, not only does the operator change the fore-end of the first electrode 511 into a state of the loop-like shape 511a by operating the electrode shape control section 538, but can dissect a coagulated hypertrophic portion 503 of the prostate with no bleeding by performing an operation in which a dissection output of the foot switch 541 is selected. Tissues are dissected into small pieces by repeating a coagulation operation and a dissection operation more times than once. Dissected small pieces of the tissues are recovered.

According to the embodiment, as described above, the tissues of a hypertrophic portion of the prostate is not only coagulated, but dissected and recovered, whereby a treatment effect can be improved.

Figure 45:
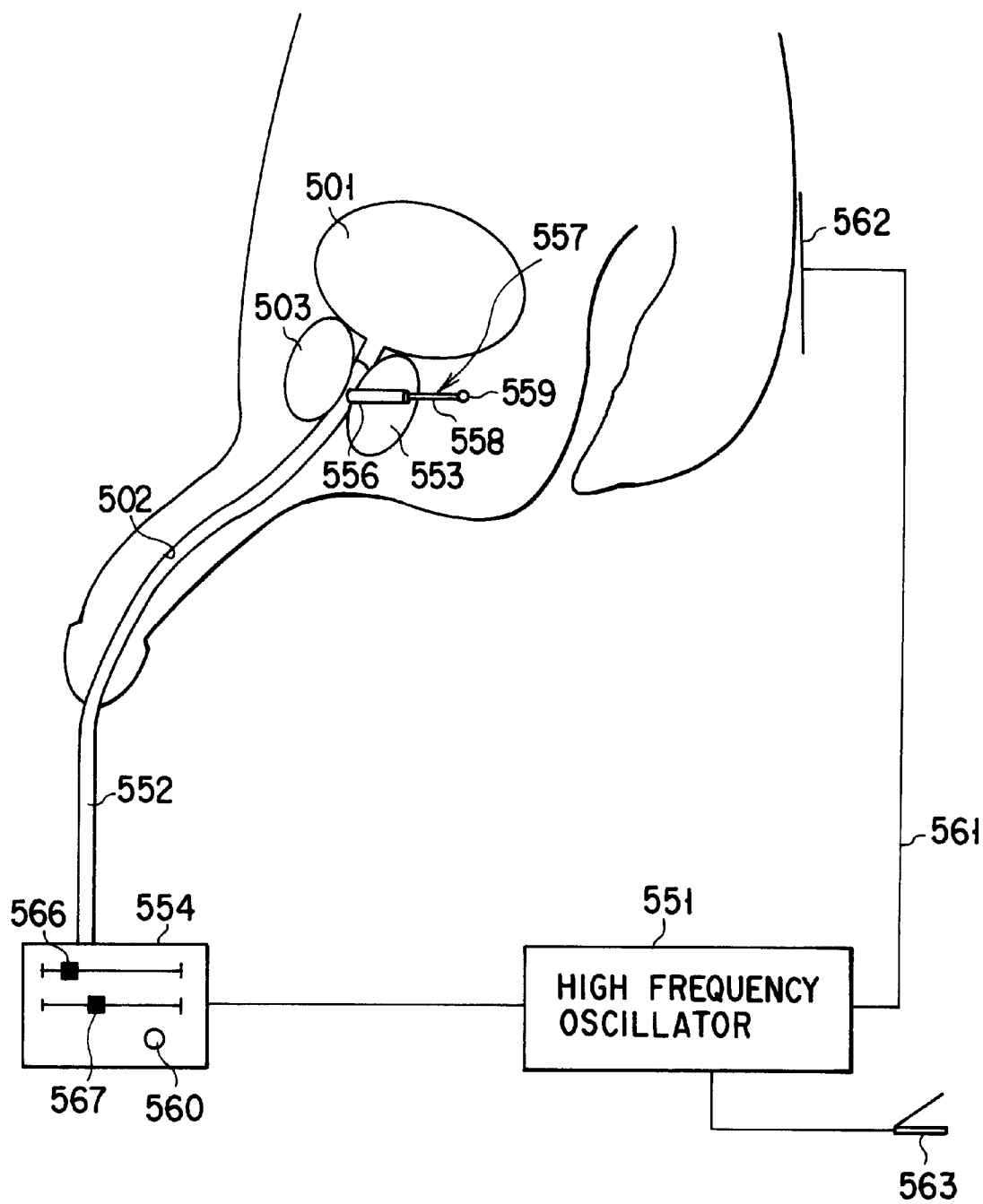
FIG. 45 is a diagram of a construction of a high frequency treatment apparatus according to a eighteenth embodiment of the present invention.
Figure 46A:
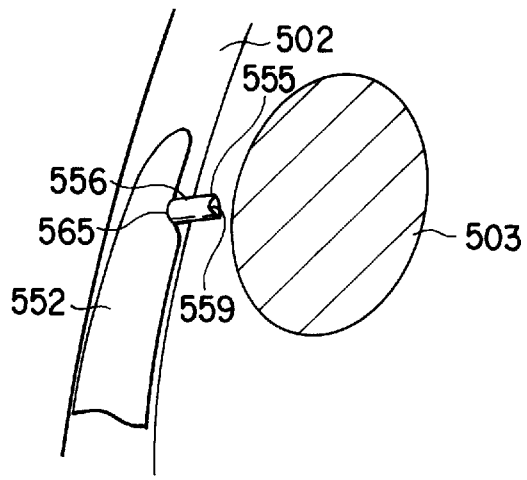
FIGS. 46A to 46D are sectional views showing states in which the high frequency treatment apparatus of FIG. 45 is in operation.
Figure 46B:
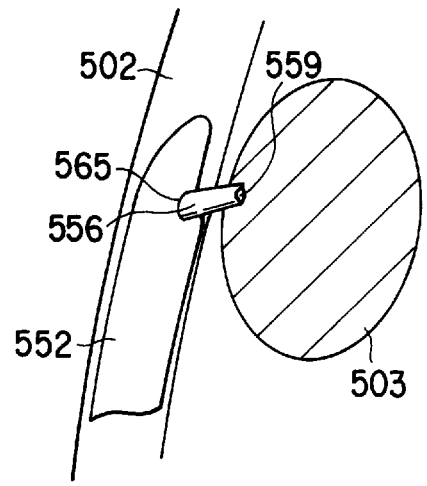
Figure 46C:
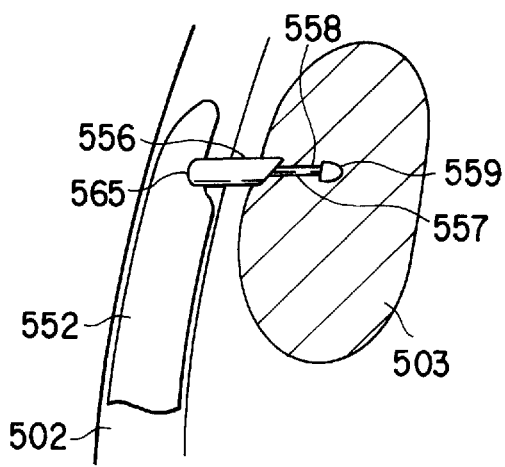
Figure 46D:
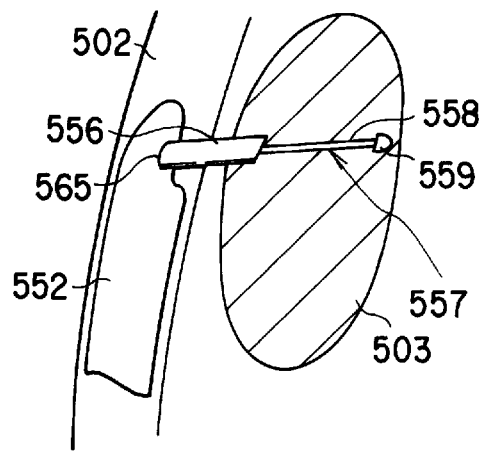

FIGS. 45 to 46D show the eighteenth embodiment of the present invention. A high frequency treatment apparatus for the prostatomegaly according to the embodiment, as shown in FIG. 45, comprises: a high frequency oscillator (high frequency generation section) 551; a catheter 552 as an insertion probe which can be inserted into the urethra 502; a penetration needle probe 553 not only which constitutes a treatment tool together with the catheter 552, but which can be inserted into an internal path of the catheter 552; and a catheter operation section 554 for operating the penetration needle probe 553.

The penetration needle probe 553, as shown in FIGS. 46A to 46D, has an insulating sleeve 556 made of an electrically insulating tube with the fore-end of a cut-away portion 555 which is sharpened like a needle. A penetration needle 557 is inserted in the insulating sleeve 556. The fore-end portion of the penetration needle 557 which is protruded from the fore-end of the insulating sleeve 556 constitutes a high frequency power supply electrode section 558 and the farthermost fore-end of the penetration needle 557 is constituted of an electrically insulating section 559 having a dull shape, for example a spherical shape, for example, of a larger diameter than that of the electrode section 558.

The catheter operation section 554 is provided with a switch 560 which controls the states of ON/OFF of power supply to the high frequency power supply electrode section 558 from the high frequency oscillator 551. An opposite electrode plate 562 is connected to the high frequency oscillator 551 through an opposite electrode plate connection cable 561. The opposite electrode plate 562 is provided in a state in which the opposite electrode plate 562 is put in close contact with the outer surface of an organism and receives a return current from the high frequency power supply electrode section 558. A foot switch 563 which can conduct the ON/OFF operation of high frequency power supply is connected to the high frequency oscillator 551 in addition to the switch 560 of the catheter operation section 554.

As shown in FIGS. 46A to 46D, a hole 565, which is open directing toward the side, and which communicates with the internal path of the catheter 552, is formed in the fore-end peripheral wall portion of the catheter 552, the fore-end portion of a penetration needle catheter 553 is guided out directing toward the side from a portion of the hole 565 and besides the fore-end portion of the penetration needle 557 can be protruded out from or withdrawn into the fore-end of the insulating sleeve 556 of the penetration needle catheter 553. That is, the fore-end portion of the insulating sleeve 565, in which the penetration needle 557 is incorporated while being inserted, can be guided out in a freely forward and backward movable manner at a predetermined angle to the axis center of the catheter 552.

The catheter operation section 554, as shown in FIG. 45, is provided with a high frequency power supply section forward/backward operation lever 566 which can move the high frequency power supply electrode section 558 for the penetration needle 557 in a forward/backward movable manner; an insulating sleeve forward/backward operation lever 567 which can move the insulating sleeve 556 for the penetration needle 557 in a forward/backward movable manner; and the switch 560 which is described above.

In the embodiment, the fore-end portion of the catheter 52 is made to approach the hypertrophic portion 503 of the prostate using the urethra 502. First of all, as shown in FIG. 46A, the cut-away portion 555 of the insulating sleeve 556 is advanced toward the tissues to be destroyed or target tissues for which a treatment is performed by pushing the insulating sleeve forward/backward operation lever 567 of the catheter operation section 554 and as shown in FIG. 46B, the fore-end of the penetration needle 557 is forced to perform paracentesis into the hypertrophic portion 503 of the prostate. After the penetration needle 557 performs the paracentesis into the hypertrophic portion 503 of the prostate once, the high frequency power supply forward/backward operation lever 566 of the catheter operation section 554 is pushed and the high frequency power supply electrode section 558 is pushed to the hypertrophic portion 503 of the prostate from the fore-end of the insulating sleeve 556 as shown in FIG. 46C, whereby a power supply extent is determined.

Since the high frequency power supply electrode section 558 is enveloped by the insulating sleeve 556, tissues outside the treatment extent can be prevented from being exposed to a high frequency current. An exposure amount of the electrode section 558 can be set by adjusting a position of the insulating sleeve 556 in the longitudinal direction with the insulating sleeve forward/backward operation lever 567 being pushed. Then, only a target tissues portion is selected and a high frequency current can be supplied there. After the setting, a high frequency current is supplied and thereby a treatment such as coagulation is carried out. In the mean time, high frequency control in this case is performed in a similar manner to the first. embodiment. That is, in the embodiment, a setting section for setting a treatment mode (control mode) is provided and the maximal value of high frequency output is confined to be equal to or less than a predetermined value according to a set treatment mode (heating, coagulation, dissection and the like).

When the high frequency power supply electrode section 558 is advanced in the inside of the hypertrophic portion 503 of the prostate by pushing the high frequency power supply forward/backward operation lever 566 of the catheter operation section 554. Further, thereby, the electric insulating section 559 whose fore-end has a dull shape hits the edge part of the hypertrophic portion 503 of the prostate, the operator can have knowledge of a state of hitting of the fore-end by feel of the hand. The operator thereby stops advancing the high frequency power supply electrode section 558 any further, so that the treatment can be performed with safety.

As described above, in the embodiment, since the fore-end of the high frequency power supply electrode section 558 is provided with the electrically insulating section 559 having a dull shape, after the insulating sleeve 556 penetrates into the hypertrophic portion 503 of the prostate, the high frequency power supply electrode section 558 can be advanced with safety. Since the insulating sleeve 556 and the high frequency power supply electrode section 558 can independently be moved forward and backward, after the high frequency power supply electrode section 558 penetrates into the hypertrophic portion 503 of the prostate, a power control section of the high frequency power supply electrode section 558 can be controlled. Hence, a power supply treatment can be performed only in the target tissues or across a large extent.

Figure 49:
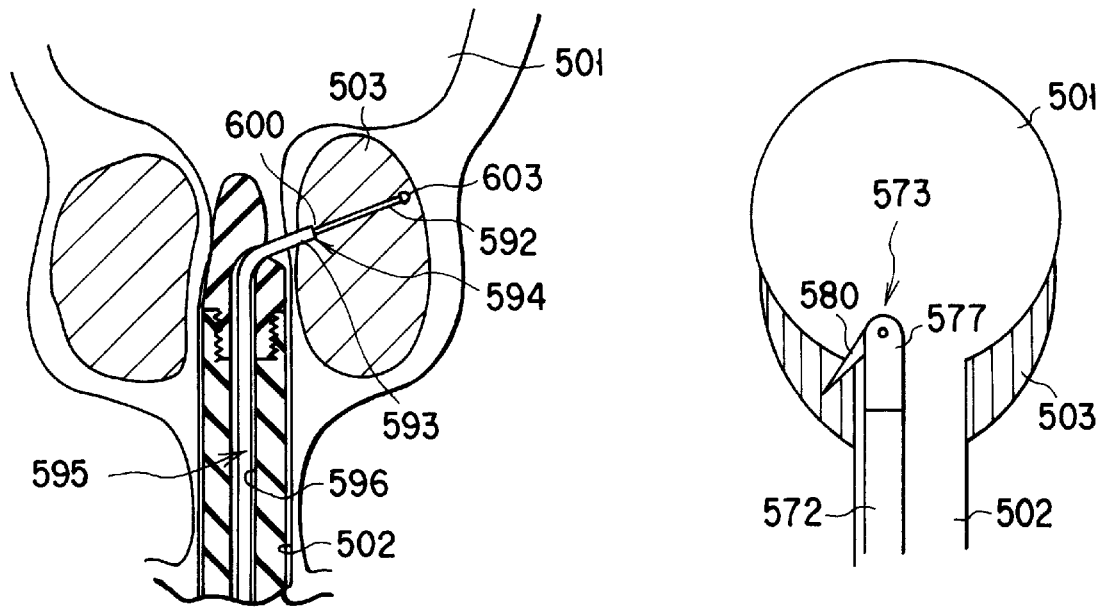
FIG. 49 is a sectional view showing a state in which the operative section of FIGS. 48A and 48B is in operation.

FIGS. 47 to 49 show the nineteenth embodiment of the present invention. A high frequency treatment apparatus is provided with a paracentesis coagulation forceps 571 as a treatment tool shown in FIG. 10. The forceps 71 has an operative section 573 at the fore-end of an narrow and long insertion section 572 with flexibility and an operation section 574 for operating the operative section 573 at the proximal. side base end of the insertion section 572.

As shown in FIGS. 48A and 48B, the insertion section 572 is built in the shape of a sheath from a flexible coil 576 which is covered with an electrically insulating material 575. The operative section 573 has a cover member 577 attached to the fore-end of the coil 576. The cover member 577 is provided with a slit 578 which not only extends along the longitudinal direction of the insertion section 572, but penetrates through to the fore-end. A pivotal pin 579 is provided in the fore-end portions of the left and right side portions of the cover member 577 and the base end portion of a needle electrode 580 with the sharp fore-end is pivotally supported by the pivotal pin 579. The needle electrode 580 is disposed within the width of the slit 578 and pivotably mounted about the pivotal pin 579. A middle portion of the needle electrode 580 is connected to a connection member 582 to which the fore-end of the fore-end of the operation wire 581 which extends to the proximal side through the inside of the coil 576 through a link plate 583. The slit 584 for accommodating the needle electrode 580 is formed in the connection member 582 as shown in FIG. 48A. The operation section 574 is provided with a fixed handle 586 and a slider 587 and the proximal end of the operation wire 581 which extends to the proximal side through the interior of the coil 576 is fixed to the slider 587. Besides, the operation wire 581 is connected to a high frequency power source, not shown, as the high frequency generation section by a cable 588 which is provided so as to be guided out from the slider 587.

Then, operations of the above described construction will be described.

As shown in FIGS. 47, 48A and 48B, the connection member 582 is advanced by the slider 587 through the operation wire 581 and thereby, the needle electrode 580 is opened in a direction moving away from the central axis of the cover member 577. When the needle electrode 580 is in use, the needle electrode 580 in the closed state is advanced through the urethra so that the operative section 573 is positioned in the bladder 501 and after the needle electrode 580 is opened as described above, the entire forceps 571 are withdrawn. Thereby, the needle electrode 580 performs paracentesis into the hypertrophic portion 503 of the prostate as shown in FIG. 49. When a high frequency current is supplied to the hypertrophic portion 503 of the prostate through the needle electrode 580 from the high frequency power source in a state in which the paracentesis of the needle electrode into the hypertrophic portion 503 of the prostate has been performed, the hypertrophic prostate 503 is coagulated and dissected. In the mean time, high frequency control in this case is performed in a similar manner to the first embodiment. That is, in the embodiment, a setting section for setting a treatment mode (control mode) is provided and the maximal value of high frequency output is confined to be equal to or less than a predetermined value according to a set treatment mode (heating, coagulation, dissection and the like).

As described above, since, in the embodiment, the insertion section 572 is flexible, the insertion section 572 is easy to be inserted through the urethra. In regard to paracentesis, since the paracentesis is performed by the needle electrode 580 with rigidity while pulling the insertion section 572, a force is transmitted with certainty and thereby treatments of coagulation and dissection for the hypertrophic portion 503 of the prostate can be carried out with ease and certainty. In the mean time, while a single electrode 580 is employed in the embodiment, another electrode 580 can be added at a symmetrical position with respect to the central axis.

Figure 50:
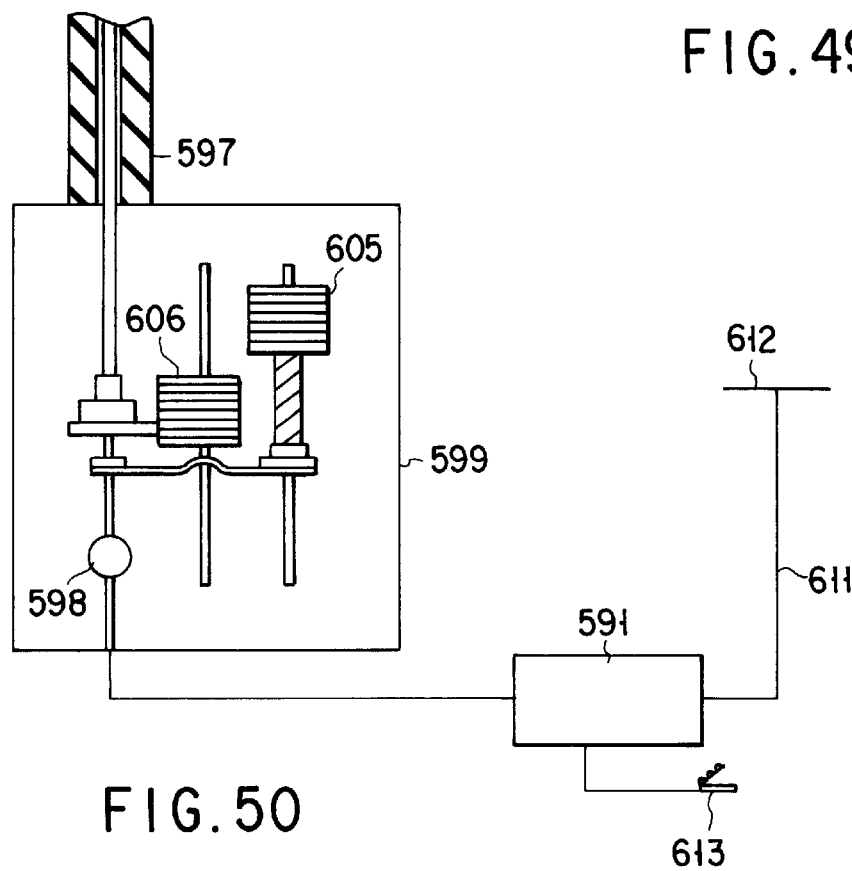
FIG. 50 is a diagram of a construction of a high frequency treatment apparatus according to a twentieth embodiment of the present invention.
Figure 51:
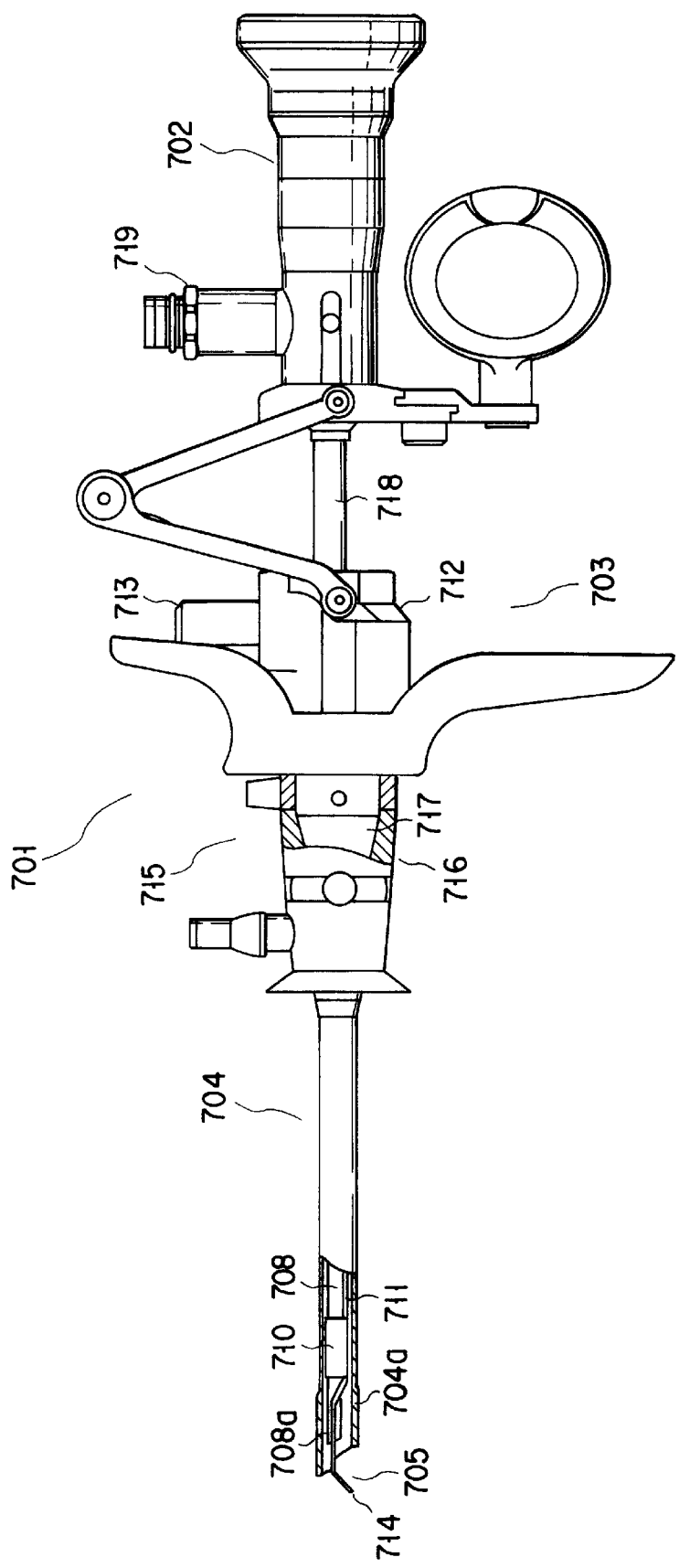
FIG. 51 is a side view of a treatment tool of a high frequency treatment apparatus according to twenty-first embodiment of the present invention.

FIG. 50 shows the twentieth embodiment of the present invention. A high frequency treatment apparatus for the prostatomegaly according to the embodiment comprises: a high frequency oscillator 591 as a high frequency generation section for supplying high frequency energy; a penetration needle probe 595 as a treatment tool, which has a high frequency power supply electrode section 592 at its fore end, which is inserted in an insulating sleeve 593 constructed of an electrically insulating tube, and which has a penetration needle 594 at its fore end; a catheter 597 having an insertion section inner cavity 596 through which the penetration needle probe 595 passes; and a catheter operation section 599 having a switch 598 for performing the ON/OFF control of power supply. The fore-end of the insulating sleeve 593 of the penetration needle probe 595 constitutes a penetration needle 594 as a pin-pointed cut-away portion 600. The fore-end portion of the penetration needle 594 protruded from the fore-end of the insulating sleeve 593 constitutes the high frequency power supply electrode section 592 and the farthermost fore-end of the penetration needle 594 constitutes an electrically insulating section 603 having a dull shape as described above.

The catheter operation section 599 is provided with: a high frequency power supply section forward/backward operation lever 605 which can operate penetration needle 594 of the penetration needle probe 595 in a forward/backward movable manner; and an insulating sleeve forward/backward operation lever 606 which can operate the insulating sleeve 593 of the penetration probe 595 in a forward/backward movable manner. An opposite electrode plate 612 is connected to the high frequency oscillator 591 through an opposite electrode plate connection cable 611. The opposite electrode plate 612 is put in close contact with the outer surface of an organism and receives a return current from the high frequency power supply electrode section 592. A foot switch 613 which can effect the ON/OFF operation of high frequency power supply is connected to the high frequency oscillator 591 in addition to the switch 598 of the catheter operation section 599.

In this high frequency treatment apparatus for the prostatomegaly, the fore-end of the catheter 597 is made to approach a hypertrophic portion 503 of the prostate using the urethra 502. A cut-away section 600 of the insulating sleeve 593 is advanced in the direction of tissues to be destroyed or target tissues for which a treatment is performed by a pushing operation of the insulating sleeve forward/backward operation lever 606 of the catheter operation section 599. The penetration needle 594 is made to penetrate into the hypertrophic portion 503 of the prostate. After the penetration needle 594 is made to penetrate into the hypertrophic portion 503 of the prostate once, the high frequency power supply electrode section 592 is pushed to the hypertrophic portion 503 of the prostate by pushing the high frequency power supply section forward/backward operation lever 605 of the catheter operation section 599 and thereby a power supply extent is determined. Then, power supply is effected and thereby a treatment such as coagulation and the like is performed. In this case, too, it is needless to say that high frequency control is performed in a similar manner to the first embodiment.

In the embodiment, as described above, since an electrically insulating section 603 having a dull shape is formed at the fore-end of the high frequency power supply electrode section 592, after the insulating sleeve 593 is made to penetrate into the hypertrophic portion 503 of the prostate, the high frequency power supply electrode section 592 can be advanced with no anxiety. Besides, since the insulating sleeve 593 and the high frequency power supply electrode section 592 can independently be moved forward and backward, after the high frequency power supply electrode section 592 is made to penetrate into the hypertrophic portion 503 of the prostate, a power supply section of the high frequency power supply electrode section 592 can be controlled. Hence, a power supply treatment of only target tissues or across a large extent can be carried out.

FIGS. 51 to 54 show the twenty-first embodiment of the present invention. A high frequency treatment apparatus of the embodiment is provided with a prostate excision mirror 701 shown in FIG. 51. The prostate excision mirror 701 is constructed of an endoscope 702; a handle 703; a sheath 704; an electrode 705 as a prostate removal tool which is a treatment tool; a mandrin 706; and an internal needle 707. The endoscope 702 is mounted to the handle 703 by a lock pin (not shown) in a mountable and demountable manner, a fore-end 708a of an insertion section 708 of the endoscope 702 is inserted a tubular cavity formed by the handle 703 and the sheath 704 and the insertion section 708 of the endoscope 702 is formed so as to have a length which reaches up to the insertion section fore-end 704a of the sheath 704. The handle 703 is fixed to the body section 716 of the sheath 704 by inserting connection section 717 into the body section 716 of the sheath 704 and fixing the connection section 717 by a fixation ring 715.

Figure 52A:
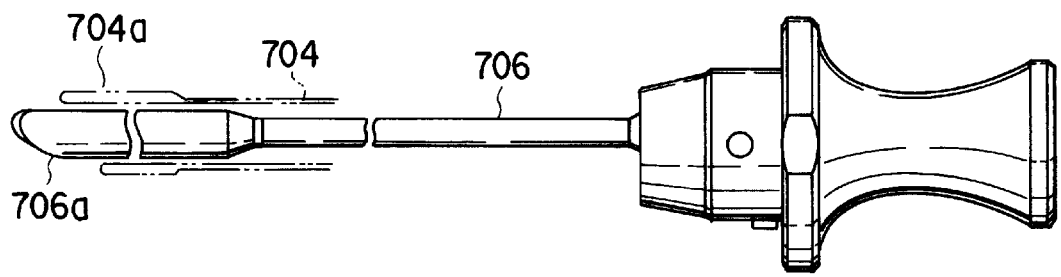
FIG. 52A is a side view of a fore-end portion of a mandrin.
Figure 52B:
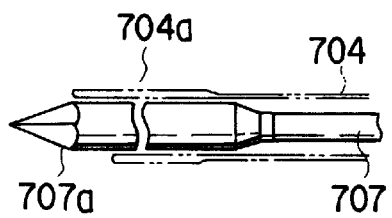
FIG. 52B is a side view of a fore-end portion of an internal needle.

A stabilizer 710 is engaged in an insertion section 708 of the endoscope 702, a shaft 711 which is joined with the stabilizer 710 penetrates through an inner cavity of an insertion section of the. sheath 704 and thereby the electrode 705 is fixed to a slider 712 of the handle 703. In this case, mechanical connection works as electrical connection simultaneously and thereby, electrical conduction between a terminal 13 and an operative section 14 is achieved. When the slider 712 is slid forward or backward on a rail 718, the electrode 705 fixed to the slider 712 is moved in one body with the slider 712 and the electrode 705 is moved in a freely forward and backward movable manner relative to the fore-end portion 708a of the insertion section 708 of the endoscope 702. The mandrin 706 and the internal needle 707 are mounted to the sheath 704 in a positional relation in the fore-ends as shown in FIGS. 52A and 52B. That is, the fore-end 706a of the mandrin 706 has a dull shape. The fore-end 707a of the internal needle 707 has the shape of a sharp triangular pyramid. The fore-end 707a of the internal needle 707 may assume the shapes of a circular cone or a knife as far as the fore-end 707a has a sharp shape by which paracentesis into body tissues can be performed.

Figure 53:
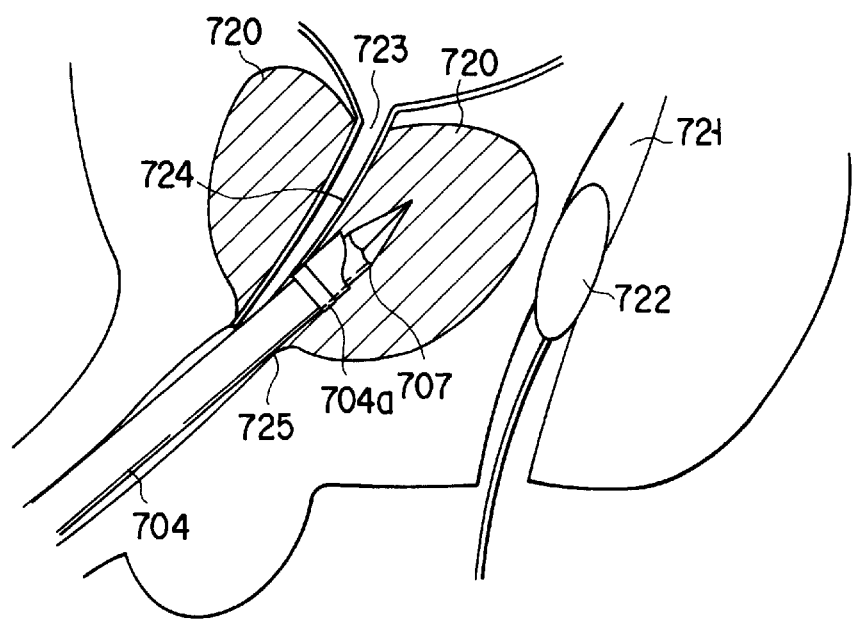
FIG. 53 is a sectional view showing a state in which the internal needle of FIG. 52B is in operation.

Then, operations of the twenty-first embodiment will be described. As shown in FIG. 53, the sheath 704 to which the mandrin 706 is provided is inserted into the urethra 723 and further advanced till the fore-end of the mandrin 706 reaches a paracentesis position 725 of the prostate 720. Then, the mandrin 706 is pulled off from the sheath 704, the mandrin 706 is replaced with the internal needle 707, paracentesis into the prostate 720 by the internal needle 707 and the sheath 704 is performed through the tunica mucosa 724 of the urethra while confirming a position of the internal needle 707 with an ultrasonic observation apparatus 722 inserted into the rectum.

A positional confirmation of the internal needle 707 may be conducted by fluororoentgenography. After the paracentesis of the sheath 704, the endoscope 702 to which the internal needle 707, the handle 703 and the electrode 705 are mounted is mounted to the sheath 704. Besides, a light guide for transmitting illumination light from an optical source (not shown), a cord for transmitting a high frequency current from a high frequency power source apparatus (not shown) as a high frequency generation section are respectively connected to a light guide base 719 and a terminal 713.

Figure 54:
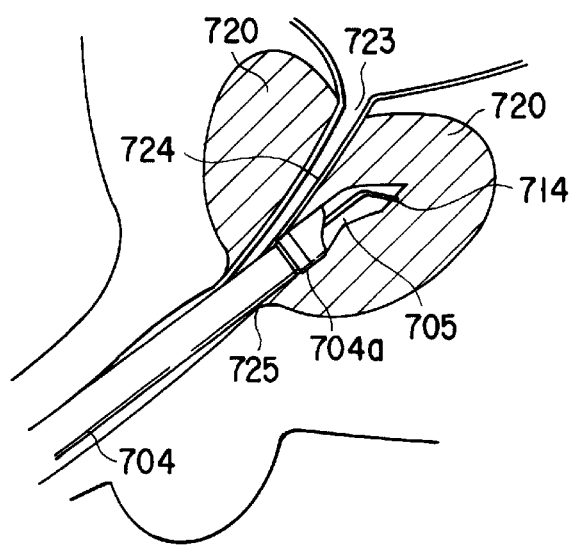
FIG. 54 is a sectional view showing a state in which the treatment tool of FIG. 51 is in operation.

The operator excises the tissues of the prostate 720 by the electrode 705 under observation with the endoscope 702 in a similar manner to conventional TUR-P in a state in which paracentesis of the fore-end of the prostate excision mirror 701 into the prostate 720 has been performed as shown in FIG. 54. High frequency control in this case is effected in a similar manner to the case in the first embodiment. That is, in the embodiment, a setting section for setting a treatment mode (control mode) is provided and the maximal value of high frequency output is confined to be equal to or less than a predetermined value according to a set treatment mode (heating, coagulation, dissection and the like). After the operation is finished and further no bleeding is confirmed, the handle 703, the endoscope 702 and the electrode 705 are pulled off from the sheath 704, the mandrin 706 substitutes for them and the sheath 704 is pulled off from the urethra. The retracted wound portion of tunica mucosa of the urethra after the operation is closed with a fibrin paste, an organism absorbable clip or the like and thereby necessary procedures can be completed without any suture.

Figure 55:
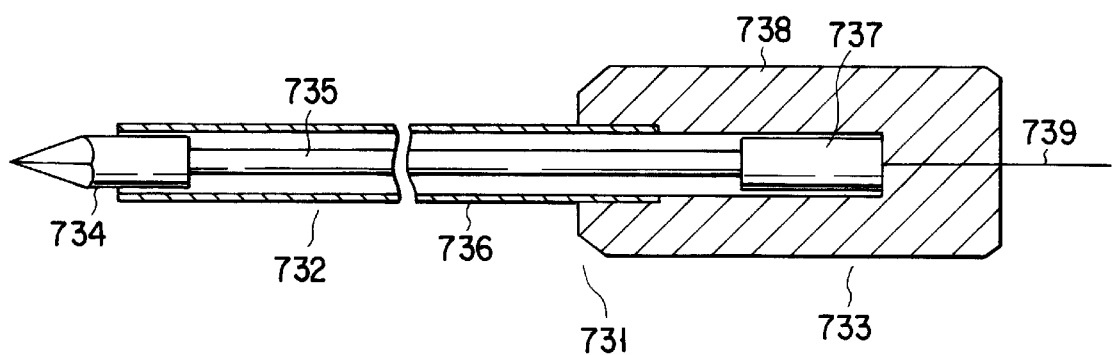
FIG. 55 is a longitudinal sectional side view of a treatment tool of a high frequency treatment apparatus according to a twenty-second embodiment of the present invention.

FIG. 55 shows the twenty-second embodiment of the present invention and an ultrasonic paracentesis tool 731 which is inserted into a sheath 704 of a prostate excision mirror 701 shown in the twenty-first embodiment. In the ultrasonic paracentesis tool 731, an operation section 733 is mounted to the base end of an insertion section 732. In the insertion section 732, a hone 735 is mounted to a sheath 736 concentrically and a blade 734 mounted on the fore-end of the hone 735 is protruded from the fore-end of the sheath 736. The base end side of the sheath 736 is fixed in a housing 738. A vibrator 737 is disposed in the housing 738 and the base end side of the hone 735 is connected to the vibrator 737. A electric:wire 739 is connected to the vibrator 737 and the vibrator 737 is electrically connected to a drive circuit of a control unit (not shown). The blade has the shape of a triangular pyramid. A shape of the blade 734 may also be of a circular cone or a knife.

Operations of the twenty-second embodiment will be described. In paracentesis of the sheath 704, the sheath 704 to which a mandrin 706 is inserted is inserted through the urethra 723 and the sheath 704 is further advanced till the fore-end of the mandrin 706 comes to a paracentesis position 725 of the prostate 720. Then, the mandrin 706 is replaced with the ultrasonic paracentesis tool 731 and paracentesis into the prostate 720 by the blade 734 is performed pressing the blade 734 which is ultrasonically kept vibrated to the prostate 720. The tissues which is put in contact with the blade 734 which is ultrasonically kept vibrated are destroyed and dissected. Since procedures thereafter are same as those in the twenty-first embodiment, description thereof is omitted.

According to the embodiment, since the ultrasonic paracentesis tool 731 is employed, a penetration force necessary in paracentesis by the sheath 704 can be small and the paracentesis can performed with safety and certainty. Hemostasis by coagulation in the dissected portion is effected by frictional heat of the blade 734 which is ultrasonically kept vibrated and thereby bleeding in the paracentesis is suppressed.

Figure 56:
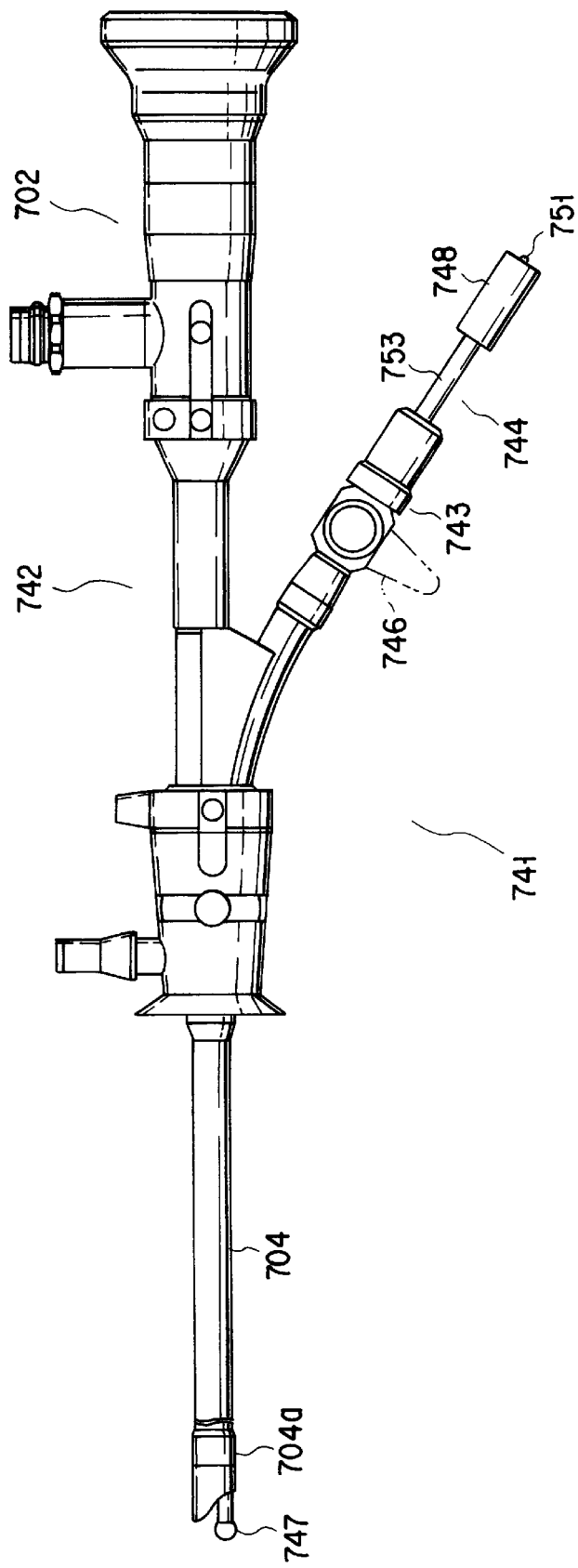
FIG. 56 is a side view of a treatment tool of a high frequency treatment apparatus according to a twenty-third embodiment of the present invention.

FIGS. 56 to 58C show the twenty-third embodiment and a urethra bladder mirror 741 is shown in FIG. 56. The urethra bladder mirror 741 is constructed of: an endoscope 702; a bridge 742; a sheath 704; a mandrin 706; and an internal needle 707. Constructions of the endoscope 702, the sheath 704, the mandrin 706 and the internal needle 707 are same as those in the twenty-first embodiment. Connection of the bridge 742 with the endoscope 702 and the sheath 704 is same as the way of connection of the handle 703 in the twenty-first embodiment.

The bridge 742 is provided with at least one forceps port 743. When the sheath 704 and the bridge 742 are connected to each other, the inner cavities of the forceps port 743 and the sheath 704 communicate with each other and thereby, an operative tool 744 and a suction pipe 745 (shown in FIGS. 58A to 58C) can be inserted up to the fore-end portion 704a of the sheath 704. A cock 746 is provided in the forceps port 743 in order retain water tightness when the operative tool 744 is not inserted. The operative tool 744 is provided with an electrode 747 at the fore-end and a jack 748 at the base end side.

Figure 57:
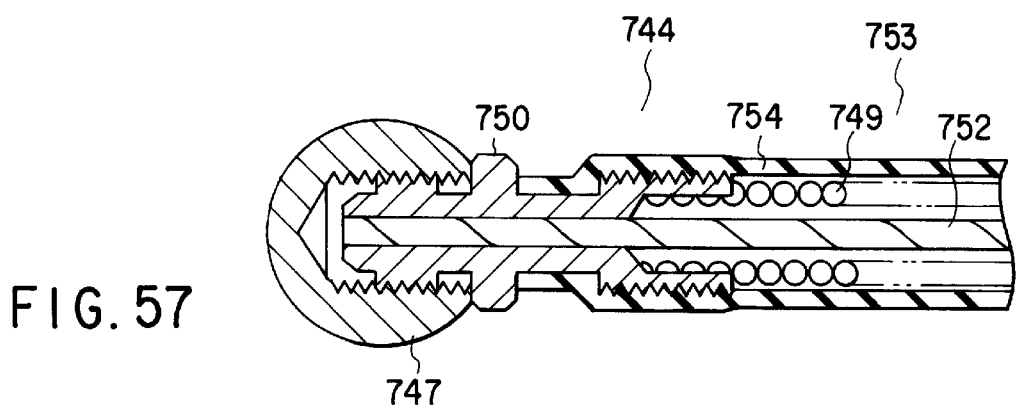
FIG. 57 is a longitudinal sectional view of a fore-end portion of the operative tool constituting the treatment tool of FIG. 56.

FIG. 57 shows a structure of the fore-end portion of the operative tool 744. A fixation member 750 is mounted on the fore-end of a coil 749 and electrically connected to a pin 751 which is provided to the jack 748 shown in FIG. 56 by an electric wire 52. The electrode 747 is mounted to the fixation member 750 in a mountable and demountable manner by screw threads. An insertion section 753 of the operative tool 744 is covered by an insulating member 754 across the entire length thereof.

Figure 58A:
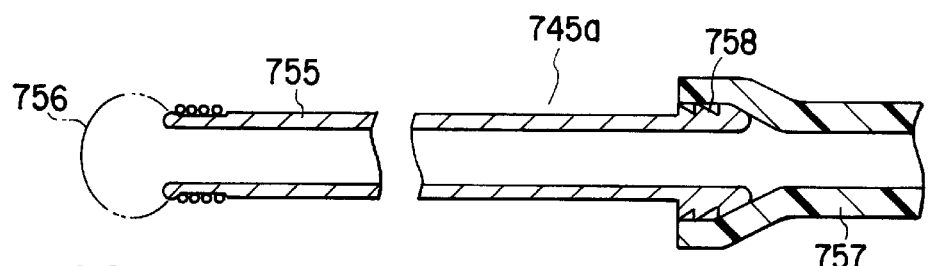
FIGS. 58A to 58C are a longitudinal sectional side view of suction pipes.
Figure 58B:
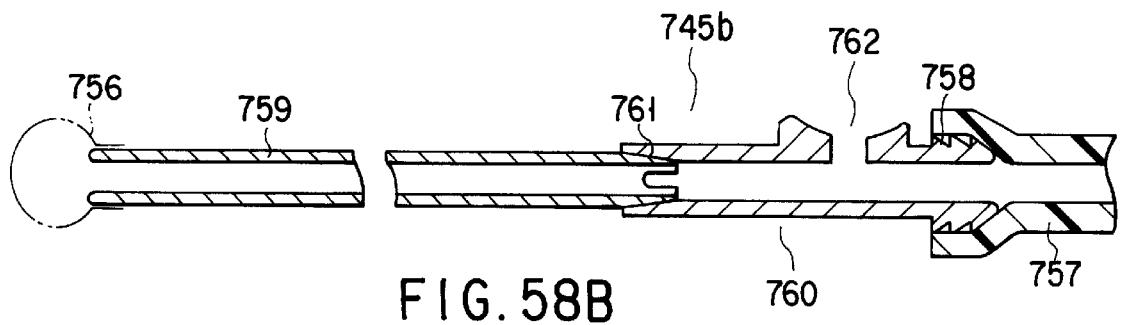
Figure 58C:
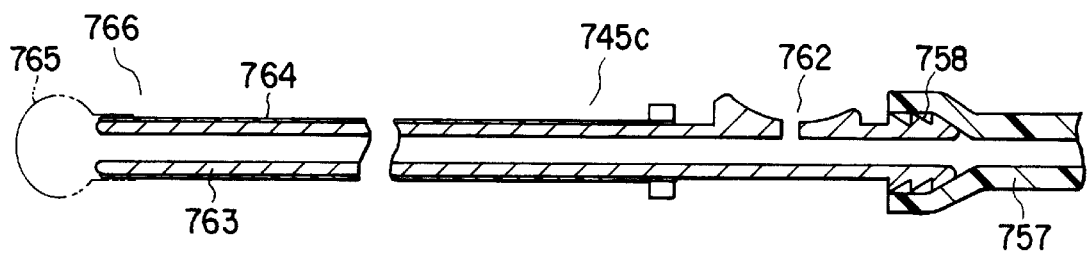

FIGS. 58A to 58C show structures of the siphon 745. Here, three kinds of suction pipes 745a, 745b, 745c will be described. In the suction pipe 745a shown. in FIG. 58A, a mesh 756 is fixed at the fore-end of a pipe 755 which is a transparent member and a mouthpiece 758 is provided to the base end thereof so that a suction tube 757 can be attached to the base. In the suction pipe 745b shown in FIG. 58B, the mesh 756 is fixed at the fore-end of a pipe 759 which is a transparent member and a connection section 761 having a tapered shape is provided to the base end thereof so that the base end can be mounted to the body 760. The mouthpiece 758 is provided to the body 760 so that the suction tube 757 can be attached to the body 760. A suction adjusting hole 762 is formed in the body 760. In the suction pipe 745c shown in FIG. 58C, the mouthpiece 758 is mounted in the base end side of a pipe 763 which is a transparent member so that the suction adjusting hole 762 and the suction tube 757 can be attached to the base end side of the pipe 763. A filter 766 of a structure in which a mesh 765 is provided at the fore-end of the a thin thickness tube 764 is mounted to the pipe 763 in a mountable and demountable manner.

Then, operations of the twenty-third embodiment will be described. The operations till the paracentesis of the sheath 704 into the prostate are same as those in the twenty-first embodiment. After the paracentesis of the sheath 704, replacement by the endoscope 702 equipped with the internal needle 707 and the bridge 742 is effected and the bridge 742 is mounted to the sheath 704. The operative tool 744 is inserted through the forceps port 743 and is further advanced up to the fore-end portion 709a of the sheath 704. The electrode 747 is positioned in place at a diseased part while confirming the diseased portion under observation using the endoscope 702 to evaporate the diseased part away. After the operation, water is sent to wash an operated portion and the water is sucked through the suction 745. According to the embodiment, evaporation of the prostate 720 can be performed without giving any damage more than necessary to the tunica mucosa of the urethra. Besides, since this procedures are performed by evaporation, an effect can be enjoyed that there arises no bleeding in the operation.

Figure 59:
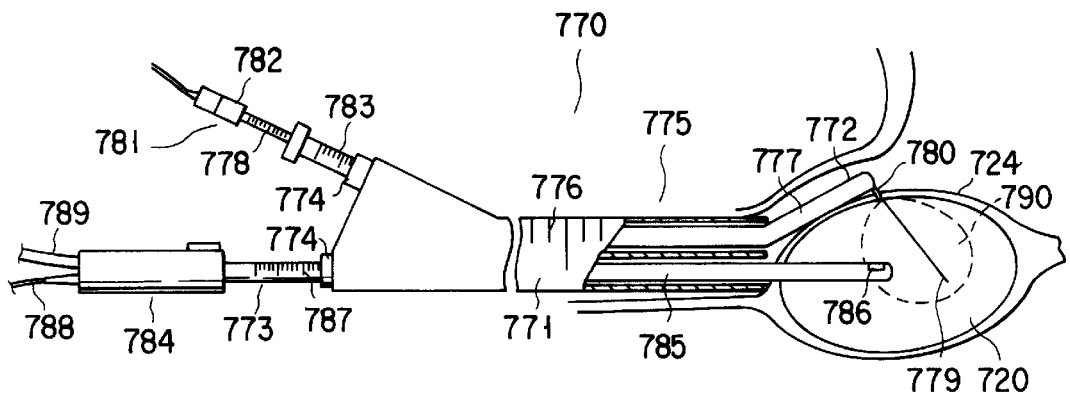
FIG. 59 is a partially cutaway side view of a treatment tool of a high frequency treatment apparatus according to a twenty-fourth embodiment of the present invention.

FIG. 59 shows the twenty-fourth embodiment and a prostatomegaly treatment apparatus 770 is constructed of: a sheath 771; a coagulation paracentesis electrode 772; and a shaver 773. The sheath 771 has two or more lumens and water seal caps 774 are respectively provided to the base end sides of the lumens. Scale marks 776 are provided on the insertion section 775 of the sheath 771 so that an insertion length can be indicated. A sheath 777 of an outer diameter which can be inserted through a lumen of the sheath 771 is provided to the paracentesis electrode 772. Scale marks 778 are provided in the base end side of the sheath 771 so that a protruded length of the fore-end of the paracentesis electrode 772 from the fore-end of the insertion section of the sheath 771 is indicated. The electrode 779 is covered with the insulating cover 780 except a paracentesis portion in the fore-end. An operation section 781 is mounted at the base end of the electrode 779, and the jack 782 for attaching a cord which is connected to a power source and scale marks 783 which indicate a protruded length of the electrode 779 are provided both in the base end thereof.

The shaver 773 comprises: a body 784; and an insertion section 785 attached to the body 784. A cutter 786 is provided at the fore-end of the insertion section 785 whose outer diameter can be inserted through the sheath 771. Scale marks 787 are provided so that a protruded length of the insertion section 785 from the sheath 771 can be indicated. A cord 788 which is connected to a controller (not shown) and a tube 789 for sucking excised tissues are connected to the body 784.

Then, operations of the twenty-fourth embodiment will be described. The sheath 771 is inserted into the urethra 771 and advanced to a position in the vicinity of the prostate 720. The paracentesis electrode 772 is inserted into the sheath 771 and paracentesis of the electrode 779 into the prostate 720 is performed while protruding the paracentesis electrode 772 from the fore-end of the sheath 771. After the paracentesis, power is supplied to coagulate tissues of the prostate 720, the insertion section 785 of the shaver 773 is inserted into the prostate 720 through the sheath 771 and an extent 790 which has been coagulated is dissected and sucked off.

According to the embodiment, since the tissues has been coagulated prior to excision by the shaver 773, no worry about bleeding is necessary. Besides, since the excision of tissues are effected without awaiting natural contraction of the coagulation extent, a quick acting treatment effect can be enjoyed.

Figure 60:
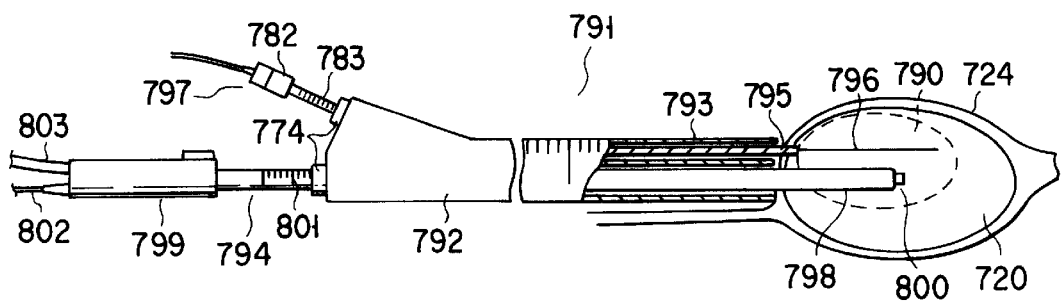
FIG. 60 is a partially cutaway side view of a treatment tool of a high frequency treatment apparatus according to a twenty-fifth embodiment of the present invention.

FIG. 60 shows the twenty-fifth embodiment. A prostatomegaly treatment apparatus 791 is constructed of: a sheath 792; a coagulation paracentesis electrode 793; and an ultrasonic suction apparatus 794. In the paracentesis electrode 793, an operation section 797 is provided at the base end of the electrode 796 on which an insulating cover is applied. In the ultrasonic suction apparatus 794, the body 799 is provided to the base end of the sheath 798, a probe 800 is inserted in an inner cavity of the sheath 798 and the base end of a probe 800 is connected to a vibrator (not shown) which is mounted in the interior of the body 799. Scale marks 801 are provided on the sheath 798 so that a protruded length of the fore-end of the sheath 798 is indicated. A cord 802 for connecting the body to a controller and a suction tube 803 are provided to the body 799.

An action and effect of the embodiment are similar to those of the twenty-fourth embodiment.

Figure 61:
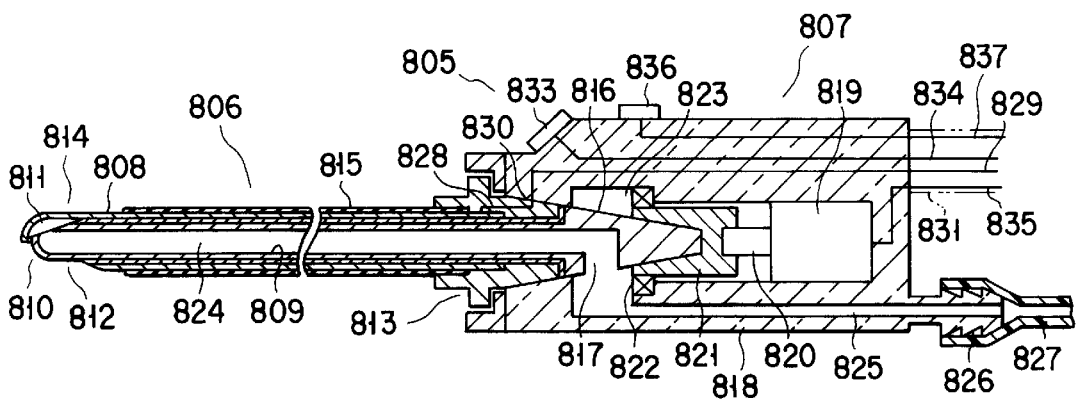
FIG. 61 is a longitudinal sectional view of a treatment tool of a high frequency treatment apparatus according to a twenty-sixth embodiment of the present invention.

FIG. 61 shows the twenty-sixth embodiment.

In a shaver 805, a body 807 is connected to the base end of an insertion section 806 in a freely mountable and demountable manner. In the insertion section 806, an inner pipe 809 is rotatably inserted in the interior of an outer pipe 808. Edged portions are provided in the peripheral portions of fore-end openings 810, 811 of the outer and inner pipes 808, 809, which constitute a cutter 812. A fixation member 813 is mounted at the base end side of the outer pipe 808 and an insulating member 815 covers the outer pipe 808 except an electrode section 814 provided at the fore-end thereof. A connection member 816 having a tapered shape is mounted to the base end of the inner pipe 809 and an opening 817 is provided in the side surface of the connection member 816.

A motor 819 is provided in the interior of a housing 818 of the body 807, an insertion section receiver 821 is connected to a shaft 820 of the motor 819 and the insertion section receiver 821 is kept water-tight by a seal 822. A space 823 is provided at a portion where the opening 817 of the connection member 816 is positioned when the insertion section 806 is mounted to the body 807, and the inner cavity 824 of the inner pipe 809 and a conduit 825 can communicate with each other at whichever position the opening 817 assumes while the connection member 816 rotates. The conduit 825 is connected to a suction tube 827 by a mouthpiece 826.

When the insertion section 806 and the body 807 are assembled, an electric wire 828 which is connected to the outer pipe 806 and an electric wire 829 which is connected to a high frequency power source apparatus (not shown) are electrically connected to each other at a terminal 830. The electric wire 829 connected to the high frequency power source apparatus, an electric wire 834 extending from an electric scalpel switch 833, an electric wire 835 extending from the motor which is connected to a shaver control unit (not shown) and an electric wire 837 extending from the shaver switch 836 are provided in a cord 831 extending from the body 807. A return electrode is provided in the insertion section 806 and electrodes of a bipolar type may be constituted.

Then, operations of the twenty-sixth embodiment will be described. A sheath performs paracentesis into the prostate as in the twenty-first and twenty-third embodiments and an insertion section 806 of the shaver 805 is inserted into the prostate. When the electric scalpel switch 833 of the body 807 is set to the ON state, a high frequency current is transmitted to the electrode section 814 from the high frequency power source apparatus and the peripheral tissues in the prostate is coagulated. After the coagulation of the tissues, when the shaver switch 836 is set to the state of ON, not only does the inner pipe 809 rotates by being driven with the motor 819, but a suction conduit constituted of the inner cavity 824, the space 823, the conduit 825, and the suction tube 827 are subjected to suction, and dissection and suction of coagulated tissues are effected.

According to the embodiment, since the tissues has been coagulated prior to the excision by the shaver 805, no worry about bleeding is necessary. Besides, since the excision of tissues is conducted without awaiting natural contraction of a coagulation extent, a quick acting treatment effect can be enjoyed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A high frequency treatment apparatus comprising:
   a high frequency generation section which supplies high frequency power;
   a control section which is connected to the high frequency generation section, and which controls output of the high frequency generation section, said control section having: (i) a first control mode in which the maximal output value of high frequency power supplied from the high frequency generation section is confined to be equal to or less than a first predetermined value, and (ii) a second control mode in which the maximal output value of high frequency power supplied from the high frequency generation section is confined to be equal to or less than a second predetermined value which is less than the first predetermined value;
   a treatment tool which is connected to the high frequency generation section, and which performs a treatment of diseased tissue by supplying high frequency power from the high frequency generation section controlled by the control section to the diseased tissue; and a control mode setting section which is connected to the control section, and which sets one of the first and second control modes;

wherein the first control mode is a high-power mode for performing coagulating and cutting operations, and the second control mode is a low-power mode for performing an ablating operation;

wherein the treatment tool has a plurality of electrodes, to which power is supplied from the high frequency generation section, and by which paracentesis into the diseased tissue is performed;

wherein the control section supplies power from the high frequency generation section to at least one of the plurality of electrodes, and at the same time stops supplying power to at least one other of the plurality of electrodes; and wherein each of the electrodes has a fore-end which is forked so as to have two needle-like portions.

2. A high frequency treatment apparatus according to claim 1, wherein:

the high frequency generation section supplies a first high frequency power and a second high frequency power whose maximal output power value is less than that of the first high frequency power, and the control section causes the high frequency generation section to supply the first high frequency power to the treatment tool in the first control mode, and to supply the second high frequency power to the treatment tool in the second control mode.

3. A high frequency treatment apparatus according to claim 1, wherein:

the control section forcibly stops output of the high frequency generation section after a predetermined time elapses in the first control mode.

4. A high frequency treatment apparatus according to claim 1, wherein:

the high frequency generation section has a plurality of output terminals and the electrodes are respectively connected to the output terminals, and the high frequency generation section supplies power to at least one of the output terminals, and at the same time stops supplying power to at least one other of the output terminals under control of the control section.

5. A high frequency treatment apparatus according to claim 1, wherein:

the control section sequentially supplies power from the high frequency generation section to the electrodes.

6. A high frequency treatment apparatus according to claim 1, further comprising:

a detection section which detects a temperature of a peripheral portion of the diseased tissue or biogenic information which has a correlation with the temperature of the diseased tissue, and wherein the control section controls output of the high frequency generation section based on detection information from the detection section, and alternately performs power supply to one of the electrodes from the high frequency generation section and reception of detection information input from the detection section.

7. A high frequency treatment apparatus comprising:

a high frequency generation section which supplies high frequency power;

a control section which is connected to the high frequency generation section, and which controls output of the high frequency generation section, said control section having: (i) a first control mode in which the maximal output value of high frequency power supplied from the high frequency generation section is confined to be equal to or less than a first predetermined value, and (ii) a second control mode in which the maximal output value of high frequency power supplied from the high frequency generation section is confined to be equal to or less than a second predetermined value which is less than the first predetermined value;

a treatment tool which is connected to the high frequency generation section, and which performs a treatment of diseased tissue by supplying high frequency power from the high frequency generation section controlled by the control section to the diseased tissue; and a control mode setting section which is connected to the control section, and which sets one of the first and second control modes;

wherein the first control mode is a high-power mode for performing coagulating and cutting operations, and the second control mode is a low-power mode for performing an ablating operation; and wherein the treatment tool comprises:

an insertion section which can be inserted into a biogenic lumen, and which has at least one channel which extends along a lengthwise direction of the insertion section;

a sheath which can be inserted through at least one of said at least one channel of the insertion section;

a first electrode which is provided at a fore-end of the sheath in an exposed manner, and which can be supplied with power from the high frequency generation section;

a second electrode which is provided along an outer periphery of a fore-end portion of the insertion section, and which along with the first electrode is adapted to have a high frequency current supplied therebetween; and guiding means for guiding the sheath out of the channel through which the sheath is inserted at a predetermined angle to a lengthwise central axis of the insertion section, wherein the guiding means communicates with said channel and has a hole extending through the outer periphery of the fore-end portion of the insertion section where the second electrode is provided, so that the first electrode protrudes from said channel through the hole at the predetermined angle.

8. A high frequency treatment apparatus: according to claim 7, further comprising:

a balloon which is provided at a fore-end of the insertion section, and which is inflated by fluid with which an interior of the balloon is filled; and a channel which is formed in the insertion section, and through which the fluid is supplied into the balloon.

9. A high frequency treatment apparatus according to claim 7, wherein:

the sheath is inserted through the channel of the insertion section in a forward and backward movable manner, and the first electrode is inserted through the sheath in a freely forward and backward movable manner and has an electrically insulating section at a fore-end thereof, and the apparatus further comprises:

a first operation section which is connected to the sheath, and which is used for moving the sheath in the channel forward and backward; and a second operation section which is connected to the first electrode, and which is used for moving the first electrode in the sheath forward and backward.

10. A high frequency treatment apparatus comprising:

a high frequency generation section which supplies high frequency power;

a control section which is connected to the high frequency generation section, and which controls output of the high frequency generation section, said control section having: (i) a first control mode in which the maximal output value of high frequency power supplied from the high frequency generation section is confined to be equal to or less than a first predetermined value, and (ii) a second control mode in which the maximal output value of high frequency power supplied from the high frequency generation section is confined to be equal to or less than a second predetermined value which is less than the first predetermined value;

a treatment tool which is connected to the high frequency generation section, and which performs a treatment of diseased tissue by supplying high frequency power from the high frequency generation section controlled by the control section to the diseased tissue; and a control mode setting section which is connected to the control section, and which sets one of the first and second control modes;

wherein the first control mode is a high-power mode for performing coagulating and cutting operations, and the second control mode is a low-power mode for performing an ablating operation; and wherein the treatment tool comprises:

a sheath having at least one channel;

an internal needle which is removably insertable in the channel of the sheath, paracentesis into biogenic tissues together with the sheath;

a tissue removal tool which is also removably insertable into the channel of the sheath, said tissue removal tool having an electrode to which power is supplied from the high frequency generation section and being adapted to perform removal of the diseased tissue using the electrode; and a mandrin which is also removably insertable in the channel of the sheath, wherein the internal needle, the mandrin and the tissue removal tool are selectively inserted into the sheath.

11. A high frequency treatment apparatus according to claim 10, wherein the tissue removal tool comprises:

an endoscope;

a stabilizer on which the electrode is provided, and which is mounted to the endoscope in a forward and backward movable manner; and an operation mechanism that moves the stabilizer along a lengthwise direction of the endoscope forward or backward.

12. A high frequency treatment apparatus according to claim 10, wherein the internal needle comprises:

a vibrator which oscillates ultrasonic oscillation;

a hone which is connected to the vibrator, and which amplifies the ultrasonic oscillation; and a blade portion which is connected to the hone.

13. A high frequency treatment apparatus according to claim 10, wherein:

the sheath is provided with a first channel and a second channel, and a bridge having mouthpieces which respectively communicate with the channels in the sheath is provided at a base end of the sheath.

14. A high frequency treatment apparatus according to claim 13, wherein:

the tissue removal tool comprises an endoscope which is inserted through the first channel of the sheath, and an operative tool and a suction pipe which are inserted through the second channel of the sheath, the operative tool comprises a sheath which has a fixation section by which the electrode is fixed in a freely mountable and demountable manner at a fore-end thereof, and a power supply wire which is provided in the sheath and which electrically connects the electrode to the high frequency generation section, and the operative tool and the suction pipe are selectively inserted through the second channel.

15. A high frequency treatment apparatus according to claim 13, wherein:

the tissue removal tool comprises a first operative tool which is inserted through the first channel of the sheath, and a second operative tool which is inserted through the second channel of the sheath, the first operative tool comprises a first sheath section which is inserted through the first channel in a forward and backward movable manners, and the electrode which is inserted in the first sheath section in a forward and backward movable manner, the second operative tool comprises a second sheath section which is inserted through the second channel in a forward and backward movable manner, and a cutter which is provided at a fore-end of the second sheath section, scale marks which indicate a protruded length of the first sheath section from a fore-end of the first channel are provided in a base end side of the first sheath section, scale marks which indicate a protruded length of the electrode from a fore-end of the first sheath section are provided in a base end side of the electrode, and scale marks which indicate a protruded length of the second sheath section from a fore-end of the second channel are provided in a base end side of the second sheath section.

* * * * *

UNITED STATES PATENT AND TRADEMARK OFFICE
CERTIFICATE OF CORRECTION

PATENT NO. : 6,383,183 B1
DATED : May 7, 2002
INVENTOR(S) : Naomi Sekino et al.

It is certified that error appears in the above-identified patent and that said Letters Patent is hereby corrected as shown below:

Title page,
Item [56], References Cited, U.S. PATENT DOCUMENTS, insert:

```
--5,370,675   *   12/1994    Edwards et al
  5,540,683   *    7/1996    Ichikawa et al
  5,372,138   *   12/1994    Crowley et al
  5,873,877   *    2/1999    McGaffigan et al
  5,964,727   *   10/1999    Edwards et al
  4,903,696   *    2/1990    Stasz et al
  4,524,770   *    6/1985    Orandi
  3,942,530   *    3/1976    Northeved
  5,020,539   *    6/1991    Yokoi et al
  5,928,163   *    7/1999    Roberts et al
  5,484,400   *    1/1996    Edwards et al--.
```

Signed and Sealed this

Eighteenth Day of May, 2004

JON W. DUDAS
*Acting Director of the United States Patent and Trademark Office*